(12) United States Patent
Kugler et al.

(10) Patent No.: US 9,788,855 B2
(45) Date of Patent: Oct. 17, 2017

(54) ENDOVASCULAR DEVICES AND METHODS FOR EXPLOITING INTRAMURAL SPACE

(71) Applicant: Bridgepoint Medical, Inc., Plymouth, MN (US)

(72) Inventors: Chad J. Kugler, Andover, MN (US); Robert E. Atkinson, White Bear Lake, MN (US); Matthew J. Olson, Crystal, MN (US)

(73) Assignee: BridgePoint Medical, Inc., Plymouth, MN (US)

( * ) Notice: Subject to any disclaimer, the term of this patent is extended or adjusted under 35 U.S.C. 154(b) by 227 days.

(21) Appl. No.: 14/553,069

(22) Filed: Nov. 25, 2014

(65) Prior Publication Data

US 2015/0080928 A1  Mar. 19, 2015

Related U.S. Application Data

(63) Continuation of application No. 13/660,919, filed on Oct. 25, 2012, now Pat. No. 8,961,494, which is a
(Continued)

(51) Int. Cl.
*A61B 17/34* (2006.01)
*A61B 17/22* (2006.01)
(Continued)

(52) U.S. Cl.
CPC ........ *A61B 17/3403* (2013.01); *A61B 17/221* (2013.01); *A61B 17/22031* (2013.01);
(Continued)

(58) Field of Classification Search
CPC .... A61B 2017/320741; A61B 17/3207; A61B 17/320725; A61B 2017/22095;
(Continued)

(56) References Cited

U.S. PATENT DOCUMENTS 4,020,829 A   5/1977  Willson et al.
4,233,983 A  11/1980  Rocco
(Continued)

FOREIGN PATENT DOCUMENTS

EP   1342486 A1   9/2003
WO   0178822 A2  10/2001
(Continued)

OTHER PUBLICATIONS

International Search Report in PCT/US06/35244 dated Mar. 24, 2008.
(Continued)

*Primary Examiner* — Bradley Osinski
(74) *Attorney, Agent, or Firm* — Seager, Tufte & Wickhem LLP

(57) ABSTRACT

Devices and methods for the treatment of chronic total occlusions are provided. One disclosed embodiment comprises a method of facilitating treatment via a vascular wall defining a vascular lumen containing an occlusion therein. The method includes inserting an intramural crossing device into the vascular lumen, positioning at least the distal tip of the crossing device in the vascular wall, advancing an orienting device over the crossing device such that an orienting element of the orienting device resides in the vascular wall, inserting a reentry device, and re-entering the true vascular lumen.

19 Claims, 67 Drawing Sheets

Related U.S. Application Data continuation of application No. 11/518,430, filed on Sep. 11, 2006, now Pat. No. 8,323,261.

(60) Provisional application No. 60/839,782, filed on Aug. 24, 2006, provisional application No. 60/811,478, filed on Jun. 7, 2006, provisional application No. 60/727,819, filed on Oct. 18, 2005, provisional application No. 60/717,726, filed on Sep. 15, 2005, provisional application No. 60/716,287, filed on Sep. 12, 2005.

(51) Int. Cl.
| | | |
|---|---|---|
| *A61B 17/221* | (2006.01) | |
| *A61B 17/3207* | (2006.01) | |
| *A61F 2/88* | (2006.01) | |
| *A61M 25/04* | (2006.01) | |
| *A61M 25/10* | (2013.01) | |
| *A61B 17/00* | (2006.01) | |
| *A61B 17/3205* | (2006.01) | |
| *A61B 17/32* | (2006.01) | |
| *A61M 25/00* | (2006.01) | |
| *A61M 25/01* | (2006.01) | |
| *A61M 25/09* | (2006.01) | |

(52) U.S. Cl.
CPC ............... *A61B 17/32075* (2013.01); *A61B 17/320758* (2013.01); *A61B 17/3415* (2013.01); *A61B 17/3417* (2013.01); *A61B 17/3476* (2013.01); *A61F 2/88* (2013.01); *A61M 25/0074* (2013.01); *A61M 25/04* (2013.01); *A61M 25/10* (2013.01); *A61B 17/00008* (2013.01); *A61B 17/32053* (2013.01); *A61B 2017/003* (2013.01); *A61B 2017/00252* (2013.01); *A61B 2017/00455* (2013.01); *A61B 2017/00685* (2013.01); *A61B 2017/2212* (2013.01); *A61B 2017/22034* (2013.01); *A61B 2017/22038* (2013.01); *A61B 2017/22044* (2013.01); *A61B 2017/22077* (2013.01); *A61B 2017/22094* (2013.01); *A61B 2017/22095* (2013.01); *A61B 2017/320004* (2013.01); *A61B 2017/320044* (2013.01); *A61B 2017/320064* (2013.01); *A61B 2017/320741* (2013.01); *A61B 2017/3405* (2013.01); *A61B 2017/3454* (2013.01); *A61M 25/003* (2013.01); *A61M 25/007* (2013.01); *A61M 25/0032* (2013.01); *A61M 25/0045* (2013.01); *A61M 25/0069* (2013.01); *A61M 25/0082* (2013.01); *A61M 25/0152* (2013.01); *A61M 2025/006* (2013.01); *A61M 2025/018* (2013.01); *A61M 2025/09175* (2013.01); *A61M 2025/09191* (2013.01); *A61M 2025/105* (2013.01)

(58) Field of Classification Search
CPC .... A61B 17/32075; A61B 2017/22077; A61B 2017/22051; A61B 2017/320044; A61B 2017/22094
See application file for complete search history.

(56) References Cited

U.S. PATENT DOCUMENTS

| | | |
|---|---|---|
| 4,569,347 A | 2/1986 | Frisbie |
| 4,581,017 A | 4/1986 | Sahota |
| 4,621,636 A | 11/1986 | Fogarty |
| 4,747,821 A | 5/1988 | Kensey et al. |
| 4,762,130 A | 8/1988 | Fogarty et al. |
| 4,774,949 A | 10/1988 | Fogarty et al. |
| 4,819,634 A | 4/1989 | Shiber et al. |
| 4,878,495 A | 11/1989 | Grayzel |
| 4,976,689 A | 12/1990 | Buchbinder et al. |
| 4,979,939 A | 12/1990 | Shiber et al. |
| 5,071,406 A | 12/1991 | Jang et al. |
| 5,127,917 A | 7/1992 | Niederhauser et al. |
| 5,193,546 A | 3/1993 | Shaknovich |
| 5,201,753 A | 4/1993 | Lampropoulos et al. |
| 5,263,493 A | 11/1993 | Avitall |
| 5,275,610 A | 1/1994 | Eberbach et al. |
| 5,324,263 A | 6/1994 | Kraus et al. |
| 5,356,418 A | 10/1994 | Shturman |
| 5,372,587 A | 12/1994 | Hammerslag et al. |
| 5,383,856 A | 1/1995 | Bersin |
| 5,385,152 A | 1/1995 | Abele et al. |
| 5,409,453 A | 4/1995 | Lundquist et al. |
| 5,415,637 A | 5/1995 | Khosravi et al. |
| 5,464,395 A | 11/1995 | Faxon et al. |
| 5,501,667 A | 3/1996 | Verduin, Jr. |
| 5,505,702 A | 4/1996 | Arney |
| 5,534,007 A | 7/1996 | St. Germain et al. |
| 5,555,883 A | 9/1996 | Avitall |
| 4,990,134 B1 | 11/1996 | Auth |
| 5,571,122 A | 11/1996 | Kelly et al. |
| 5,571,169 A | 11/1996 | Plaia et al. |
| 5,599,326 A * | 2/1997 | Carter ............... A61M 25/0045 604/524 |
| 5,603,720 A | 2/1997 | Kieturakis |
| 5,643,298 A | 7/1997 | Nordgren et al. |
| 5,655,548 A | 8/1997 | Nelson et al. |
| 5,695,506 A | 12/1997 | Pike et al. |
| 5,728,133 A | 3/1998 | Kontos et al. |
| 5,741,270 A | 4/1998 | Hansen et al. |
| 5,741,429 A | 4/1998 | Donadio, III et al. |
| 5,779,721 A | 7/1998 | Nash et al. |
| 5,807,241 A | 9/1998 | Heimberger et al. |
| 5,824,071 A | 10/1998 | Nelson et al. |
| 5,830,222 A | 11/1998 | Makower |
| 5,830,224 A | 11/1998 | Cohn et al. |
| 5,843,050 A | 12/1998 | Jones et al. |
| 5,910,133 A | 6/1999 | Gould et al. |
| 5,916,194 A | 6/1999 | Jacobsen et al. |
| 5,935,108 A | 8/1999 | Katoh et al. |
| 5,944,686 A | 8/1999 | Patterson et al. |
| 5,954,713 A | 9/1999 | Newman et al. |
| 5,957,900 A | 9/1999 | Ouchi |
| 5,968,064 A | 10/1999 | Selmon et al. |
| 5,989,276 A | 11/1999 | Houser et al. |
| 6,010,449 A | 1/2000 | Selmon et al. |
| 6,013,055 A | 1/2000 | Bampos et al. |
| 6,015,405 A | 1/2000 | Schwartz et al. |
| 6,022,343 A | 2/2000 | Johnson et al. |
| 6,036,707 A | 3/2000 | Spaulding et al. |
| 6,036,717 A | 3/2000 | Mers Kelly et al. |
| 6,059,750 A | 5/2000 | Fogarty et al. |
| 6,068,638 A | 5/2000 | Makower |
| 6,071,281 A | 6/2000 | Burnside et al. |
| 6,071,292 A | 6/2000 | Makower et al. |
| 6,081,738 A | 6/2000 | Hinohara et al. |
| 6,099,542 A | 8/2000 | Cohn et al. |
| 6,117,064 A | 9/2000 | Apple et al. |
| 6,120,516 A | 9/2000 | Selmon et al. |
| 6,126,649 A | 10/2000 | VanTassel et al. |
| 6,155,264 A | 12/2000 | Ressemann et al. |
| 6,157,852 A | 12/2000 | Selmon et al. |
| 6,159,225 A | 12/2000 | Makower |
| 6,183,432 B1 | 2/2001 | Milo |
| 6,186,972 B1 | 2/2001 | Nelson et al. |
| 6,190,353 B1 | 2/2001 | Makower et al. |
| 6,203,559 B1 | 3/2001 | Davis et al. |
| 6,217,527 B1 | 4/2001 | Selmon et al. |
| 6,217,549 B1 | 4/2001 | Selmon et al. |
| 6,221,049 B1 | 4/2001 | Selmon et al. |
| 6,231,546 B1 | 5/2001 | Milo et al. |
| 6,231,587 B1 | 5/2001 | Makower |
| 6,235,000 B1 | 5/2001 | Milo et al. |
| 6,241,667 B1 | 6/2001 | Vetter et al. |
| 6,246,914 B1 | 6/2001 | de la Rama et al. |

(56) References Cited

U.S. PATENT DOCUMENTS

| | | |
|---|---|---|
| 6,254,588 B1 | 7/2001 | Jones et al. |
| 6,258,052 B1 | 7/2001 | Milo |
| 6,266,550 B1 | 7/2001 | Selmon et al. |
| 6,277,133 B1 | 8/2001 | Kanesaka |
| 6,283,940 B1 | 9/2001 | Mulholland |
| 6,283,951 B1 | 9/2001 | Flaherty et al. |
| 6,283,983 B1 | 9/2001 | Makower et al. |
| 6,287,317 B1 | 9/2001 | Makower et al. |
| 6,302,875 B1 | 10/2001 | Makower et al. |
| 6,330,884 B1 | 12/2001 | Kim |
| 6,337,142 B2 | 1/2002 | Harder et al. |
| 6,358,244 B1 | 3/2002 | Newman et al. |
| 6,375,615 B1 | 4/2002 | Flaherty et al. |
| 6,379,319 B1 | 4/2002 | Garibotto et al. |
| 6,387,119 B2 | 5/2002 | Wolf et al. |
| 6,398,798 B2 | 6/2002 | Selmon et al. |
| 6,416,523 B1 | 7/2002 | Lafontaine |
| 6,428,552 B1 | 8/2002 | Sparks |
| 6,432,127 B1 | 8/2002 | Kim et al. |
| 6,447,539 B1 | 9/2002 | Nelson et al. |
| 6,475,226 B1 | 11/2002 | Belef et al. |
| 6,485,458 B1 | 11/2002 | Takahashi |
| 6,491,660 B2 | 12/2002 | Guo et al. |
| 6,491,707 B2 | 12/2002 | Makower et al. |
| 6,506,178 B1 | 1/2003 | Schubart et al. |
| 6,508,824 B1 | 1/2003 | Flaherty et al. |
| 6,508,825 B1 | 1/2003 | Selmon et al. |
| 6,511,458 B2 | 1/2003 | Milo et al. |
| 6,514,217 B1* | 2/2003 | Selmon .............. A61B 17/3207 600/585 |
| 6,544,230 B1 | 4/2003 | Flaherty et al. |
| 6,561,998 B1 | 5/2003 | Roth et al. |
| 6,565,583 B1 | 5/2003 | Deaton |
| 6,569,143 B2 | 5/2003 | Alchas et al. |
| 6,569,145 B1 | 5/2003 | Shmulewitz et al. |
| 6,569,150 B2 | 5/2003 | Teague et al. |
| 6,579,311 B1 | 6/2003 | Makower |
| 6,589,164 B1 | 7/2003 | Flaherty |
| 6,599,304 B1 | 7/2003 | Selmon et al. |
| 6,602,241 B2 | 8/2003 | Makower et al. |
| 6,613,081 B2 | 9/2003 | Kim et al. |
| 6,616,675 B1 | 9/2003 | Evard et al. |
| 6,623,448 B2 | 9/2003 | Slater |
| 6,638,247 B1 | 10/2003 | Selmon et al. |
| 6,638,293 B1 | 10/2003 | Makower et al. |
| 6,655,386 B1 | 12/2003 | Makower et al. |
| 6,656,195 B2 | 12/2003 | Peters et al. |
| 6,660,024 B1 | 12/2003 | Flaherty et al. |
| 6,669,709 B1 | 12/2003 | Cohn et al. |
| 6,685,648 B2 | 2/2004 | Flaherty et al. |
| 6,685,716 B1 | 2/2004 | Flaherty et al. |
| 6,694,983 B2 | 2/2004 | Wolf et al. |
| 6,709,444 B1 | 3/2004 | Makower |
| 6,719,725 B2 | 4/2004 | Milo et al. |
| 6,726,677 B1* | 4/2004 | Flaherty .............. A61B 1/3137 600/439 |
| 6,746,426 B1 | 6/2004 | Flaherty et al. |
| 6,746,462 B1 | 6/2004 | Selmon et al. |
| 6,746,464 B1 | 6/2004 | Makower |
| 6,786,884 B1 | 9/2004 | DeCant, Jr. et al. |
| 6,800,085 B2 | 10/2004 | Selmon et al. |
| 6,824,550 B1 | 11/2004 | Noriega et al. |
| 6,830,577 B2 | 12/2004 | Nash et al. |
| 6,837,868 B1 | 1/2005 | Fajnsztajn |
| 6,860,892 B1 | 3/2005 | Tanaka |
| 6,863,684 B2 | 3/2005 | Kim et al. |
| 6,866,676 B2 | 3/2005 | Kieturakis et al. |
| 6,884,225 B2 | 4/2005 | Kato et al. |
| 6,905,505 B2 | 6/2005 | Nash et al. |
| 6,929,009 B2 | 8/2005 | Makower et al. |
| 6,936,056 B2 | 8/2005 | Nash et al. |
| 6,942,641 B2 | 9/2005 | Seddon |
| 6,949,125 B2 | 9/2005 | Robertson |
| 6,991,617 B2 | 1/2006 | Hektner et al. |
| 7,004,173 B2 | 2/2006 | Sparks et al. |
| 7,056,325 B1 | 6/2006 | Makower et al. |
| 7,059,330 B1 | 6/2006 | Makower et al. |
| 7,083,588 B1 | 8/2006 | Shmulewitz et al. |
| 7,094,230 B2 | 8/2006 | Flaherty et al. |
| 7,105,031 B2 | 9/2006 | Letort |
| 7,134,438 B2 | 11/2006 | Makower et al. |
| 7,137,990 B2 | 11/2006 | Hebert et al. |
| 7,159,592 B1 | 1/2007 | Makower et al. |
| 7,179,270 B2 | 2/2007 | Makower |
| 7,191,015 B2 | 3/2007 | Lamson et al. |
| 7,229,421 B2 | 6/2007 | Jen et al. |
| 7,316,655 B2 | 1/2008 | Garibotto et al. |
| 7,377,910 B2 | 5/2008 | Katoh et al. |
| 7,465,286 B2 | 12/2008 | Patterson et al. |
| 2001/0000041 A1 | 3/2001 | Selmon et al. |
| 2001/0056273 A1 | 12/2001 | C. |
| 2002/0029052 A1 | 3/2002 | Evans et al. |
| 2002/0052637 A1 | 5/2002 | Houser et al. |
| 2002/0103459 A1 | 8/2002 | Sparks et al. |
| 2003/0028200 A1 | 2/2003 | Berg et al. |
| 2003/0040737 A1 | 2/2003 | Merril et al. |
| 2003/0109809 A1 | 6/2003 | Jen et al. |
| 2003/0167038 A1 | 9/2003 | Yozu et al. |
| 2003/0236542 A1 | 12/2003 | Makower |
| 2004/0015193 A1 | 1/2004 | Lamson et al. |
| 2004/0059280 A1 | 3/2004 | Makower et al. |
| 2004/0102719 A1 | 5/2004 | Keith et al. |
| 2004/0133225 A1 | 7/2004 | Makower |
| 2004/0158143 A1 | 8/2004 | Flaherty et al. |
| 2004/0167554 A1 | 8/2004 | Simpson et al. |
| 2004/0230156 A1 | 11/2004 | Schreck et al. |
| 2004/0249277 A1 | 12/2004 | Kato et al. |
| 2004/0249338 A1 | 12/2004 | DeCant, Jr. et al. |
| 2005/0038467 A1 | 2/2005 | Hebert et al. |
| 2005/0049574 A1 | 3/2005 | Petrick et al. |
| 2005/0171478 A1 | 8/2005 | Selmon et al. |
| 2005/0177105 A1* | 8/2005 | Shalev .............. A61M 25/1002 604/104 |
| 2005/0216044 A1 | 9/2005 | Hong |
| 2005/0261663 A1 | 11/2005 | Patterson et al. |
| 2006/0094930 A1 | 5/2006 | Sparks et al. |
| 2006/0135984 A1 | 6/2006 | Kramer et al. |
| 2006/0271078 A1 | 11/2006 | Modesitt |
| 2007/0083220 A1 | 4/2007 | Shamay |
| 2007/0088230 A1 | 4/2007 | Terashi et al. |
| 2007/0093779 A1 | 4/2007 | Kugler et al. |
| 2007/0093780 A1 | 4/2007 | Kugler et al. |
| 2007/0093782 A1 | 4/2007 | Kugler et al. |
| 2007/0093783 A1 | 4/2007 | Kugler et al. |
| 2007/0265596 A1 | 11/2007 | Jen et al. |
| 2008/0103443 A1 | 5/2008 | Kabrick et al. |
| 2008/0228171 A1 | 9/2008 | Kugler et al. |
| 2008/0243065 A1 | 10/2008 | Rottenberg et al. |
| 2008/0243067 A1 | 10/2008 | Rottenberg et al. |
| 2009/0088685 A1 | 4/2009 | Kugler et al. |
| 2009/0124899 A1 | 5/2009 | Jacobs et al. |
| 2009/0209910 A1 | 8/2009 | Kugler et al. |
| 2009/0270890 A1 | 10/2009 | Robinson et al. |
| 2010/0063534 A1 | 3/2010 | Kugler et al. |
| 2010/0069945 A1 | 3/2010 | Olson et al. |

FOREIGN PATENT DOCUMENTS

| | | |
|---|---|---|
| WO | 2007033052 A2 | 3/2007 |
| WO | 2008063621 A2 | 5/2008 |
| WO | 2009054943 A1 | 4/2009 |
| WO | 2009100129 A2 | 8/2009 |
| WO | 2009134346 A2 | 11/2009 |
| WO | 2010019241 A1 | 2/2010 |
| WO | 2010044816 A1 | 4/2010 |

OTHER PUBLICATIONS

Written Opinion of International Searching Authority in PCT/US06/35244 dated Mar. 24, 2008.

International Preliminary Report on Patentability in PCT/US06/35244 dated Mar. 17, 2009.

(56) References Cited

OTHER PUBLICATIONS

Bolia, Amman, Subintimal Angioplasty: Which Cases to Choose, How to Avoid Pitfalls and Technical Tips, Combined Session: Vascular Surgery and Interventional Radiology, pp. III 8. 1-8.3.
Colombo, Antonio et al., Treating Chronic Total Occlusions Using Subintimal Tracking and Reentry: The STAR Technique, Catheterization and Cardiovascular Interventions, vol. 64: 407-411 (2005).

* cited by examiner

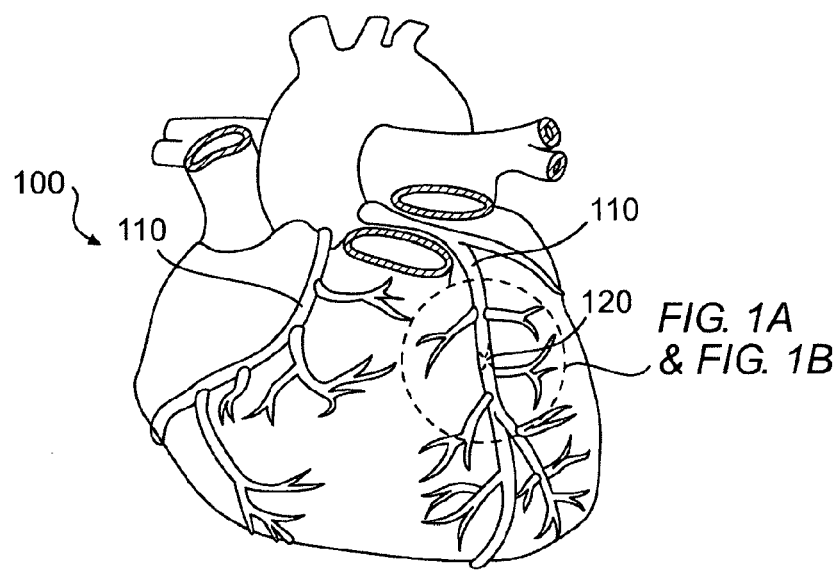
FIG. 1
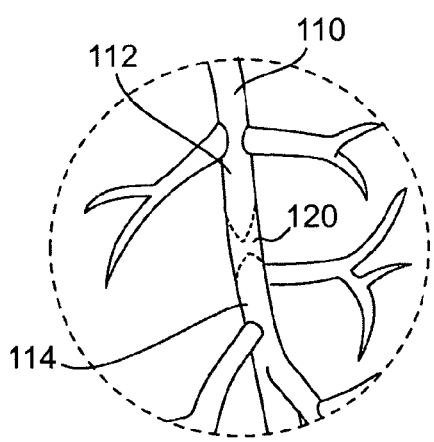 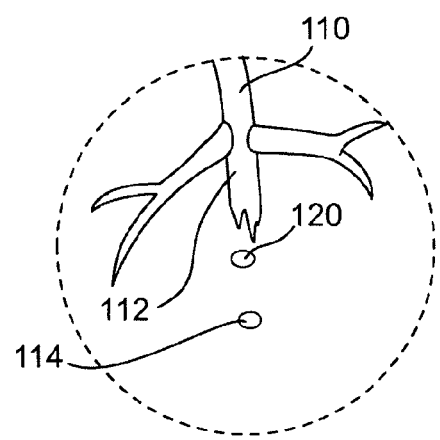
FIG. 1A  FIG. 1B

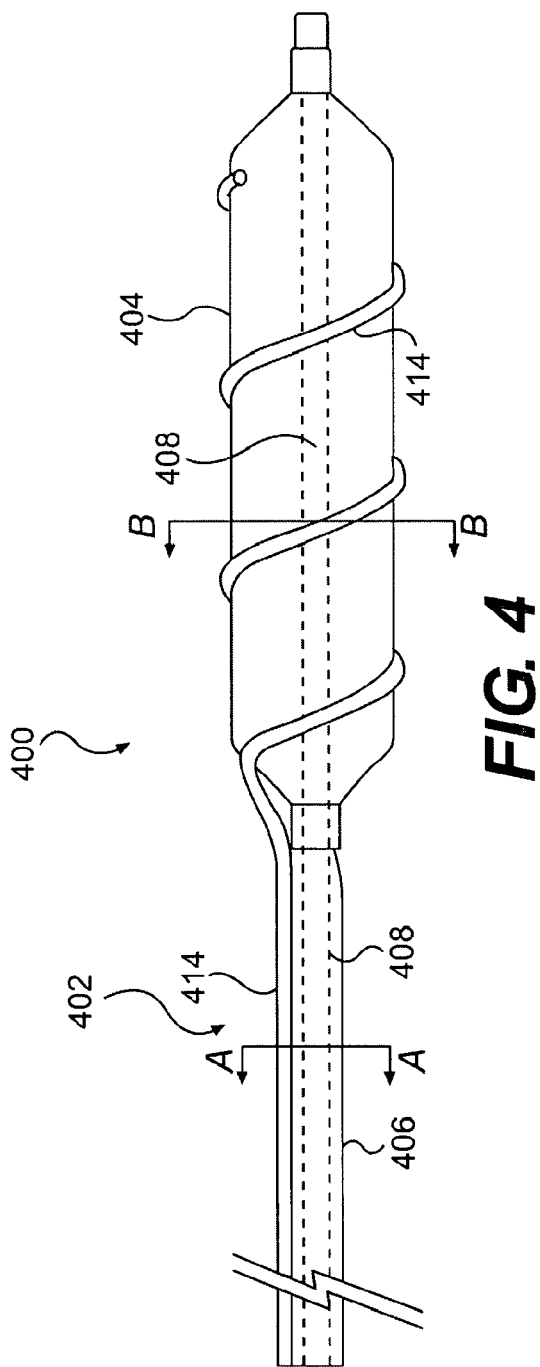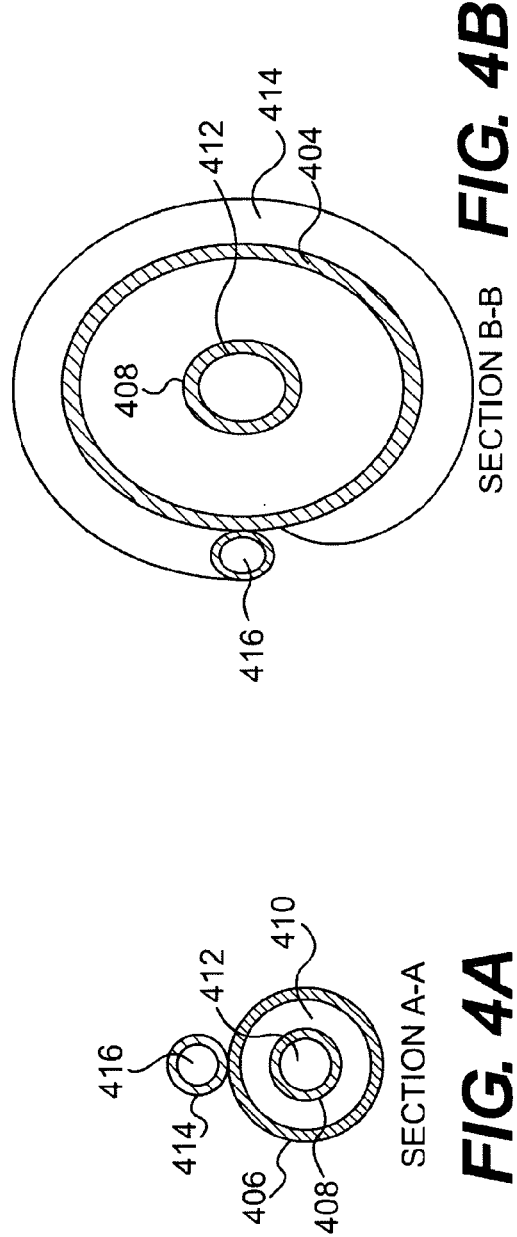
FIG. 4
FIG. 4A SECTION A-A
FIG. 4B SECTION B-B

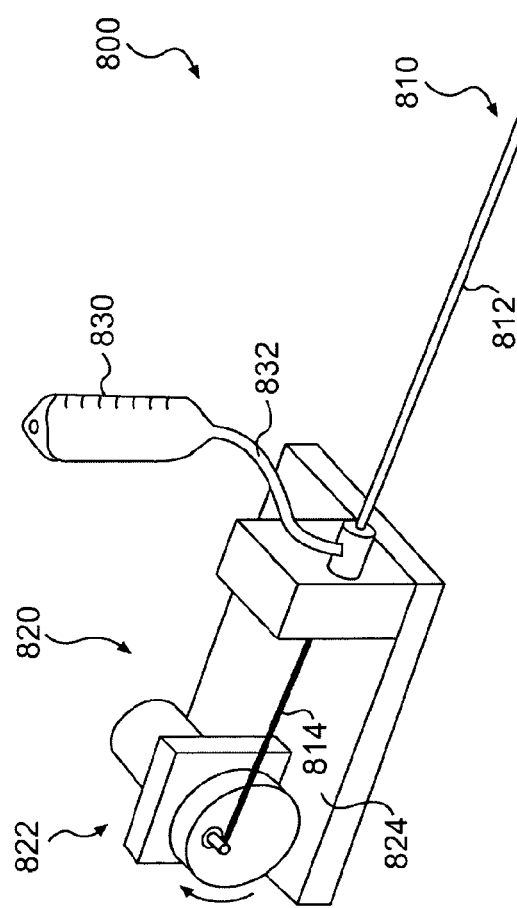
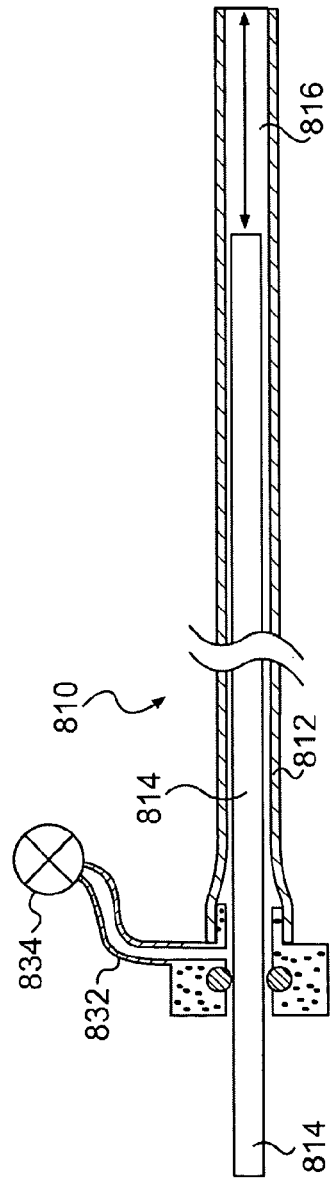
FIG. 8A
FIG. 8B

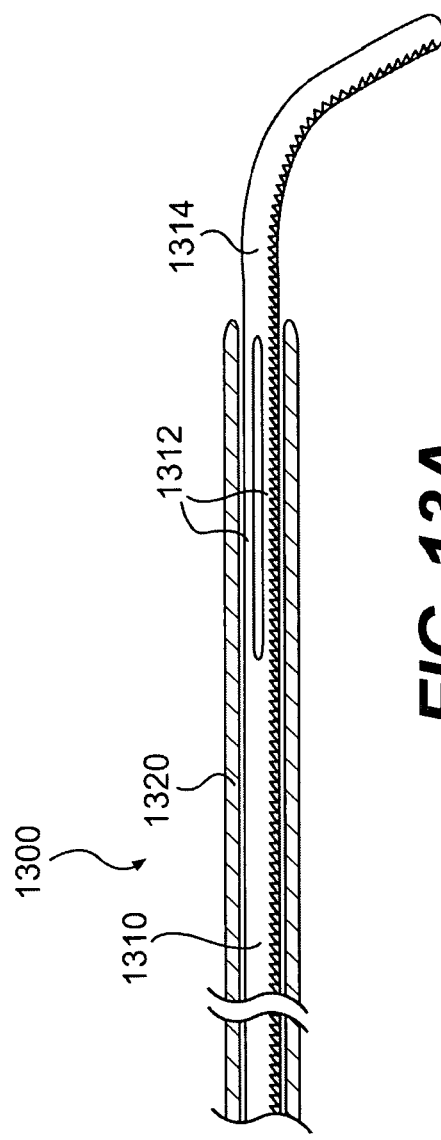
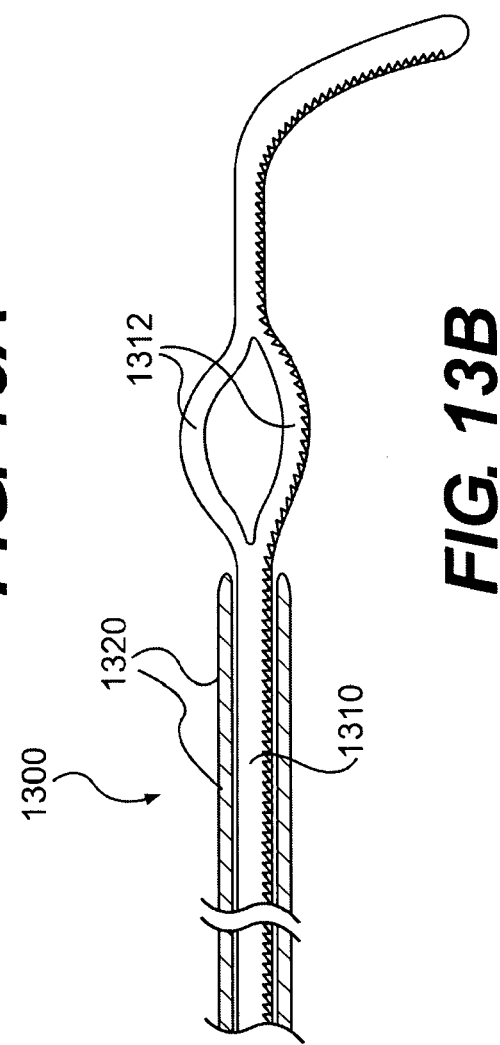

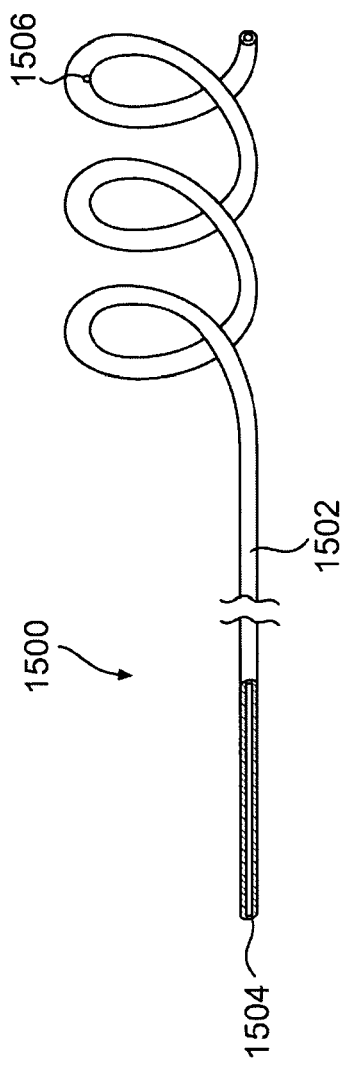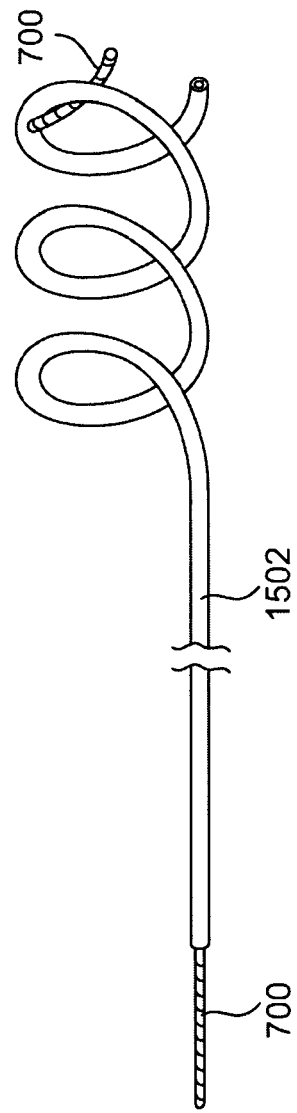

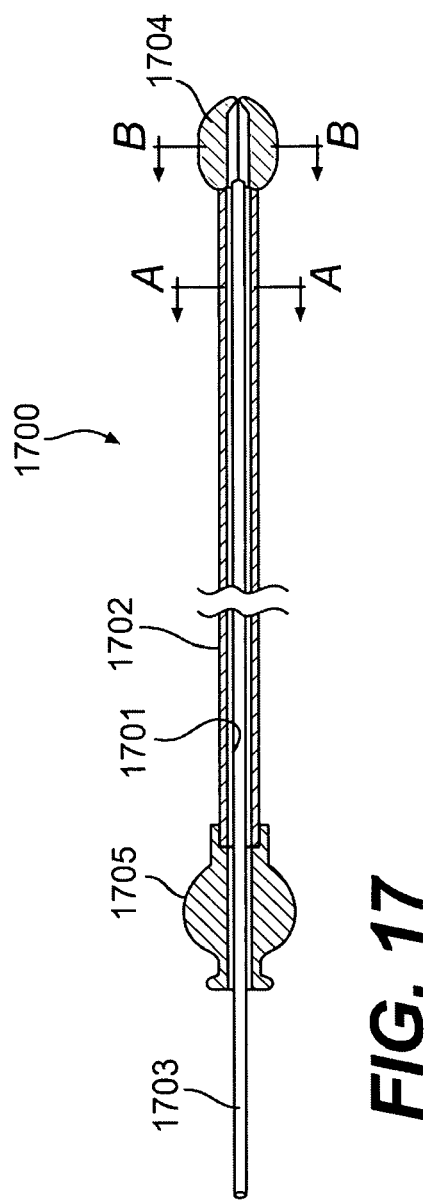
FIG. 17
FIG. 17A SECTION A-A
FIG. 17B SECTION B-B

SECTION A-A

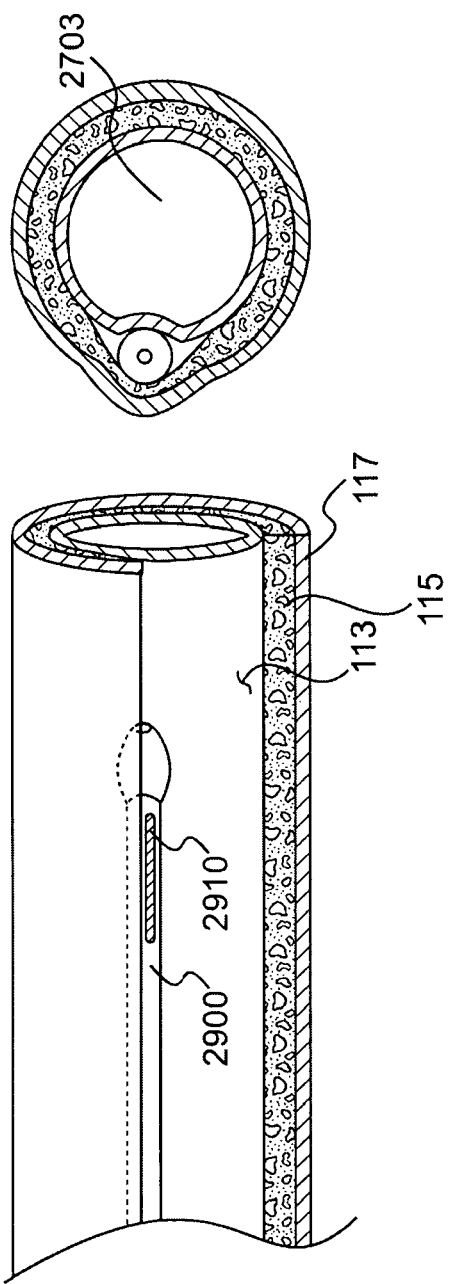

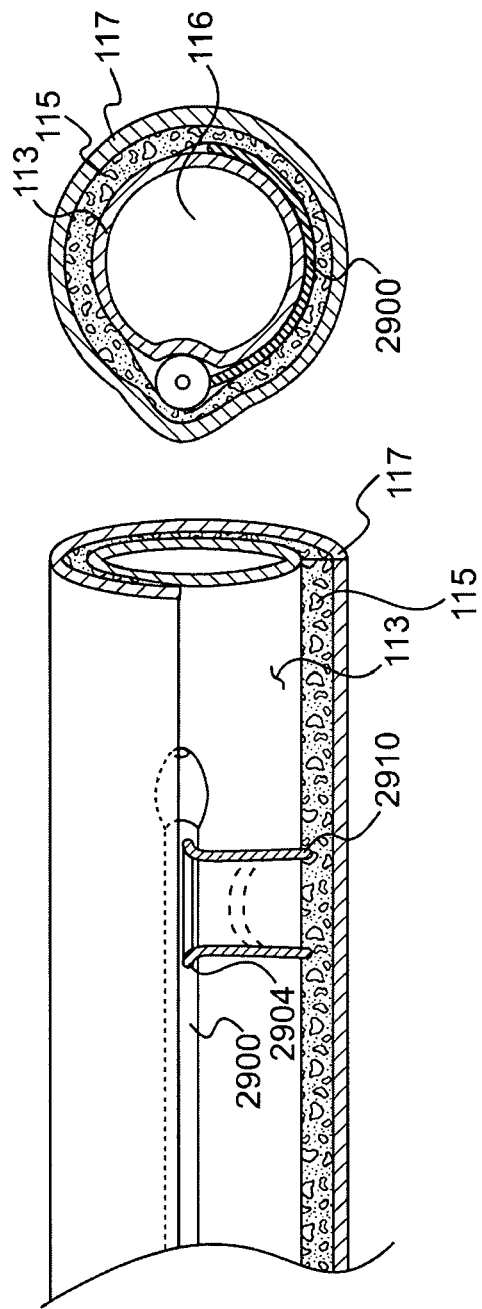

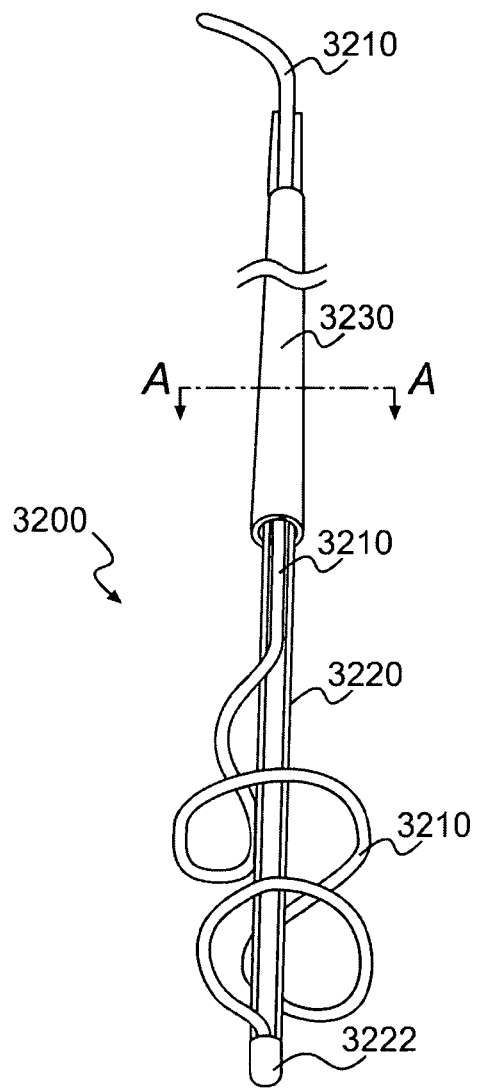
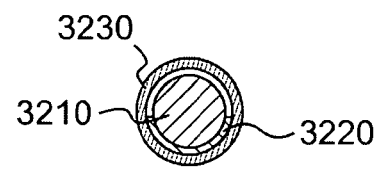
SECTION A-A
FIG. 32B
FIG. 32A

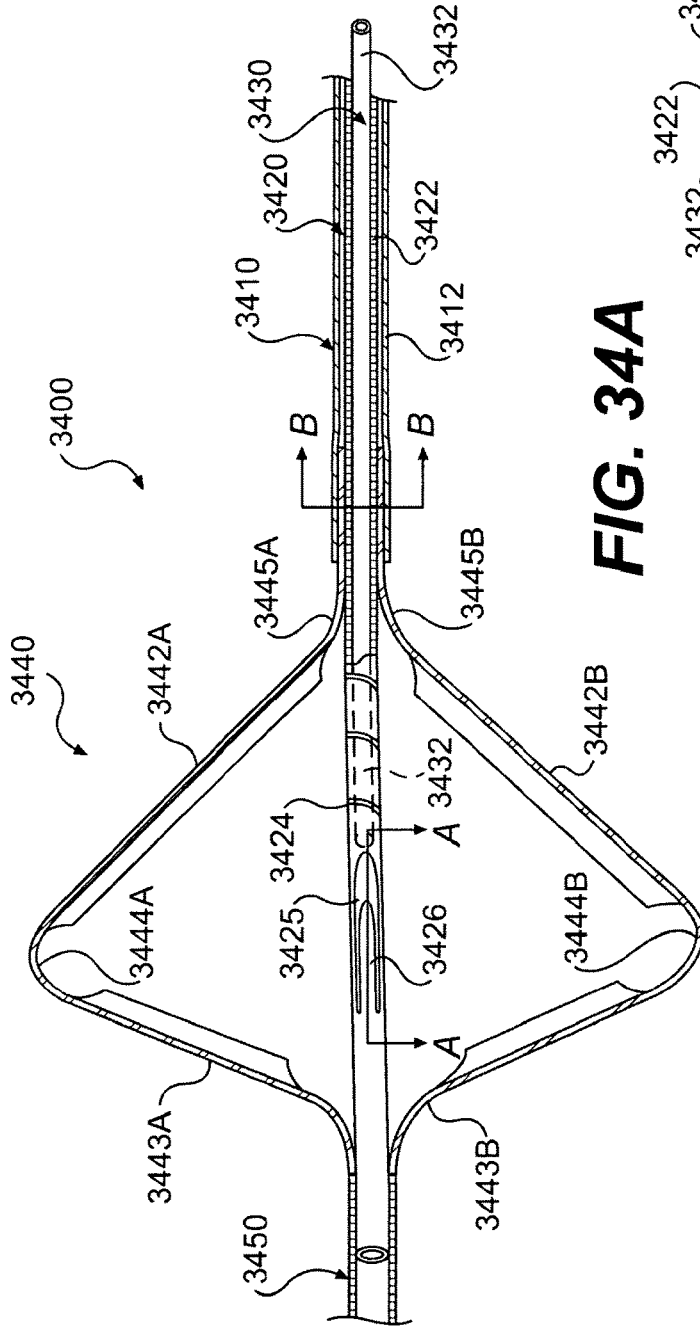
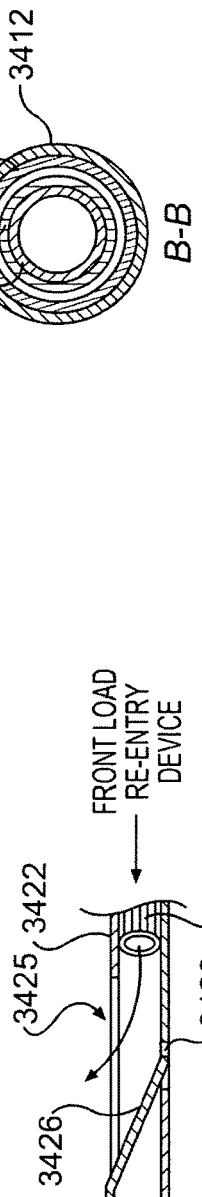
FIG. 34A
FIG. 34B (1) A-A
FIG. 34B (2)

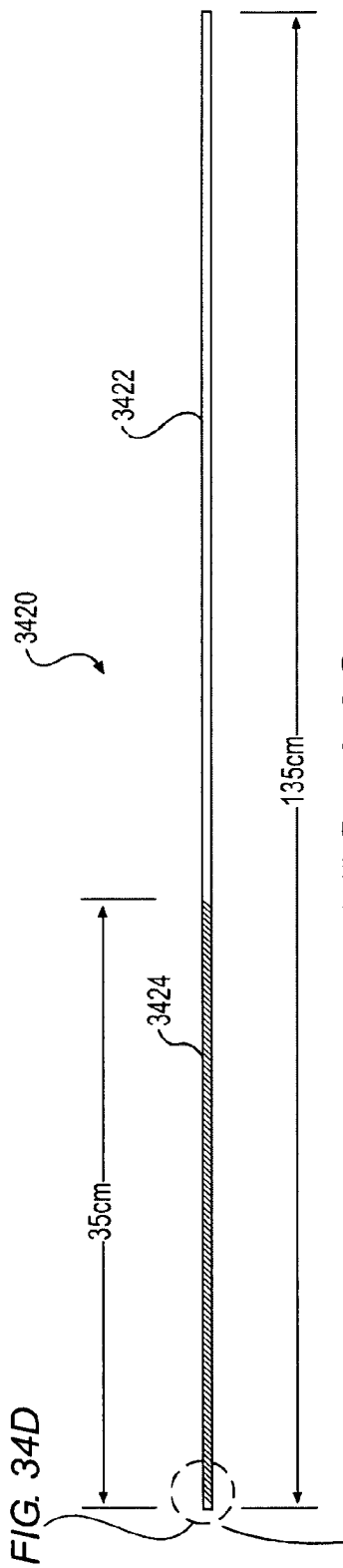
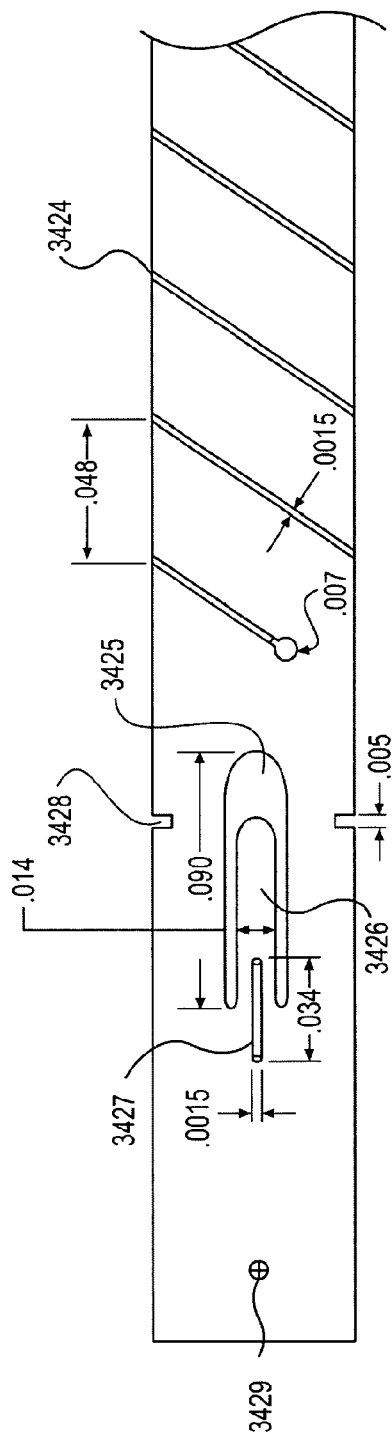
FIG. 34C
FIG. 34D

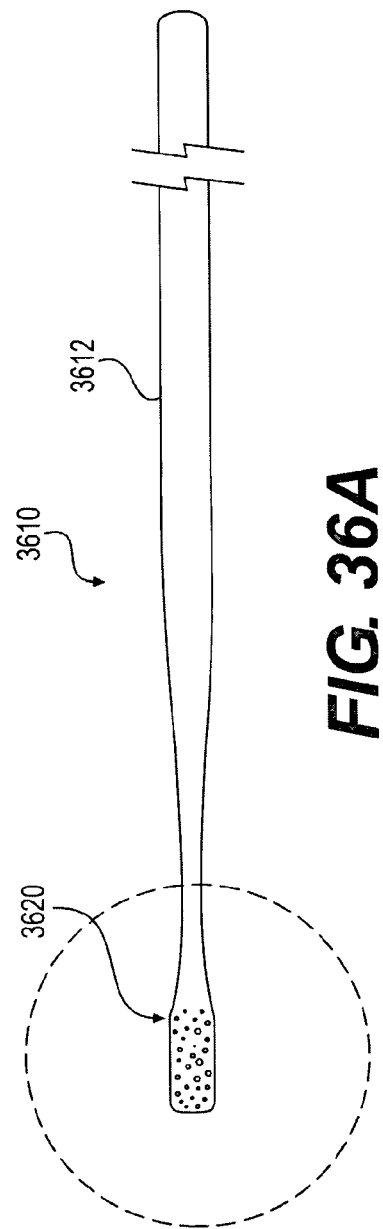
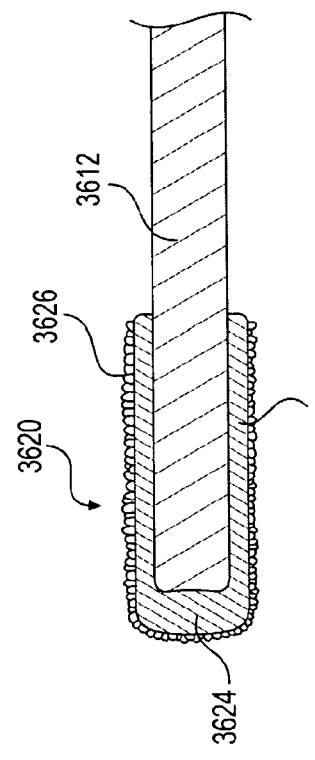

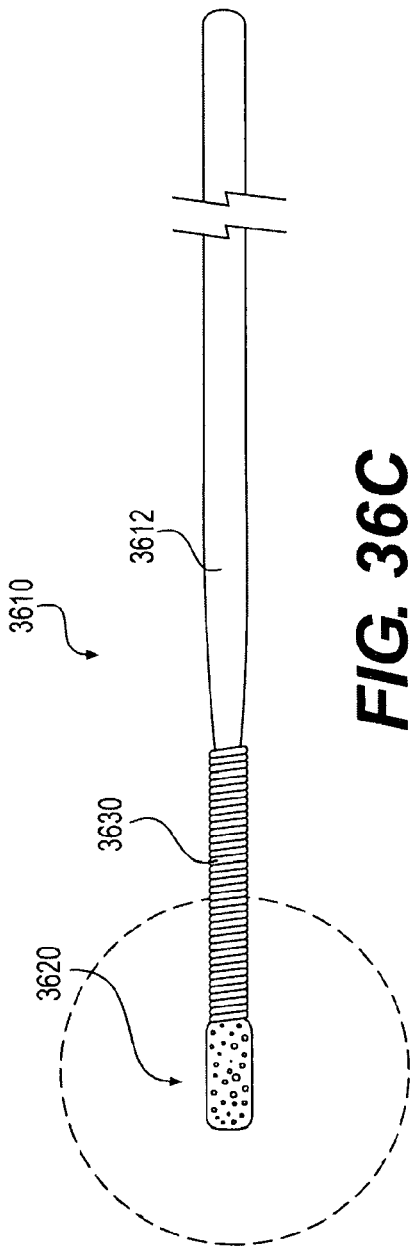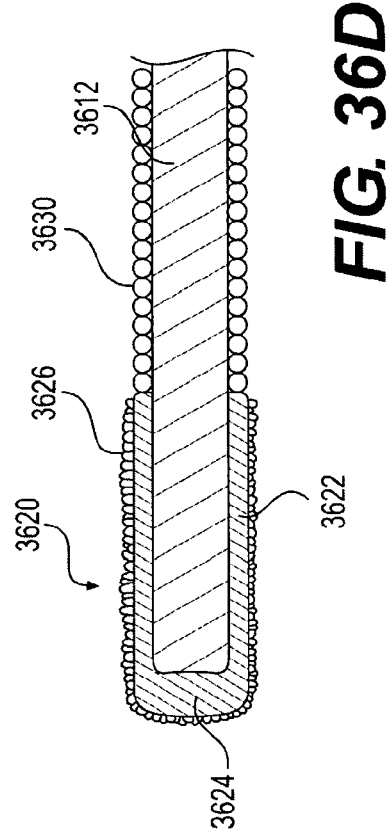

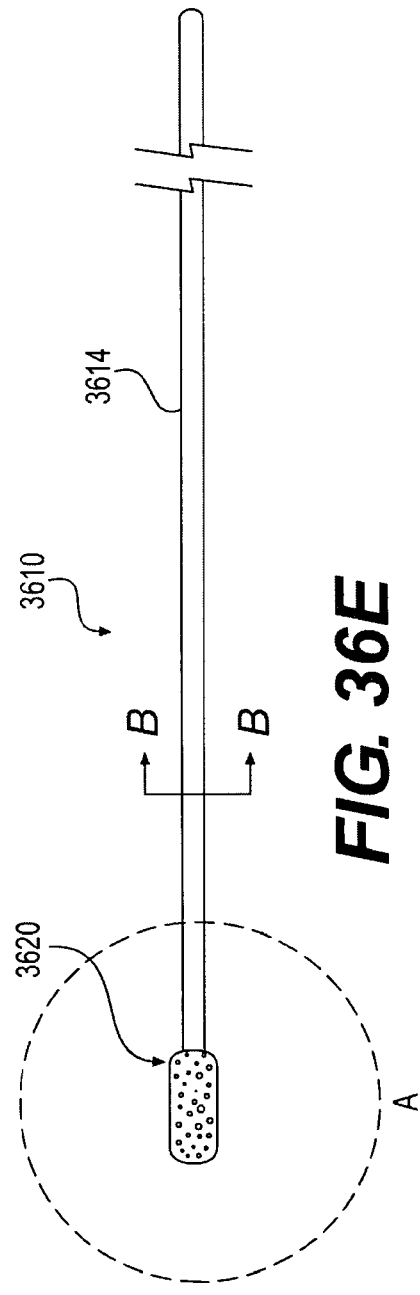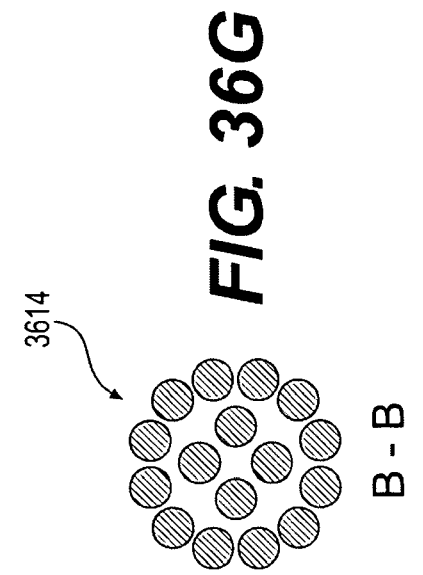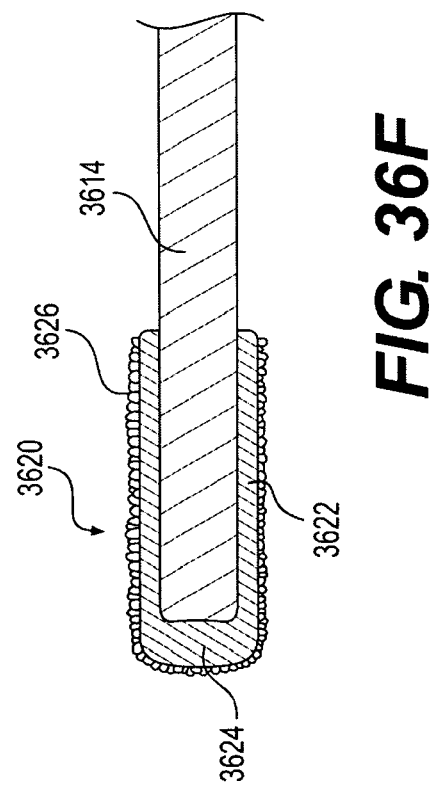

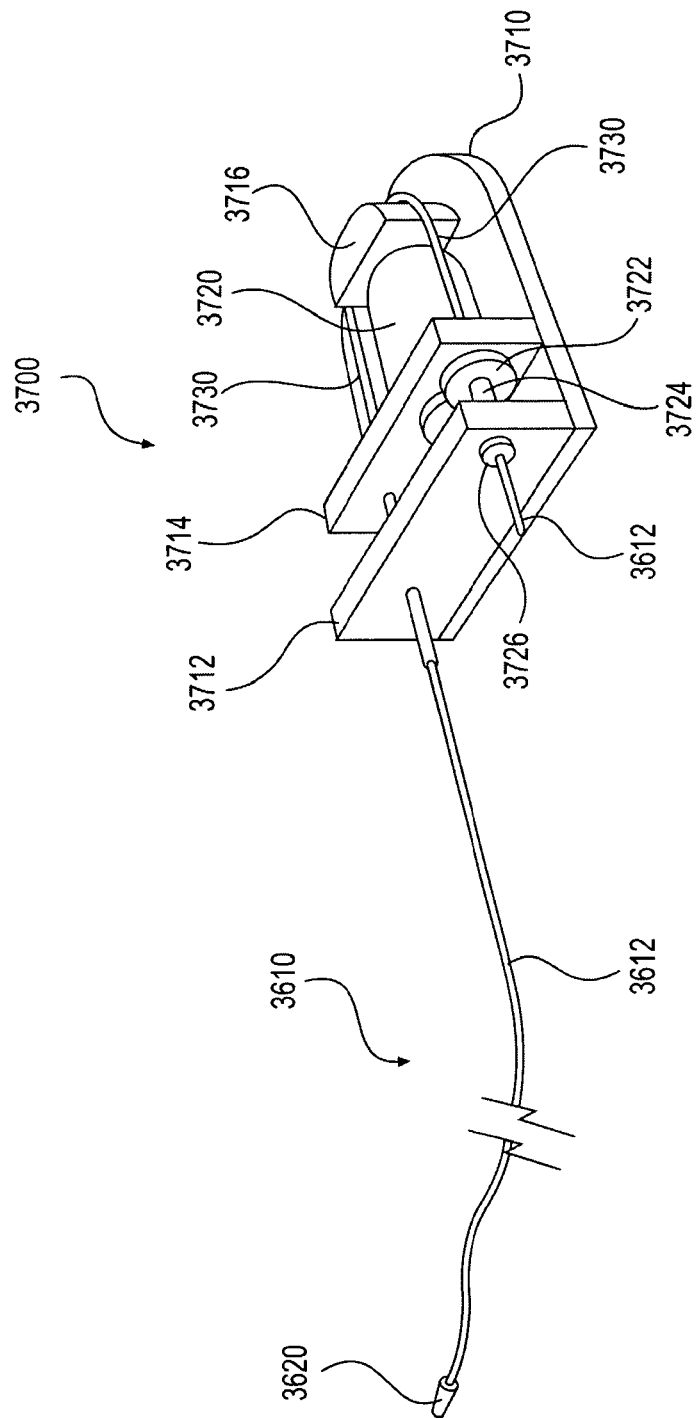

ENDOVASCULAR DEVICES AND METHODS FOR EXPLOITING INTRAMURAL SPACE

CROSS REFERENCE TO RELATED APPLICATIONS

The present application is a continuation application of U.S. patent application Ser. No. 13/660,919, filed Oct. 25, 2012, which is a continuation application of U.S. patent application Ser. No. 11/518,430, filed Sep. 11, 2006, now U.S. Pat. No. 8,323,261, which claims priority to U.S. Provisional Application No. 60/839,782, filed Aug. 24, 2006. In addition, this application also claims the benefit of U.S. Provisional Application No. 60/811,478, filed Jun. 7, 2006. In addition, this application also claims the benefit of U.S. Provisional Application No. 60/727,819, filed Oct. 18, 2005. In additional, this application also claims the benefit of U.S. Provisional Application No. 60/717,726, filed Sep. 15, 2005. In addition, this application also claims the benefit of U.S. Provisional Application No. 60/716,287 filed Sep. 12, 2005, the complete disclosures of which are herein incorporated by reference.

FIELD OF THE INVENTION

The inventions described herein relate to endovascular devices and methods. More particularly, the inventions described herein relate to devices and methods for exploiting intramural (e.g., subintimal) space of a vascular wall to facilitate the treatment of vascular disease. For example, the inventions described herein may be used to cross a chronic total occlusion and facilitate treatment of the occluded vessel by balloon angioplasty, stenting, atherectomy, or other endovascular procedure.

BACKGROUND OF THE INVENTION

Due to age, high cholesterol and other contributing factors, a large percentage of the population has arterial atherosclerosis that totally occludes portions of the patient's vasculature and presents significant risk to the patient's health. For example, in the case of a chronic total occlusion (CTO) of a coronary artery, the result may be painful angina, loss of functional cardiac tissue or death. In another example, complete occlusion of the femoral or popliteal arteries in the leg may result in limb threatening ischemia and limb amputation.

Commonly known endovascular devices and techniques for the treatment of chronic total occlusions (CTOs) are either inefficient (resulting in a time consuming procedure), have a high risk of perforating a vessel (resulting in an unsafe procedure), or fail to cross the occlusion (resulting in poor efficacy). Physicians currently have difficulty visualizing the native vessel lumen, cannot accurately direct endovascular devices toward the visualized lumen, or fail to advance devices through the occlusion. Bypass surgery is often the preferred treatment for patients with chronic total occlusions, but surgical procedures are undesirably invasive.

SUMMARY OF THE INVENTION

To address this and other unmet needs, the present invention provides, in exemplary non-limiting embodiments, devices and methods for exploiting intramural (e.g., subintimal) space of a vascular wall to facilitate the treatment of vascular disease. For example, the devices and methods disclosed herein may be used to (i) visually define the vessel wall boundary; (ii) protect the vessel wall boundary from perforation; (iii) bypass an occlusion; and/or (iv) remove an occlusion. Embodiments are described herein which perform these functions individually as well as collectively. These embodiments may be used in the treatment of a variety of vascular diseases such as chronic total occlusions in the coronary and peripheral arteries, but are not necessarily limited in terms of vascular site or disease state.

The embodiments presented herein are generally described in terms of use in the subintimal space between the intima and media for purposes of illustration, not necessarily limitation. It is contemplated that these embodiments may be used anywhere in the vascular wall (i.e., intramural) or between the vascular wall and an adjacent occlusion. It is also contemplated that these embodiments may operate at one or more intramural locations, and may operate within the outer limits of the vascular wall to avoid perforation out of the wall and into the pericardial space.

In one embodiment, devices and methods are disclosed herein which visually define the vessel wall boundary across an occlusion by placement of a circumferential radiopaque element in the subintimal space. In another embodiment, devices and methods are disclosed herein which protect the vessel wall boundary from perforation by a device passing through an occlusion by placement of a circumferential guard element in the subintimal space. In yet another embodiment, devices and methods are disclosed herein which bypass an occlusion by entering the subintimal space proximal of the occlusion, safely passing through the subintimal space past the occlusion, and re-entering the native lumen distal of the occlusion. Other embodiments exploiting the subintimal space are also disclosed.

BRIEF DESCRIPTION OF THE DRAWINGS

It is to be understood that both the foregoing summary and the following detailed description are exemplary. Together with the following detailed description, the drawings illustrate exemplary embodiments and serve to explain certain principles. In the drawings:

FIG. 1 is a schematic illustration of a heart showing a coronary artery that contains a total occlusion;

FIG. 1A is a detailed view of the coronary artery and total occlusion shown in FIG. 1;

FIG. 1B is a fluoroscopic representation of the view shown in FIG. 1A;

FIG. 4 is a schematic illustration of a device for deploying the subintimal device in a helical pattern;

FIG. 4A is a cross-sectional view taken along line A-A in FIG. 4;

FIG. 4B is a cross-sectional view taken along line B-B in FIG. 4;

FIGS. 8A and 8B schematically illustrate a system that utilizes fluid to achieve atraumatic passage and promote dissection in the subintimal space;

FIGS. 13A-13B schematically illustrate a subintimal device capable of dissection by actuation;

FIGS. 15A and 15B schematically illustrate an embodiment for orienting and reentering the true lumen;

FIGS. 17, 17A and 17B illustrate a subintimal device having a mating or keying feature for torque transmission;

FIGS. 29A-29D illustrate a subintimal device including an accessory subintimal deployable element;

FIGS. 32A-32E illustrate an alternative system for bypassing a total occlusion;

FIGS. 34A-34H schematically illustrate an embodiment using a subintimal crossing device or guide wire to introduce an orienting device;

FIGS. 36A-36G schematically illustrate alternative re-entry device embodiments; and FIG. 37 is a perspective view of a rotary drive unit for the re-entry devices illustrated in FIGS. 36A-36G.

DETAILED DESCRIPTION OF EXEMPLARY EMBODIMENTS

Figure 2:
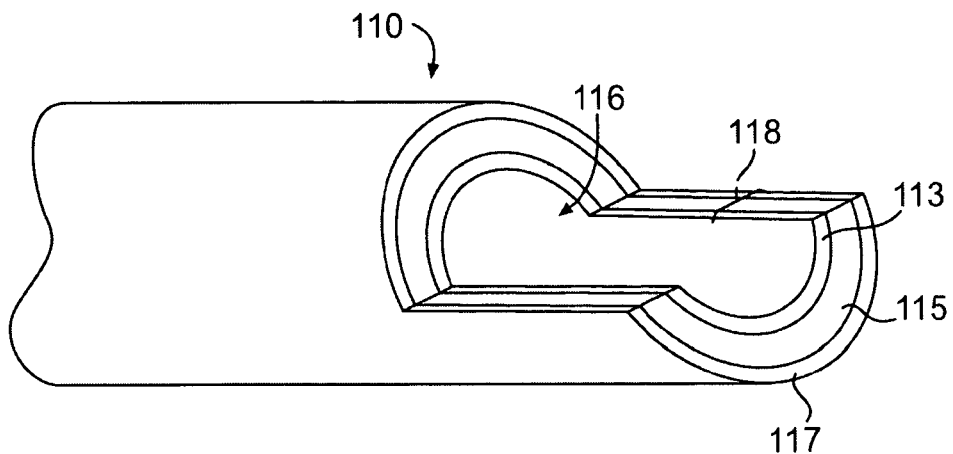
FIG. 2 is a schematic representation of a coronary artery showing the intimal, medial and adventitial layers.

The following detailed description should be read with reference to the drawings in which similar elements in different drawings are numbered the same. The drawings, which are not necessarily to scale, depict illustrative embodiments and are not intended to limit the scope of the invention.

Introduction

Generally, the various embodiments described herein exploit the subintimal space in a vascular wall for purposes of facilitating treatment of vascular disease. In the following detailed description, the embodiments have been organized in terms of their particular function: (i) visually defining the vessel wall boundary; (ii) guarding the vessel wall boundary from perforation; (iii) bypassing an occlusion, and (iv) alternative functions. This organizational approach is used for purposes of illustration and explanation, not for purposes of limitation, as some aspects of some embodiments may be utilized for more than one of the stated functions, and many embodiments have alternative functions not specifically stated or reflected by the organizational titles.

In order to understand the methods by which the embodiments described herein advantageously exploit the subintimal path, it is helpful to first understand the anatomical structures at hand.

Relevant Anatomy

With reference to FIG. 1, a diseased heart 100 is shown schematically. Heart 100 includes a plurality of coronary arteries 110, all of which are susceptible to occlusion. Under certain physiological circumstances and given sufficient time, some occlusions may become total or complete, such as total occlusion 120.

As used herein, the terms total occlusion and complete occlusion are intended to refer to the same or similar degree of occlusion with some possible variation in the age of the occlusion. Generally, a total occlusion refers to a vascular lumen that is 90% or more functionally occluded in cross-sectional area, rendering it with little to no blood flow therethrough and making it difficult or impossible to pass a conventional guide wire therethrough. Also generally, the older the total occlusion the more organized the occlusive material will be and the more fibrous and calcified it will become. According to one accepted clinical definition, a total occlusion is considered chronic if it is greater than two (2) weeks old from symptom onset.

With reference to FIG. 1A, a magnified view of total occlusion 120 within coronary artery 110 is shown schematically. Generally, the proximal portion 112 of artery 110 (i.e., the portion of artery 110 proximal of total occlusion 120) may be easily accessed using endovascular devices and has adequate blood flow to supply the surrounding cardiac muscle. The distal portion 114 of artery 110 (i.e., the portion of artery 110 distal of total occlusion 120) is not easily accessed with interventional devices and has significantly reduced blood flow as compared to proximal portion 112.

A commonly performed diagnostic procedure called an angiogram involves the infusion of a radiopaque fluid into the arterial bloodstream through a percutaneously placed angiography catheter. Using an x-ray fluoroscope, two-dimensional images of the arterial pathways may be obtained and recorded. FIG. 1B shows a schematic example of an angiographic image of a chronic total occlusion 120. It is common that the angiogram allows a physician to visualize the proximal segment 112 but does not allow visualization of the occlusion 120 or the distal segment 114.

With reference to FIG. 2, a cut-away segment of coronary artery 110 is shown schematically. Coronary artery 110 includes a true or native lumen 116 defined by arterial wall 118. The innermost layer of arterial wall 118 is called the intima or intimal layer 113 (for sake of clarity, the multi layer intima is shown as a single homogenous layer). Concentrically outward of the intima is the media or medial layer 115 (which also is comprised of more than one layer but is shown as a single homogenous layer). The outermost layer of the artery is the adventitia 117. The transition between the outermost portion of the intima and the innermost portion of the media is referred to as the subintimal space, which may be delaminated to increase the space therebetween. The subintimal space is sometimes referred to as a false lumen, in contrast to true lumen 116.

Visualization & Perforation Guard Embodiments

As may be appreciated from FIG. 1B, a total occlusion 120 prevents the occlusion and distal arterial segment 114 from being visualized using radiopaque contrast media injection fluoroscopy. In some instances, sufficient contrast media may pass through collaterals around the total occlusion 120 to achieve visualization of the distal segment 114, but visualization of the distal segment 114 is often unclear and visualization of the occluded segment 120 is still not achieved. In some rare instances, sufficient radiopaque contrast may be injected retrograde through the venous system to achieve a fluoroscopic image of the distal segment 114, but such images are often hazy and still do not illuminate the occluded segment 120.

Figure 3A:
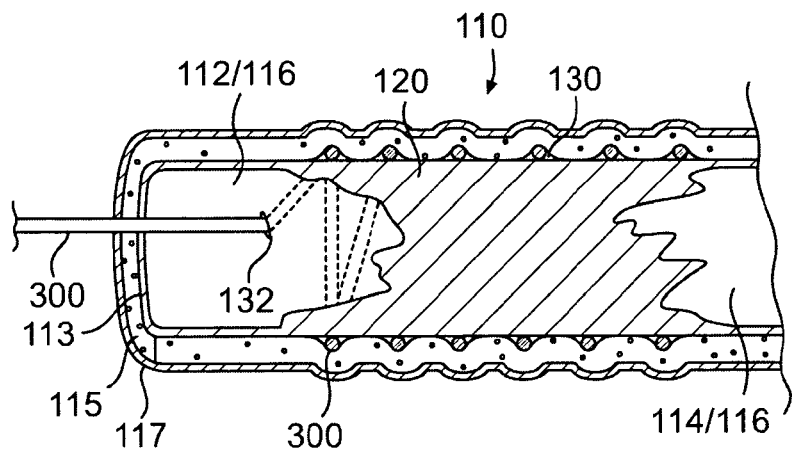
FIG. 3A is a longitudinal cross-section of an artery with a total occlusion showing a device deployed in the subintimal space.

To achieve visualization of the occluded segment 120 and the distal segment 114, a radiopaque subintimal device 300 may be introduced into the subintimal space as shown in FIG. 3A. In this illustration, subintimal device 300 is intended to be relatively generic, as a variety of subintimal devices may be employed as will be described in more detail hereinafter. The subintimal device 300 exits the true lumen 116 and enters the subintimal space 130 at entry point 132 proximal of the total occlusion 120 somewhere in the proximal segment 112. Within the subintimal space 130, the sub-intimal device 300 may extend across and beyond the total occlusion 120 and into the distal segment 114. With the subintimal device positioned as shown in FIG. 3A, and due to the radiopaque nature of the subintimal device 300, the occluded segment 120 and distal segment 114 may be fluoroscopically visualized as shown in FIG. 3B.

Thus, subintimal device 300 may be used to enhance arterial visualization by placement within the subintimal space 130 concentrically around the total occlusion 120. The subintimal device 300 defines the approximate inside diameter of the artery 110 and also defines axial bends or tortuosity in the vessel 110 across the occluded segment 120 and distal segment 114, thereby defining the circumferential boundary of the artery 110 across the occluded segment 120 and distal segment 114. Also, by placement within the subintimal space 130 concentrically around the total occlusion 120, the subintimal device 300 may be used to protect or guard the wall 118 of the artery 110 from perforation of devices that attempt to penetrate the total occlusion 120 via the true lumen 116.

Figure 3B:
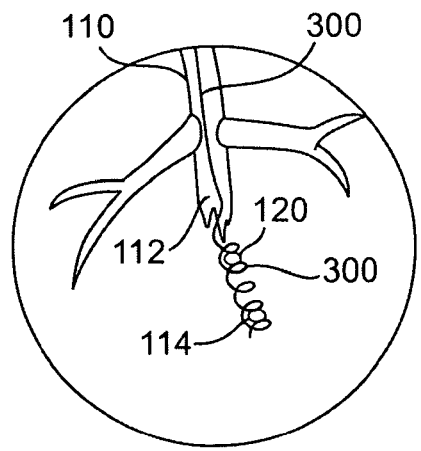
FIG. 3B is a fluoroscopic representation of the deployed subintimal device.

As shown in FIGS. 3A and 3B, the subintimal device 300 is deployed in a helical pattern within the subintimal space 130. The helical pattern is shown for purposes of illustration, not limitation, as other patterns may be employed as well. Various other deployment patterns are described in more detail hereinafter, but the helical pattern is used herein to further illustrate the concept.

Figure 5:
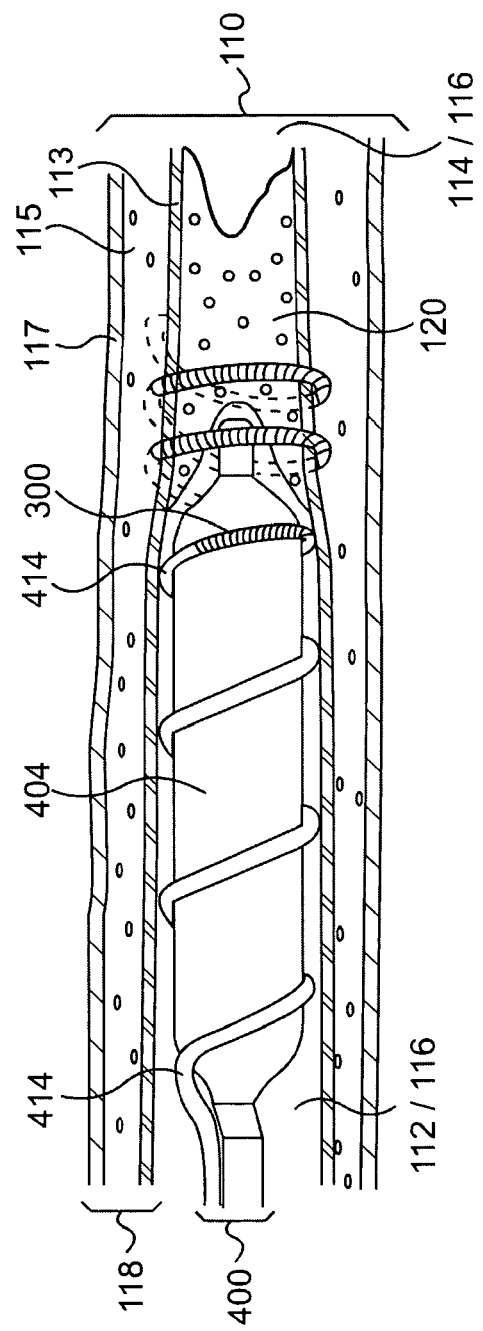
FIG. 5 is a longitudinal cross-section of an artery with a total occlusion showing a delivery device deploying a subintimal device in a helical pattern within the subintimal space.

With reference to FIGS. 4, 4A and 4B, a deployment device 400 is shown schematically. Deployment device 400 may be used to direct the subintimal device 300 into the subintimal space 130 at entry point 132 and deploy the subintimal device 300 in a helical pattern therein as shown in FIG. 5. The deployment device 400 may take the form of a balloon catheter including catheter shaft 402 and distal balloon 404. Catheter shaft 402 includes an outer tube 406 and an inner tube 408 defining an inflation lumen 410 therebetween for inflation of balloon 404. The inner wire tube 408 defines a guide wire lumen 412 therein for advancement of the device 400 over a guide wire (not shown). A delivery tube 414 extends along the outer tube 406 and around the balloon 404 in a helical (or other) pattern. The delivery tube 414 defines a delivery lumen 416 therein for advancement of the subintimal device therethrough. In this particular embodiment, the subintimal device 300 may have a straight configuration in its relaxed state and rely on the helical delivery tube 414 to achieve the desired helical pattern.

With reference to FIG. 5, the delivery device 400 is shown in position just proximal of the total occlusion 120. In this position, the balloon 404 may be inflated within the vessel lumen 116 to direct the delivery tube 414 toward the vessel wall 118 at an orientation for the subintimal device 300 to penetrate through the intima 113 at an entry point and into the subintimal space. By virtue of the helical delivery tube 414, the subintimal device 300 is sent on a helical trajectory as it is advanced through delivery tube 414 resulting in deployment of the subintimal device 300 in a helical pattern. As shown, the subintimal device 300 has been advanced through the delivery tube 414 and positioned concentrically outside the total occlusion 120, outside the intimal layer 113, and inside the medial layer 115 in the subintimal space.

Figure 6:
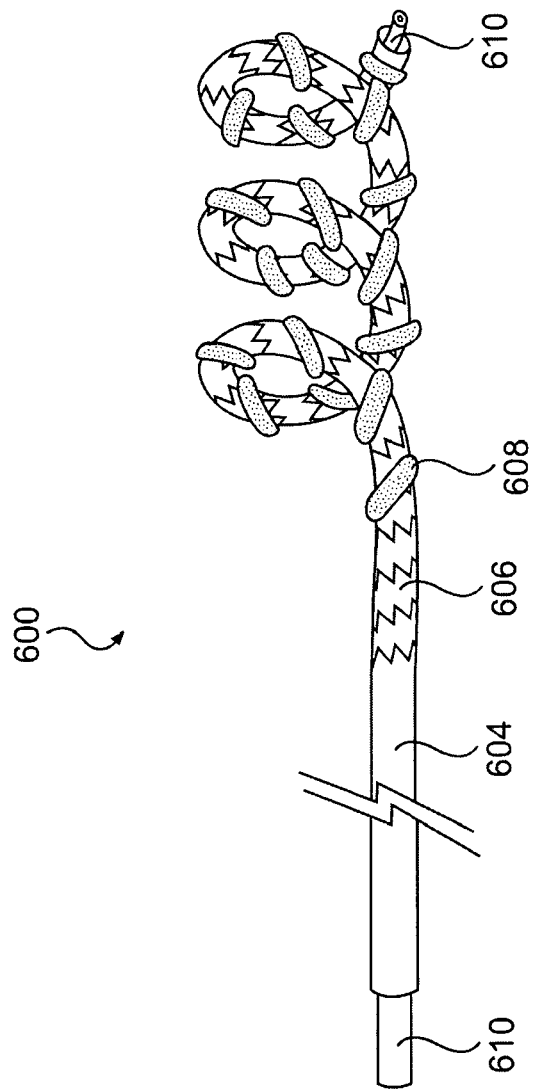
FIG. 6 is a schematic illustration of an alternative subintimal device that may assume a helical pattern itself.

With reference to FIG. 6, an alternative approach to achieving a helical pattern in the subintimal space is shown. Whereas the delivery device 400 described previously provided a helical delivery tube to deliver a subintimal device 300 that had a straight configuration in its relaxed state, FIG. 6 schematically illustrates an alternative subintimal device 600 that may assume a helical shape itself. Subintimal device 600 includes an elongate tubular shaft 604, at least a distal portion of which includes a helical interlocking gear 606 and a helical wire coil 608 disposed thereon. A helically shaped inner mandrel or tube 610 may be disposed in the tubular shaft 604 such that the shaft 604 rotates freely thereon. The shaft 604 may have a linear or straight configuration in a relaxed state and a helical configuration (shown) when the helically shaped inner member 610 is disposed therein. The device 600 may be disposed in a constraining sheath (not shown) and navigated to the intravascular site, such as the site of a total occlusion. When the device 600 is advanced distally out the end of the constraining sheath or when the sheath is pulled proximally relative thereto, the distal portion of the device 600 assumes a helical shape as shown. The shaft 604 may be rotated relative to the inner member 610 to cause rotation of the helical wire threads 608, which may be used to engage the vessel wall and advance around the total occlusion in the subintimal path. A bearing (not shown) may be disposed on the inner member 610 to engage the proximal or distal end of the shaft 604 to enable the shaft 604 and the inner member 610 to be advanced in unison. Subintimal device 600 may include any of the variants described hereinafter, such as various gear shaft configurations, distal atraumatic tip configurations, fluidic dissection mechanisms, etc.

Figure 7A:
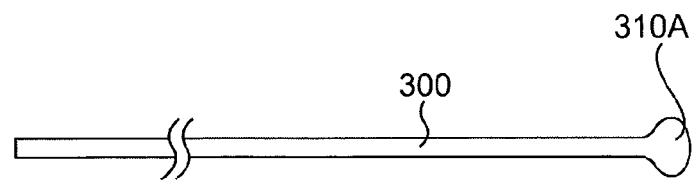
FIGS. 7A-7D schematically illustrate alternative subintimal device embodiments.
Figure 7B:
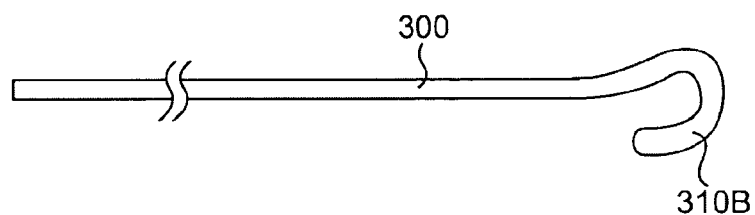
Figure 7C:
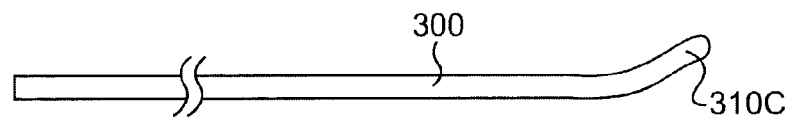

Generally, the subintimal devices described herein are designed for intravascular navigation and atraumatic subintimal passage. The subintimal devices 300 may be constructed similar to a guide wire and may include elements to atraumatically pass through the subintimal space. Such atraumatic elements may be employed to minimize damage to arterial wall and to minimize the likelihood of perforation therethrough. Examples of such atraumatic elements 310 are schematically illustrated in FIGS. 7A-7C. The subintimal device may include a ball-shaped tip 310A as shown In FIG. 7A, a hook-shaped or loop-shaped tip 310B as shown in FIG. 7B, and/or a bent tip 310C as shown in FIG. 7C. These atraumatic elements distribute axial forces over larger areas of tissue and thereby reduce the chance of vessel perforation. An additional aspect of the bent tip 310C is ability to torsionally direct the tip and control the path of the device through the subintimal space. The ball tip 310A may be formed from a suitable metallic material including but not limited to stainless steel, silver solder, or braze. The ball tip 310A may also be formed from suitable polymeric materials or adhesives including but not limited to polycarbonate, polyethylene or epoxy. Note that the ball tip 310A may be bulbous and larger than the shaft proximal thereto. The loop tip 310B and bent tip 310C may be created during the manufacturing process (for example by heat setting or mechanical deformation) or the tip may be shaped (for example by mechanical deformation) by the physician.

Figure 7D:
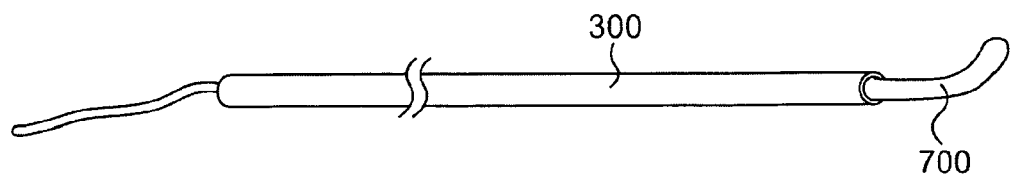

As an alternative or in addition to the atraumatic tip elements 310 as described above, the subintimal device 300 may use a guide wire 700 to facilitate atraumatic passage as shown in FIG. 7D. In this embodiment, the subintimal device 300 may include a lumen extending therethrough such that the device 300 may be advanced over the guide wire 700. In this embodiment, the body of the subintimal device 300 has a hollow internal diameter defining a guide wire lumen therein. The guide wire lumen extends from a proximal opening to a distal opening and is sized to accept a guide wire 700 therethrough. The guide wire 700 provides an atraumatic element at its distal end and also provides a mechanism for rotationally steering the subintimal device 300 through the subintimal space. The guide wire 700 may be pushed forward by the subintimal device through a bearing element (not shown) at the proximal or distal end of the subintimal device. The bearing element may provide interference in the axial direction while allowing for relative rotation between the subintimal device and guide wire. An example of a bearing element may be a collar crimped to the distal end of the guide wire with an outside diameter larger in dimension than the guide wire lumen within the subintimal device.

Other techniques may be employed to facilitate atraumatic passage through the subintimal space. For example, pressurized fluid may be used to facilitate atraumatic passage and even promote atraumatic dissection of the layers defining the subintimal space. FIGS. 8A and 8B schematically illustrate a system 800 that utilizes fluid to achieve atraumatic passage and promote dissection. System 800 includes a subintimal device 810 and associated pumping system 820. The fluidic system 800 is similar in certain aspects to the arrangements described elsewhere herein, the various aspects of which may be combined or used in the alternative as will be appreciated by those skilled in the art. System 800 includes a subintimal device 810 which may comprise any of the tubular subintimal devices described herein. Generally, subintimal device 810 includes a tubular shaft 812 having a proximal end connected to a pumping mechanism 820. A plunger rod 814 is slidably disposed in the tubular shaft 812 as shown in FIG. 8B and its proximal end is connected to a linear actuator 822 of the pumping mechanism as shown in FIG. 8A. The rod 814 extends through the tubular shaft 812 to a point proximal of the distal end thereof to define a pumping chamber 816. A source of liquid 830 (e.g., saline bag) is connected to the proximal end of the subintimal device 810 via a fluid line 832 and optional valve 834 to supply liquid to the annular lumen between the rod 814 and the inner wall of the tubular shaft 812. As the linear actuator moves the rod 814 back and forth in the tubular shaft 812, liquid is caused to be expelled out of the chamber 816 in a pulsatile fashion, which may be used to hydraulically dissect tissues to define a subintimal path as described previously, for example. Optionally, a balloon may be disposed on the distal end of the device such that it is cyclically inflated and deflated with the pulsatile flow to cause controlled dissection. The stroke length, stroke rate and stroke volume may be adjusted to achieve the desired effect. For example, the stroke volume of the chamber 816 may be relatively small (0.01 cc-1.0 cc, for example) such that liquid exits the chamber 816 with high energy that dissipates quickly to minimize trauma to tissues as they are dissected. One example is a stroke volume of 0.25 cc and a stroke rate of 10 Hz which has been found to facilitate atraumatic passage and even promote atraumatic dissection in a bench-top model using animal tissues.

Another technique to facilitate or supplement atraumatic passage of the subintimal device is to reduce friction between the device and the surrounding tissues. The fluidic embodiment described above benefits from this technique in that saline acts to reduce friction. Friction may also be reduced by using coatings (e.g., PTFE, hydrophilic materials, etc.) which may be applied to the external surface of the subintimal device. Friction may also be reduced by taking advantage of the fact that the kinetic coefficient of friction is usually less than the static coefficient of friction for a given frictional interface. As applied to the subintimal devices described herein, the lower kinetic coefficient of friction may be utilized by rotating the device back and forth between tissues in the subintimal space. Such reciprocal rotational motion may be applied manually by rolling the proximal end of the device between the user's thumb and forefinger, or may be applied automatically using a reciprocal motor drive, for example.

Figure 9A:
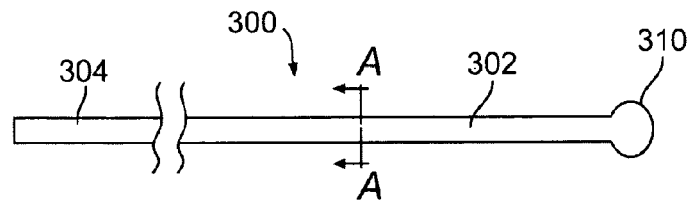
FIGS. 9A-9J schematically illustrate various embodiments of torsionally rigid yet flexible designs for a subintimal device.

Whether it is to reduce friction, to facilitate steering, or to facilitate advancement, it may be desirable to incorporate enhanced torsional characteristics in the body 302 of the subintimal device 300 as schematically shown in FIGS. 9A-9F. Generally, it is desirable to maintain flexibility of at least a distal portion of the body 302 to avoid compromising intravascular navigation in tortuous pathways. FIG. 9A schematically shows a generic subintimal device 300 with a distal body portion 302 and a proximal body portion 304. Relative to the proximal body portion 304, the distal body portion may be more flexible since it will frequently encounter a tortuous pathway. The proximal body portion may only encounter minimal bends in a guide catheter or the like, and therefore may be made more stiff yet torsionally rigid as with a metal tube (e.g., stainless steel hypotube).

Figure 9B:
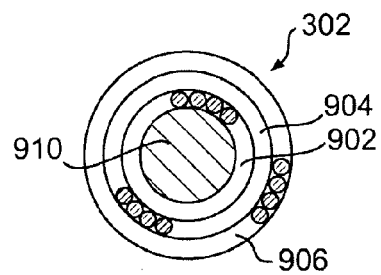
Figure 9D:
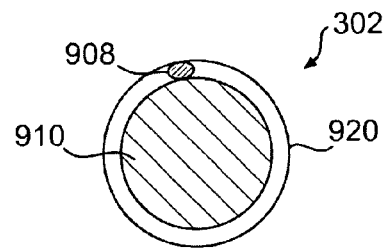
Figure 9C:
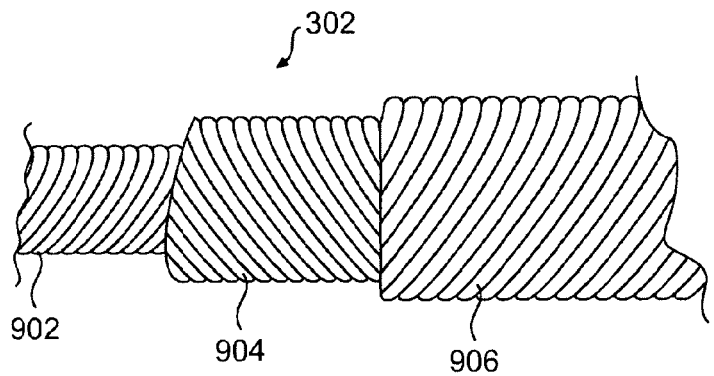

One example of a flexible yet torsionally rigid distal body 302 design is shown in FIGS. 9B and 9C. In this embodiment, distal body portion 302 is made of a multitude of independent coils 902, 904, 906 concentrically wound in opposing directions. These coils can diametrically interact (for example internal coil diametrically expands while the external coil diametrically contracts) with an applied torque. This interaction can provide torsional strength while maintaining axial flexibility. The core of the distal body 302 may be hollow or may contain a fixed wire 910 within its internal lumen. The fixed wire 910 may provide an increase in axial and/or torsional stiffness, and may also have a tapering cross-section to increase flexibility in the distal direction. A hollow core may be used for insertion of a guide wire. Coils 902, 904, 906 and core wire 910 may be made of suitable metallic or polymeric materials including but not limited to stainless steel, nickel titanium, platinum or ultra high molecular weight polyethylene.

Figure 9E:
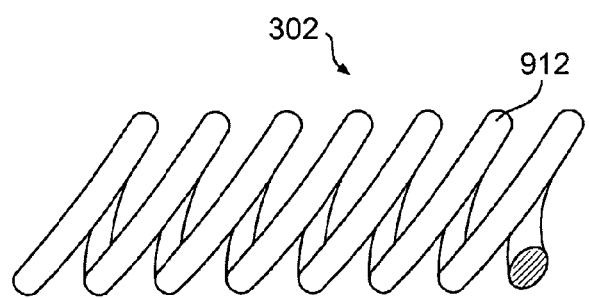
Figure 9F:
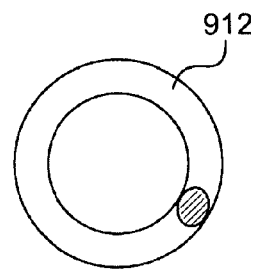

Another example of a flexible yet torsionally rigid distal body 302 design is shown in FIG. 9D wherein a single coil 908 is wound over an internal core 910 surrounded by a thin polymeric sheath 920. Yet another example of a flexible yet torsionally rigid distal body 302 design is shown in FIGS. 9E and 9F wherein the body simply comprises a single open wound coil 912.

Figure 9G:
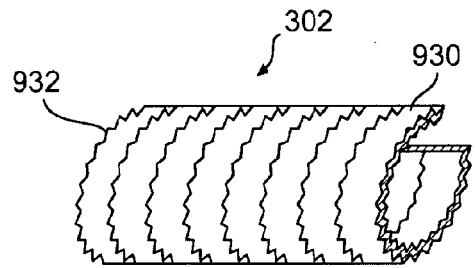

A further example of a flexible yet torsionally rigid distal body 302 design is shown in FIG. 9G. The distal body 302 may be constructed in part or in to total of a single layer coil with geometric features along the coil length that allow adjacent coils to engage (for example mechanical engagement similar to the teeth of a gear). FIG. 9G shows coil 930 closely wound with a multitude of teeth 932 along the coil edges in contact such that the peaks of one coil falls within the valleys of the adjacent coil. A conventional coil (without teeth) reacts to an applied torsional load by diametrically expanding or contracting, thus forcing the wire surfaces within a turn of the coil to translate with respect to its neighboring turn. The construction of coil 930 resists the translation of wire surfaces within the coil thus resisting the diametric expansion or contraction (coil deformation). An increased resistance to coil deformation increases the torsional resistance of the device body while the coiled construction provides axial flexibility.

Figure 9H:
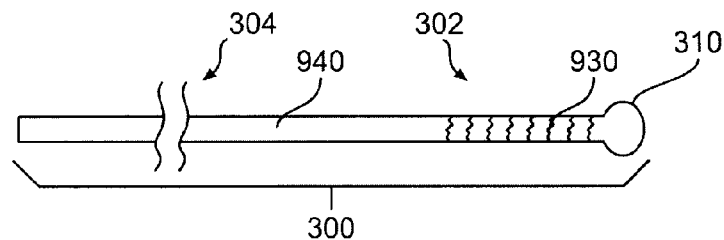

This design may be implemented in manner shown in FIG. 9H. The subintimal device 300 includes a proximal body portion 304 that is formed of a continuous solid metallic tube 940 and a distal body portion 302 that is formed of the same tube with a laser cut coil segment 930, wherein the pattern of the laser cut defines the teeth 932. Suitable materials for the metallic tube include but are not limited to stainless steel and nickel titanium. Alternatively, the coil 930 may be wound from a continuous wire. The wire may have a cross section that for example has been mechanically deformed (stamped) to form the teeth 932 and allow coil engagement.

Figure 9I:
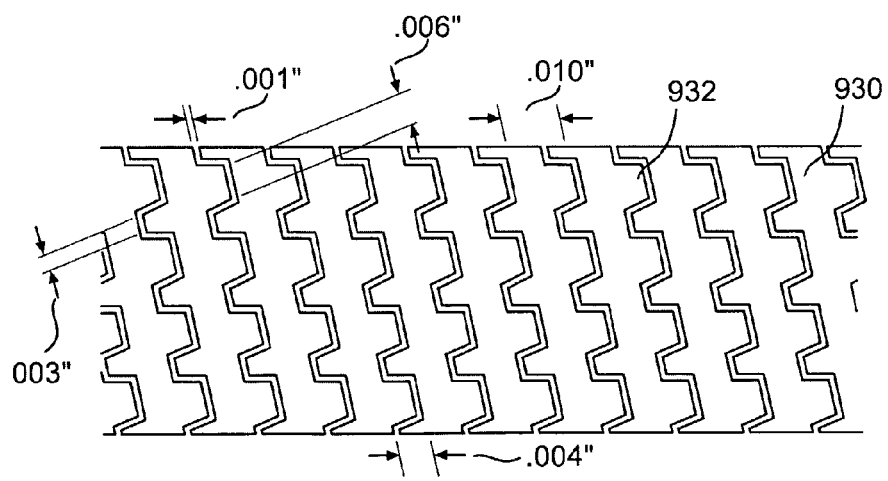
Figure 9J:
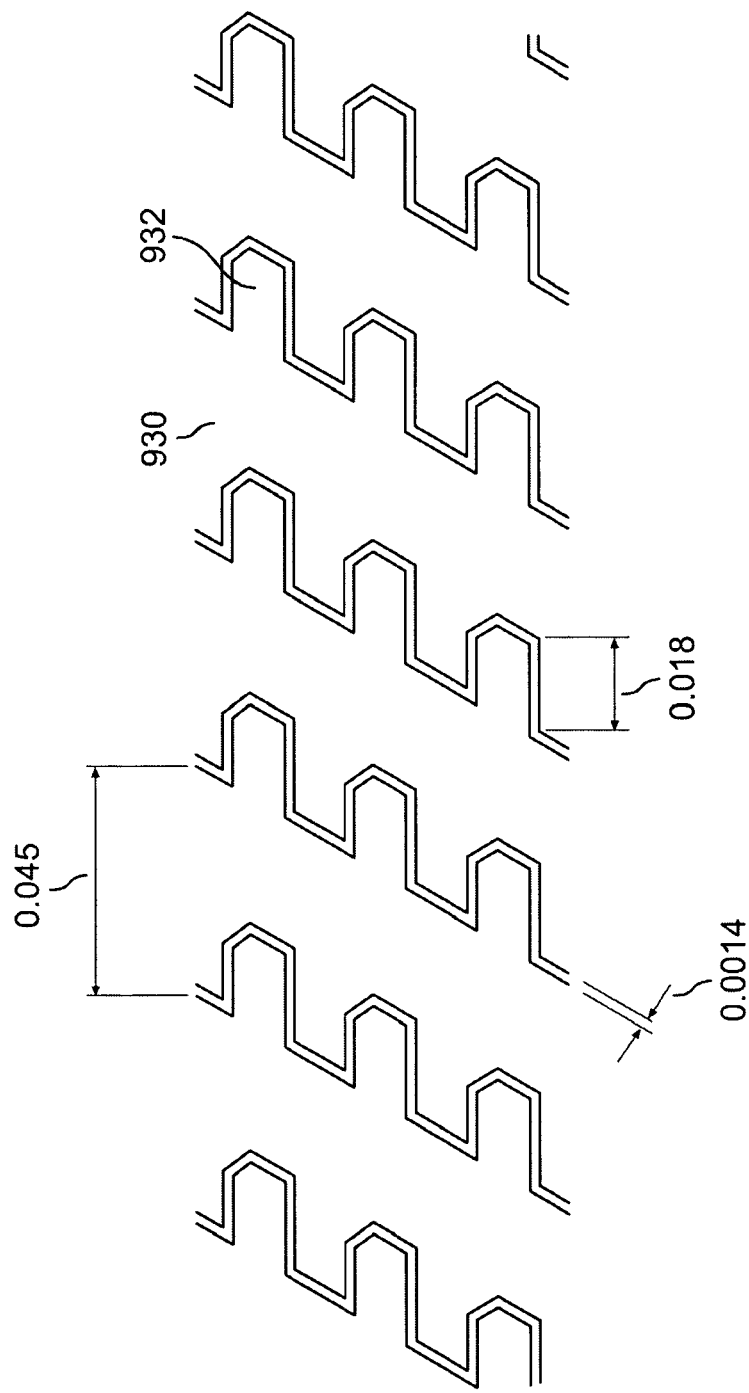

FIG. 9I shows one example of a laser cut pattern from the circumference of a tube that has been shown in a flat configuration for purposes of illustration. In the pattern shown in FIG. 9I, the teeth 932 are generally trapezoidal and extend orthogonal to the coil turns 930. FIG. 9J shows an alternative pattern wherein the teeth are generally rectangular (with a clipped corner) with a major (longer) length extending parallel to the axis of the body. The parallel orientation and longer length of the teeth 932 shown in FIG. 9J promote engagement and reduce slippage of adjacent coil turns 930.

Figure 10A:
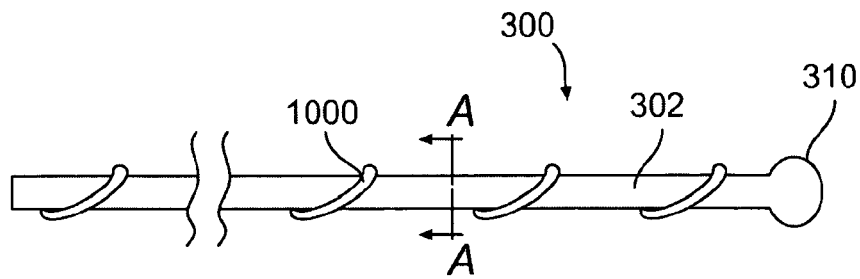
FIGS. 10A-10D schematically illustrate various embodiments of threaded designs for a subintimal device.
Figure 10B:
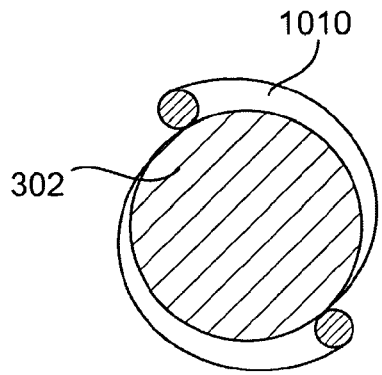
Figure 10D:
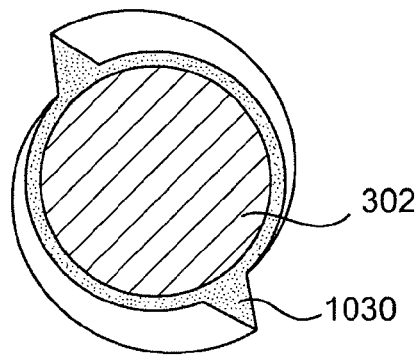
Figure 10C:
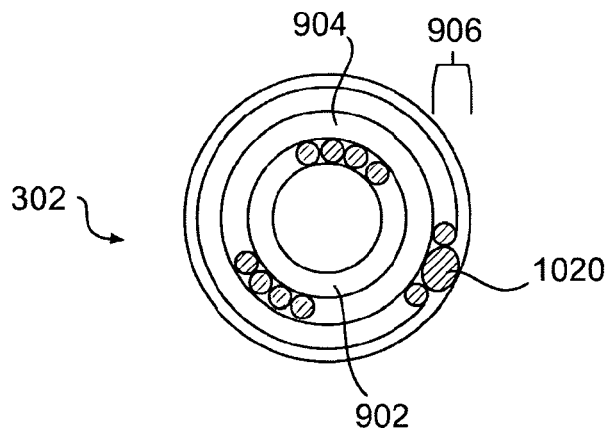

As mentioned previously, another application of a flexible yet torsionally rigid subintimal device is to facilitate advancement through the subintimal space using threads that rotationally engage vascular tissues similar to a threaded screw. FIG. 10A shows a subintimal device 300 wherein at least the distal body portion 302 includes threads 1000 on the exterior surface thereof. The threads 1000 act like an external corkscrew that has the ability to rotationally engage the arterial tissues and help drive the subintimal device 300 through the subintimal space. FIGS. 10B-10D are cross-sectional views taken along line A-A in FIG. 10A and show various alternative embodiments for the threads 1000. FIG. 10B shows one or more round corkscrew members 1010 that are concentrically wound on the outside of the distal body 302. FIG. 10C shows a multi-layer coil construction with coil layers 902, 904, 906 where corkscrew member 1020 comprises a wire element of larger cross sectional area wound within the external concentric coil 906. The corkscrew members may have a rounded shape as shown in FIGS. 10B and 10C, or other shape such as triangular, square, or other cross-sectional shape that may aid in tissue engagement and subintimal device advancement. FIG. 10D shows a polymer tube with a corkscrew profile 1030 formed therein and concentrically positioned around distal body portion 302. In each of these embodiments, withdrawal of the subintimal device 300 may be achieved by rotating the device in the opposite direction thus driving the device back out of the subintimal space.

In some instances, it may be desirable to utilize an over-the-wire type subintimal device to facilitate advancement into and through the subintimal space. In addition to the embodiments described previously, FIGS. 11A-11C illustrate additional over-the-wire type embodiments of subintimal devices. These embodiments may also be used to facilitate guide wire advancement through a total occlusion, such as when it is desirable to stay in the true lumen.

Figure 11A:
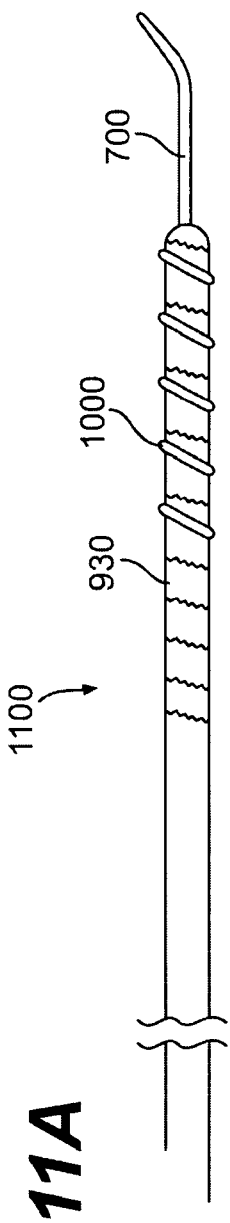
FIGS. 11A-11C schematically illustrate various over-the-wire embodiments for a subintimal device.
Figure 11B:
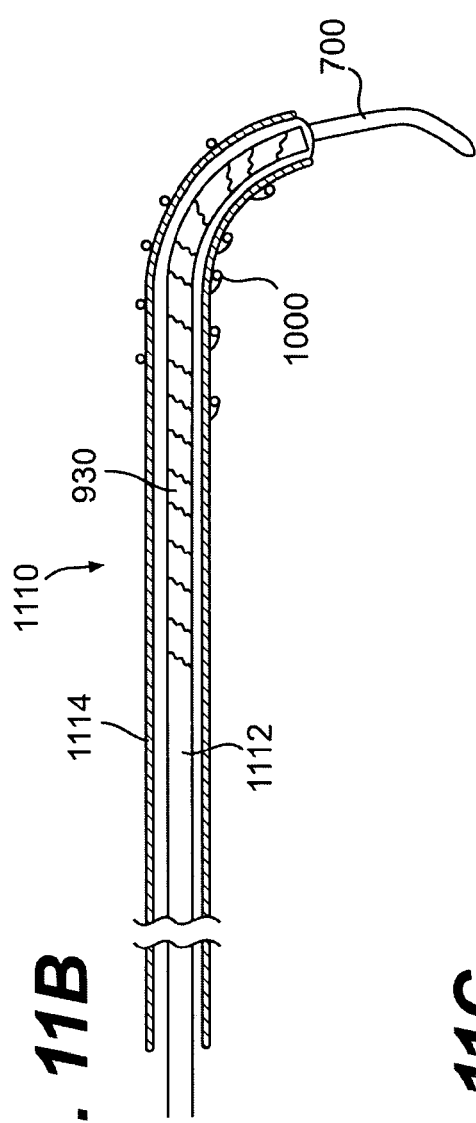
Figure 11C:
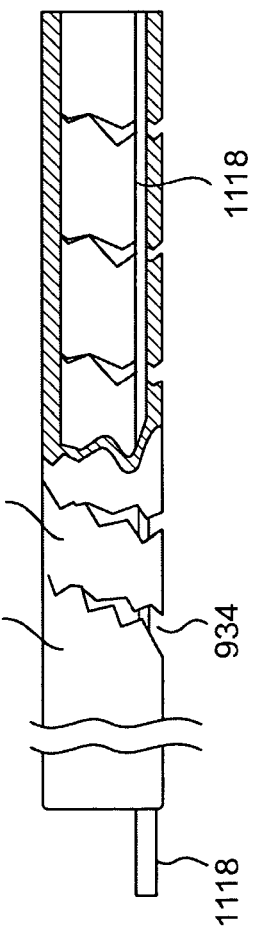

FIG. 11A shows an over-the-wire type subintimal device 1100 (or wire support device) having a coiled gear design 930 as described with reference to FIGS. 9G-9J and a thread design 1000 as described with reference to FIGS. 10A-10D. The device 1100 has a hollow core and may be advanced over a guide wire 700. The geared coils 930 provide axial flexibility and torsional rigidity and the external helical threads provide mechanical engagement with the lesion or arterial wall. FIG. 11B shows an over-the-wire type subintimal device 1110 (or wire support device) in longitudinal section, with an inner tube 1112 having a coiled gear design 930, and an outer tube 1114 having a thread design 1000. The inner tube 1112 contains a guide wire lumen capable of accepting a conventional guide wire 700. FIG. 11C shows a partial enlarged view of an alternative inner tube 1112 where gaps 934 between adjacent coils allow articulation of the inner tube 1112 upon proximal withdrawal of actuation wire 1118. Outer tube 1114 may freely rotate with respect to inner tube 1112 when the inner tube 1112 is in both the straight and actuated positions.

In the foregoing embodiments, the subintimal device enters the subintimal space via an entry point. In other words, the subintimal device extends from the true lumen and into the subintimal space through the entry point. This may be accomplished by directing a subintimal device toward the intimal layer and penetrating therethrough. Alternatively, a guide wire may be used to penetrate the intimal layer and enter the subintimal space. This latter approach may be more commonly employed since physicians often find themselves unintentionally entering the subintimal space with a guide wire. However, to facilitate definitive exploitation of the subintimal space, the embodiments described herein intentionally facilitate penetration of the intimal layer and entry into the subintimal space, which is contrary to conventional current practice.

Figure 12A:
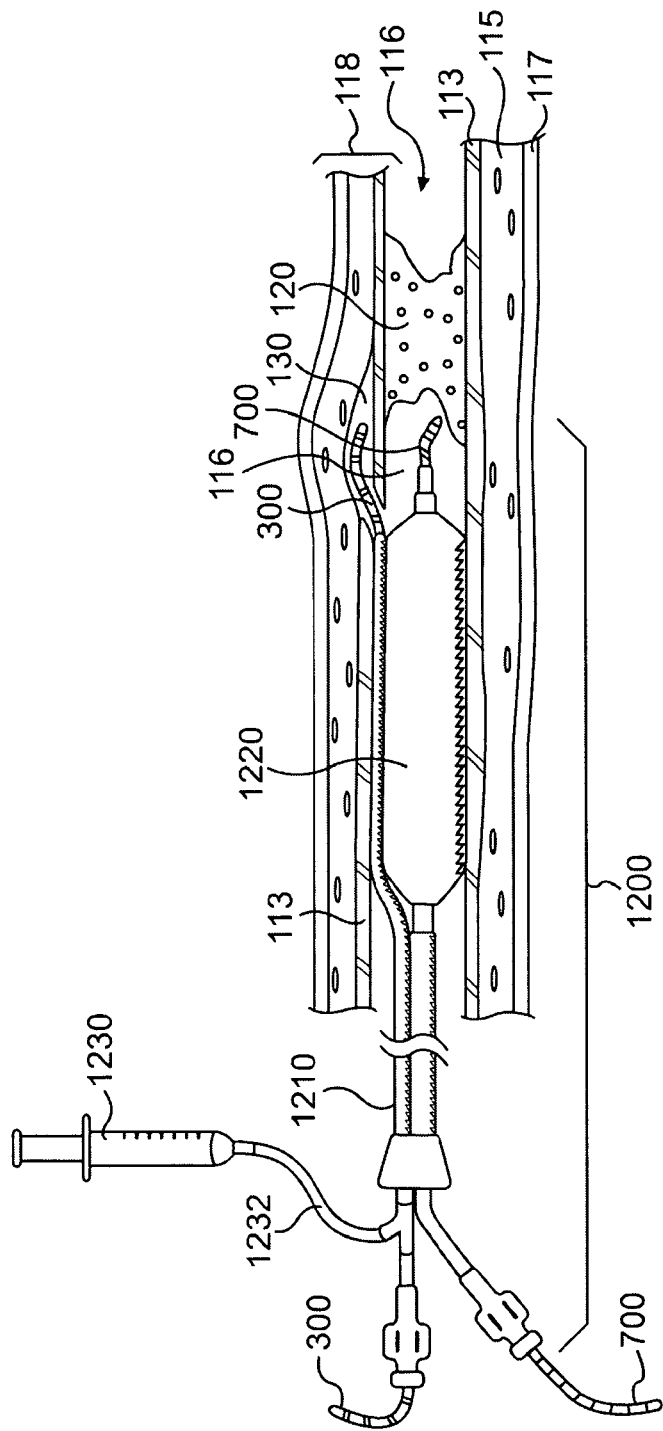
FIGS. 12A-12C schematically illustrate various directing devices for directing a subintimal device to engage and penetrate the intimal layer and enter the subintimal space.
Figure 12B:
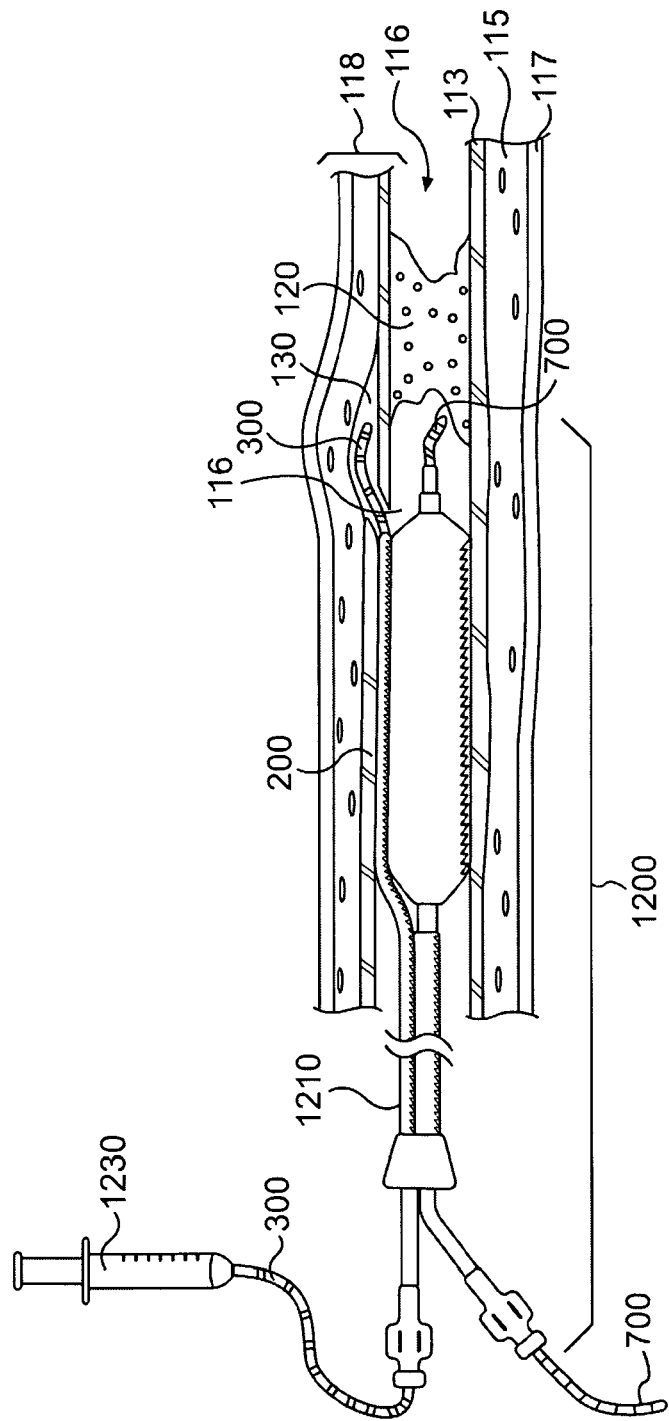
Figure 12C:
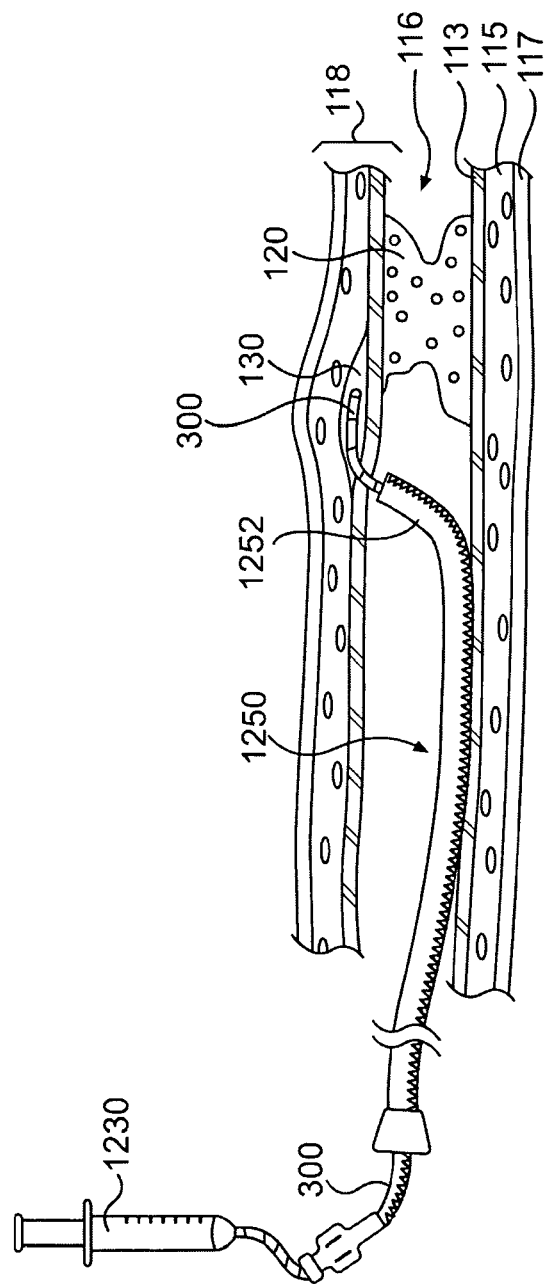

It is contemplated that a bare guide wire (i.e., a guide wire without a directing catheter) using a bent tip at a length and angle sufficient to engage the intima away from the true lumen, may be used to intentionally penetrate the intima and enter the subintimal space. However, a directing catheter may be employed to consistently and predictably facilitate entry into the subintimal space. As illustrated in FIGS. 12A-12C, various directing devices may be used to direct the subintimal device (or guide wire over which the subintimal device is advanced) to engage and penetrate the intimal layer and enter the subintimal space.

FIG. 12A schematically illustrates a directing catheter 1200 substantially similar to an over-the-wire balloon catheter including a distal balloon 1220 with the addition of a delivery and directing tube 1210. As shown, the directing catheter 1200 has been advanced over a conventional guide wire 700 and inflated proximal to the total occlusion 120. For the sake of clarity, FIG. 12A shows a subintimal device path that is substantially parallel to the vessel lumen, but other orientations (e.g., helical) may also be employed. The delivery and directing tube 1210 may be positioned adjacent to and pointed slightly outward and toward the intimal layer 113 such that the subintimal device 300 may be advanced to perforate the subintimal layer 113. A fluid source (e.g., syringe) 1230 may be connected to be in fluid communication with the delivery and directing tube 1210 via an infusion tube 1232. Fluid may flow from the fluid source 1230 through the delivery and directing tube 1210 under a controlled pressure or a controlled volume. The infused fluid may enter the subintimal space 130 directly from the delivery and directing tube 1210 or from the true lumen 116 space defined between the distal end of the balloon 1220 and the proximal edge of the occlusion 120. The fluid may be radiopaque contrast media to facilitate fluoroscopic visualization of the subintimal space, and/or may be used to delaminate the intimal layer 113 and medial layer 115 defining the subintimal space 130. FIG. 12B schematically illustrates an alternative embodiment of directing catheter 1200 wherein the fluid source 1230 is in fluid communication with a lumen within the subintimal device 300 thereby directly infusing fluid into the subintimal space 130 via subintimal device 300. FIG. 12C schematically illustrates another embodiment wherein the directing catheter 1250 is similar to a sub-selective guide catheter wherein the distal end 1252 has a predefined shape or an actuating element that allows manipulation by the physician intra-operatively to direct the subintimal device 300 toward the intimal layer for penetration therethrough.

Once the subintimal device is in the subintimal space, the intima may be delaminated from the media to open the subintimal space by blunt dissection as the subintimal device is being advanced. Alternatively, the intima may be delaminated from the media using pressurized fluid as described previously. As a further alternative, the layers may be delaminated by actuation as illustrated in FIGS. 13A and 13B. Subintimal device 1300 may be actuated or self-expanded between a collapsed configuration shown in FIG. 13A and an expanded configuration shown in FIG. 13B. The device 1300 may be advanced in a collapsed state until resistance is felt, and then expanded to delaminate layers in the expanded state in order to propagate the subintimal dissection. The subintimal device 1300 may comprise a shaft 1310 having a plurality of resilient expandable elements 1312 (e.g., heat set NiTi) and an atraumatic tip 1314 (shown bent). A sheath 1320 may be disposed about the proximal shaft 1310 and the expandable elements 1312 to retain the expandable elements 1312 in a collapsed configuration as shown in FIG. 13A. Upon proximal retraction of the sheath 1320 (or distal advancement of the shaft 1310) the expandable elements 1312 elastically expand as shown in FIG. 13B to cause propagation of the dissection. The sheath 1320 may be advanced to collapse the expandable elements 1312 and the device 1300 may be advanced further into the subintimal space. Alternatively, the actuation mechanism may comprise an inflatable balloon that dissects when inflated and is advanceable when deflated.

Figure 13C:
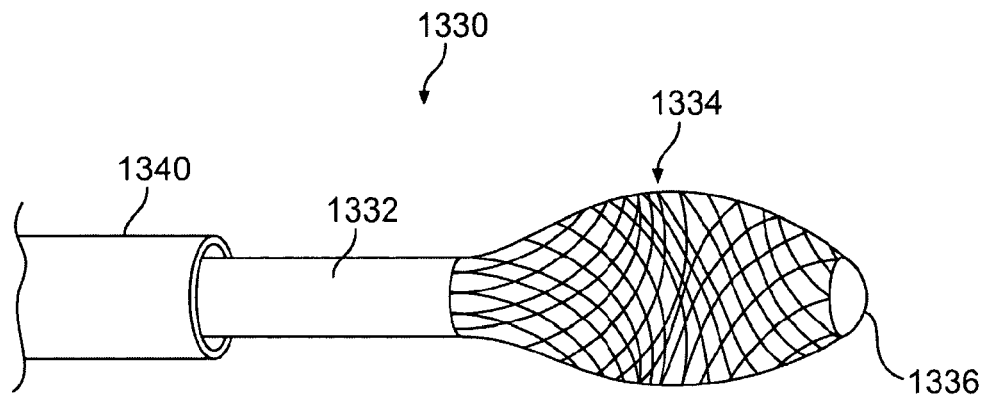
FIGS. 13C, 13D, 13E and 13F schematically illustrate alternative subintimal devices capable of dissection.
Figure 13D:
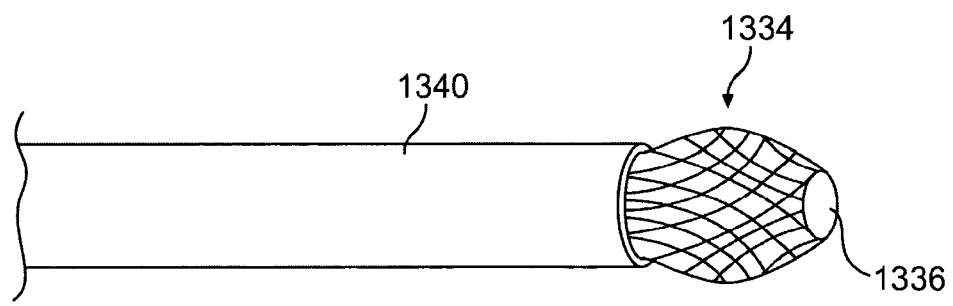

FIGS. 13C and 13D schematically illustrate an alternative subintimal crossing device 1330. Subintimal device 1330 may be actuated or self-expanded between a collapsed configuration shown in FIG. 13D and an expanded configuration shown in FIG. 13C to delaminate the layers of the vascular wall. Alternatively, the subintimal device 1330 may be nominally in the expanded configuration and collapsible upon retraction. The device 1330 may be advanced in a collapsed state until resistance is felt, and then expanded to delaminate layers in the expanded state in order to propagate the subintimal dissection. The subintimal device 1330 may comprise a flexible shaft 1332 and an expandable element 1334. The shaft may comprise a flexible superelastic metal tube (e.g., NiTi) or a composite polymeric shaft (e.g., braid reinforced polyether block amide). The expandable element 1334 may be connected to the distal end of the shaft 1332 using an adhesive or weld joint, for example. The expandable element 1334 may comprise a plurality of braided filaments formed of a resilient material such as NiTi, and may be heat set in the expanded state or the collapsed state. The distal end of the expandable element 1334 may comprise an atraumatic tip comprising, for example, a weld ball 1336 securing the individual braided filaments. The expandable element 1334 may be expanded by pushing on the shaft 1332 when resistance to advancement is encountered, thus delaminating adjacent tissue layers. Alternatively, the expandable element 1334 may be expanded by pushing on the shaft 1332 and pulling on a pull wire (not shown) attached to the distal end of the expandable element 1334 and extending proximally through the lumen of the shaft 1332. A flexible polymeric sheath 1340 may be used to facilitate delivery of the crossing device 1330, provide and maintain a crossing path within the vascular wall, and/or to facilitate removal of the crossing device 1330 as shown in FIG. 13D. The polymeric sheath 1340 may alternatively comprise an orienting device as described herein or another intravascular device (e.g., balloon catheter) configured to be advanced over a guide wire or the like.

Figure 13E:
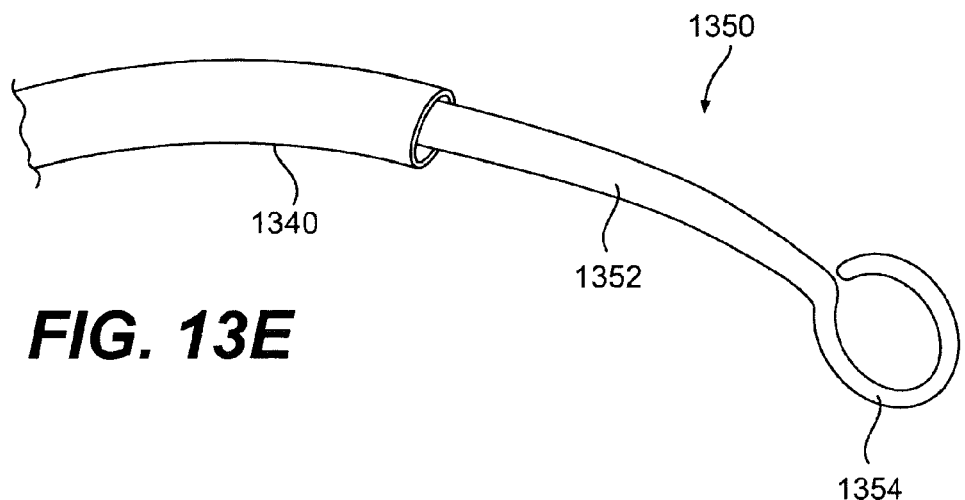
Figure 13F:
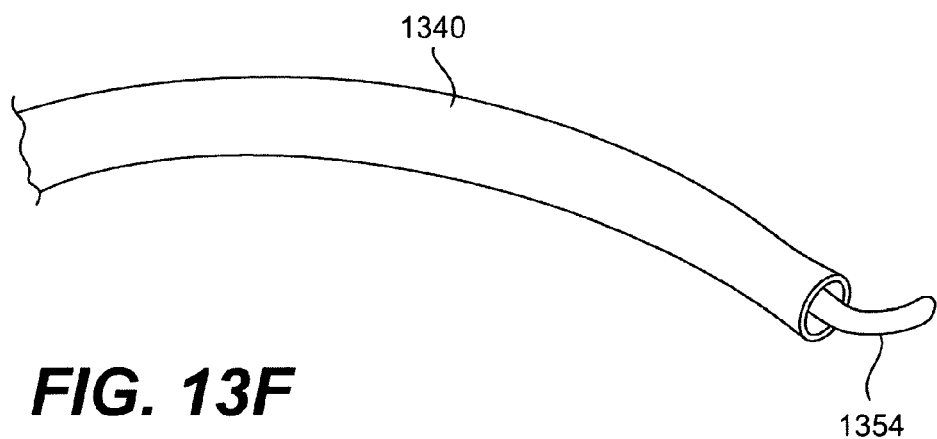

FIGS. 13E and 13F schematically illustrate an alternative subintimal crossing device 1350. Subintimal device 1350 includes an elongate flexible and torqueable shaft 1352 and a distal elastic loop 1354 formed of a superelastic metal alloy such as NiTi, for example. The loop 1354 may be self-expanded between a collapsed configuration shown in FIG. 13F and an expanded configuration shown in FIG. 13E. The device 1350 may be advanced distally through sheath 1340 for delivery and pulled proximally into sheath 1340 for removal. When expanded, the loop 1354 may be substantially planar, and with rotation of the shaft 1352, the loop 1354 rotates in the subintimal space forcing delamination of tissue layers.

Bypass Embodiments

The foregoing embodiments generally involve penetrating the intimal layer, placing a subintimal device in the subintimal space, and traversing across the occluded segment for purposes of defining the vascular boundary and/or for purposes of guarding against perforation. The following bypass embodiments also involve the initial steps of penetrating the intimal layer, placing a subintimal device in the subintimal space, and traversing across the occluded segment. To this end, the devices and methods described with reference to boundary definition and perforation guard embodiments have application to the following bypass embodiments.

Figure 14A:
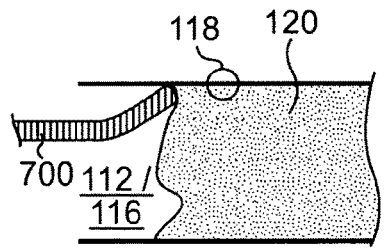
FIGS. 14A-14H schematically illustrated the steps involved in bypassing a total occlusion via the subintimal space.
Figure 14B:
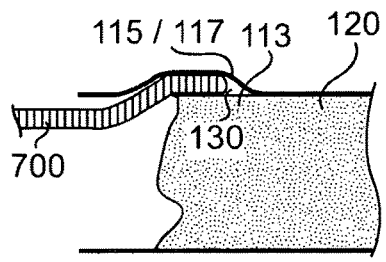
Figure 14C:
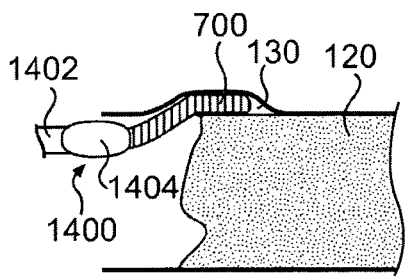
Figure 14D:
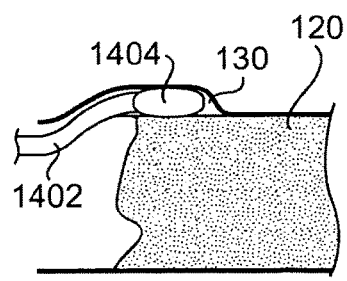
Figure 14E:
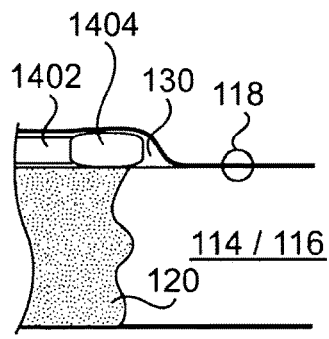
Figure 14F:
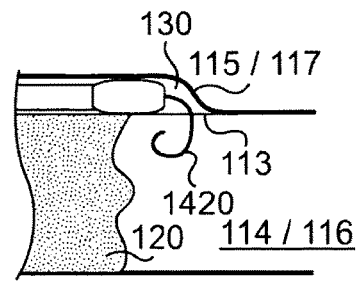
Figure 14G:
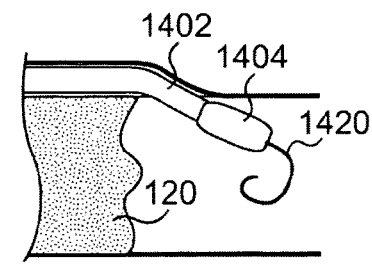
Figure 14H:
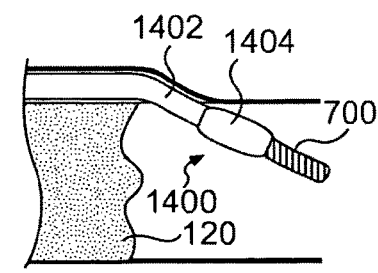

In addition to penetrating the intimal layer, entering the subintimal space, and traversing the occluded segment, the following bypass embodiments generally involve orientation and re-entry into the true lumen. A general approach to the foregoing bypass embodiments is schematically illustrated in FIGS. 14A-14H. A guide wire 700 may be advanced through the proximal segment 112 of the true lumen 116 of the occluded artery to the proximal edge of the total occlusion 120 adjacent the vessel wall 118 as shown in FIG. 14A. By manipulating and directing the guide wire 700 to the proximal edge of the total occlusion 120 toward the wall 118, the guide wire 700 may penetrate the intimal layer 113 and enter the subintimal space 130 between the intima 113 and the media/adventitia 115/117 as shown in FIG. 14B. The manipulating and directing of the guide wire 700 as described above may be performed by using the guide wire alone or by using any of the directing devices described herein. With the guide wire 700 in the subintimal space 130, a subintimal device 1400 may be advanced over the guide wire 700 as shown to FIG. 14C. In the illustrated embodiment, the subintimal device 1400 includes a hollow elongate shaft 1402 and an atraumatic bulbous tip 1404. However, any of the subintimal devices described herein may be employed, particularly the over-the-wire type subintimal devices. As shown in FIG. 14D, the subintimal device 1400 may be further advanced over the guide wire 700 such that the tip 1404 resides in the subintimal space 130. At this procedural stage, the guide wire 700 may be withdrawn, completely removing it from the subintimal device 1400. Further manipulation of the subintimal device 1400 (both axial advancement and radial rotation) allows blunt dissection of the layers defining the subintimal space 130 and advancement of the device 1400 to the distal portion of the total occlusion 120 as shown in FIG. 14E. Penetration of the intimal layer 113 and re-entry into the distal segment 114 of the true lumen 116 distal to the occlusion 120 may be achieved by various means described later in detail, which generally include the steps of orientation toward the center of the true lumen 116 and penetration of the intimal layer 113. For purposes of illustration, not limitation, FIG. 14F shows a shaped re-entry device 1420 having a curled and sharpened tip exiting the lumen of the subintimal device 1400 distal of occlusion 120 and entering the distal segment 114 of the true lumen 116 through the intimal layer 113. With re-entry device 1420 in the distal segment 114 of the true lumen 116, the subintimal device 1400 may be advanced into the true lumen 116 over the re-entry device 1420 as shown in FIG. 14G. The re-entry device 1420 may be withdrawn from the subintimal device 1400 and the guide wire 700 may be advanced in its place as shown in FIG. 14H, after which the subintimal device 1400 may be withdrawn leaving the guide wire 700 in place. As such, the guide wire 700 extends from the proximal segment 112 of the true lumen 116 proximal of the occlusion 120, traverses the occluded segment via the subintimal space 130, and reenters the distal segment 114 of the true lumen 116 distal of the occlusion 120, thus bypassing the total occlusion 120 without exiting the artery. With the guide wire 700 so placed, the subintimal space 130 may be dilated (e.g., by balloon angioplasty or atherectomy) and stented, for example, or otherwise treated using known techniques.

As mentioned above, re-entry into the true lumen from the subintimal space generally involves orientation toward the center of the true lumen and penetration of the intimal layer. Although fluoroscopy is a commonly available visualization tool used during interventional procedures, it only provides two-dimensional images which are typically insufficient, taken alone, to determine the proper direction for penetration from the subintimal space toward the center of the true lumen. As such, those skilled in the art may use visualization tools with greater accuracy or with the ability to show three dimensional data. For example, intravascular ultrasound (IVUS) or magnetic resonance imaging (MRI) may be used to determine the position and direction of true lumen re-entry from the subintimal space. However, such techniques are time consuming, expensive and often impractical, and therefore it would be desirable to facilitate orientation (i.e., direct a re-entry device from the subintimal space toward the true lumen distal of a total occlusion) without the need for such burdensome visualization techniques.

Various orientation and re-entry embodiments are described herein that take advantage of the position and geometry of the subintimal space relative to the true lumen to facilitate effective orientation of a re-entry device from the subintimal space toward the true lumen. This may be accomplished by recognizing that the subintimal space is generally annular with its radial center at the center of the true lumen. Thus, a curved device deployed in the subintimal space defines at least an arc and at most a full circle (in radial cross-section), the radial center of which must reside at the center of the true lumen. In other words, if a curved device that is deployed in the subintimal space such that the curvature of the device is aligned with the curvature of the subintimal space, then the true lumen is by necessity oriented toward the concave side of the curved subintimal device. A re-entry device may then be keyed or otherwise oriented to the concave side of the subintimal device, and is thus automatically oriented toward the true lumen without visualization.

One such embodiment that operates under this premise is shown schematically in FIGS. 15A and 15B. In this embodiment, a helical subintimal device 1500 is shown generically, the features of which may be incorporated into other subintimal device embodiments described herein. Subintimal device 1500 generally includes an elongate tubular shaft 1502 having a lumen 1504 extending therethrough and a re-entry port 1506 disposed distally in the region of the helical shape. In this embodiment, the distal portion of the shaft 1502 may have a helical shape in its relaxed state such that the re-entry port 1506 is always oriented toward the concave side or center of the helix as shown in FIG. 15A. The helical portion may be deployed in the subintimal space around the total occlusion as described elsewhere herein, resulting in the concave portion of the helix and the port 1506 being oriented toward the true lumen. With this arrangement, a re-entry device such as a guide wire 700 or flexible stylet with a tissue penetrating tip may be advanced through the lumen 1504 of the shaft 1502 to exit the re-entry port 1506 as shown in FIG. 15B. This arrangement may be used to establish re-entry into the true lumen after the subintimal device 1500 has been deployed across an occlusion in the subintimal space.

Other orientation and re-entry embodiments are described herein that take advantage of the different properties of the layers of the artery wall to facilitate effective orientation of a re-entry device from the subintimal space toward the true lumen. In some instances, the intima 113 is more pliable than the composite of the media 115 and adventitia 117. Thus, expansion of an element in the subintimal space 130 will result in more deflection of the intima 113 than the media 115 and adventitia 117.

Figure 16A:
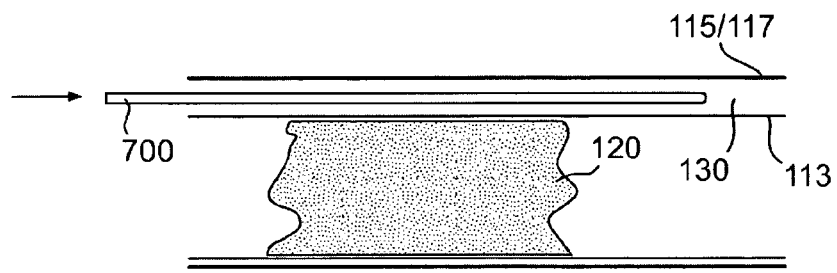
FIGS. 16A-16D schematically illustrate an alternative embodiment for orienting and reentering the true lumen.
Figure 16B:
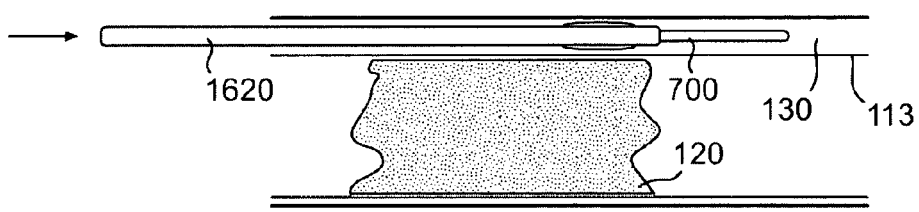
Figure 16C:
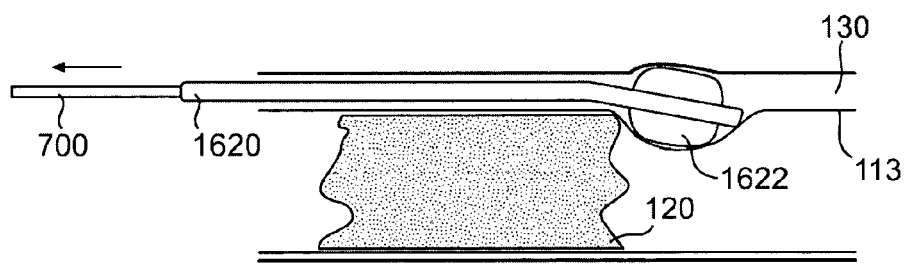
Figure 16D:
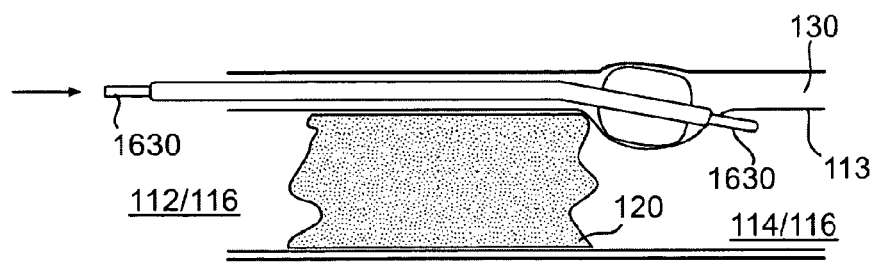

One such embodiment that operates under this premise is shown schematically in FIGS. 16A-16D. In this embodiment, a subintimal device (not shown) as described elsewhere herein may be used to pass the total occlusion and place a guide wire 700 as shown in FIG. 16A. The guide wire 700 extends across the occlusion 120 and is disposed in the subintimal space 130 between intima 113 and the media/adventitia 115/117 where re-entry into the true lumen 116 distal of the occlusion 120 is desired. A balloon catheter 1620 is then advanced over the guide wire 700 until the balloon portion 1622 is disposed adjacent the distal end of the occlusion 120 as shown in FIGS. 16B and 16C. The guide wire 700 is pulled proximally and the balloon 1622 is then inflated causing radial displacement of the distal end of the balloon catheter 1620 as shown in FIG. 16C. Inflating the balloon 1622 of the balloon catheter 1620 orients the tip of the catheter 1620 toward the intima 113. The guide wire 700 may be removed from the balloon catheter 1620 and a sharpened stylet 1630 or the like may be advanced through the guide wire lumen of the catheter 1620 until the distal end of the stylet 1630 penetrates the intima 113 as shown in FIG. 16D, thus establishing re-entry from the subintimal path 130 and into the true lumen 116.

Detailed Examples of Bypass Embodiments

In the following embodiments, detailed examples of devices are described which facilitate one or more of the steps involved in visualizing, perforation guarding, and/or bypassing a total occlusion as generally described previously. These devices may for example: (i) facilitate subintimal device tracking by transmitting sufficient axial force and radial torque (sometimes referred to as push and twist respectively) to enter the subintimal space, delaminate the intima from surrounding tissue layers, and traverse the total occlusion via the subintimal space; (ii) facilitate alignment of the subintimal device within the subintimal space with a favorable orientation for true lumen re-entry distal of the total occlusion; (iii) facilitate advancement of a re-entry element that takes advantage of the subintimal device alignment and orientation to direct itself toward the true lumen; (iv) facilitate penetration of the intimal layer to regain access to the true lumen distal of the total occlusion; and/or (v) facilitate confirmation that true lumen re-entry has been achieved.

Detailed Examples of Axial Push Force and Radial Torque Embodiments

Figure 18:
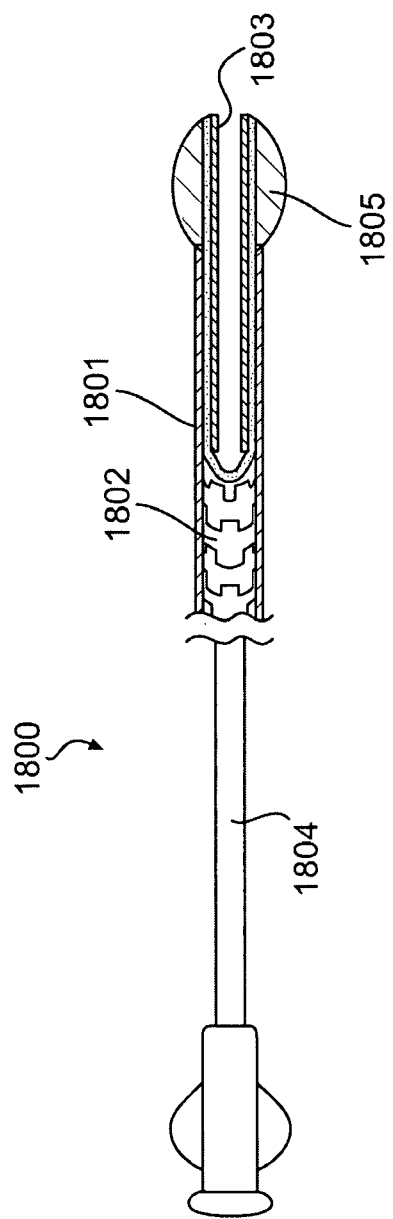
FIG. 18 illustrates an alternative subintimal device.

The embodiments described with reference to FIGS. 17 and 18 illustrate features of subintimal devices that facilitate the transmission of push and twist to enter the subintimal space and advance therein. FIG. 17 shows an embodiment of a subintimal device 1700 where the properties of push and twist may be provided by an internal stylet 1703 slideably disposed within the central lumen 1701 of a tubular shaft 1702. With stylet 1703 removed, the central lumen may also accept a guide wire (not shown).

The tubular shaft 1702 may be made from suitable polymeric materials such as polyethylene, nylon, or polyether-block-amide (e.g., Pebax™). The tubular shaft 1702 may also have composite structure where the inside layer may have a lubricious polymer such as polyethylene or a fluoropolymer such as PTFE (e.g., Teflon™), the middle layer may have a metallic or polymeric braided structure such as polyester or stainless steel, while the outside layer may also be made of a similar polymeric material. The outside of the subintimal device 1700 may also have a lubricious exterior coating. For example, coatings may include liquid silicone or hydrophilic coating such as hyaluronic acid. The stylet 1703 may be made of suitable metallic materials including but not limited to stainless steel or nickel titanium alloys. The atraumatic tip 1704 may be made of suitable metallic or polymeric materials including, for example, stainless steel, titanium, polycarbonate, or polyether-block-amide (e.g., Pebax™).

As seen in FIGS. 17A and 17B, which are cross sectional views taken along lines A-A and B-B, respectively, in FIG. 17, all or a portion (e.g., distal portion) of the stylet 1703 may interface with a feature 1706 within the tubular shaft 1702 and/or within the atraumatic tip 1704. For example, the tubular shaft 1702 and/or the atraumatic tip 1704 may contain a lumen with a geometric feature 1706 intended to mate or key with distal tip of the stylet 1707 as shown in FIG. 17B. This keying or mating feature 1706 allows torque to be transmitted from the operators hand to the distal tip of the subintimal device through twist of the subintimal device and stylet. For the purpose of illustration, the geometric feature 1706 is shown as a square in cross-section, but it is intended that any geometry other than round may be used to create engagement of the perimeter of the stylet 1703 with the internal lumen of the tubular shaft 1702 and/or atraumatic tip 1704.

FIG. 18 shows an embodiment of a subintimal device 1800 having a proximal tubular shaft 1804, a distal tubular shaft 1802, and an atraumatic bulbous tip 1805. In this embodiment, the desired properties of push and twist may be provided by constructing the proximal shaft 1804 of a rigid material (e.g., metallic hypotube) and constructing the distal shaft 1802 in a similar manner, for example, to the gear shaft previously described with reference to FIG. 9 et seq. Distal gear shaft 1802 may be flexible yet torsionally and longitudinally rigid. The distal shaft 1802 may be disposed within an outer sheath 1801 and may have an internal sheath 1803 as well. The outer and inner sheaths may be made of suitable polymeric materials such as polyethylene, nylon, polyether-block-amide (e.g., Pebax™), or a fluoropolymer such as Teflon™.

Detailed Examples Lumen Orientation Embodiments

The embodiments described with reference to FIGS. 19A-19B, 20A-20B, 21A-21B, and 22A-22C illustrate features of subintimal devices that facilitate orientation toward the true lumen. Generally, by deploying a subintimal device around at least a portion of the circumference (sometimes referred to as radial bend or curve), the direction of the true lumen is toward the center (concave side) of the curve. To achieve a radial bend from a longitudinally positioned subintimal device, it may be necessary or desirable to initially impart an axial bend or curve in the subintimal device to act as a transitional geometry. Hence, some subintimal device embodiments described herein have both an axial bend (e.g., FIG. 19A) and a radial bend (e.g., FIG. 19B) when deployed in the subintimal space. Since the concave side of the radial bend is consistently toward the true lumen, a re-entry device may be predictably directed toward the true lumen (without employing complex visualization techniques) by aligning itself with respect to the radial curve of the subintimal device. Thus, in the following embodiments, various subintimal device designs are illustrated that accommodate radial bends (and axial bends) to establish the direction of the true lumen toward the concave side of the radial bend.

Figure 19B:
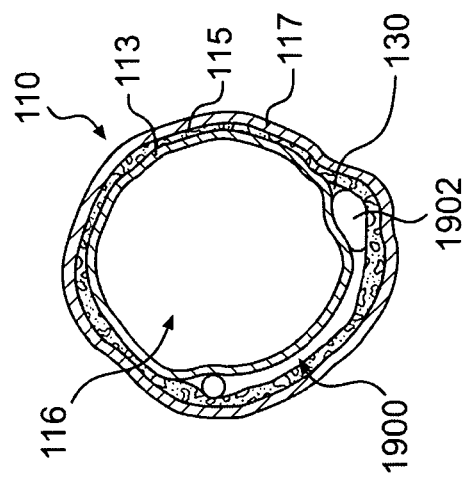
FIGS. 19A and 19B illustrate a subintimal device having a compound bend to facilitate orientation.
Figure 19A:
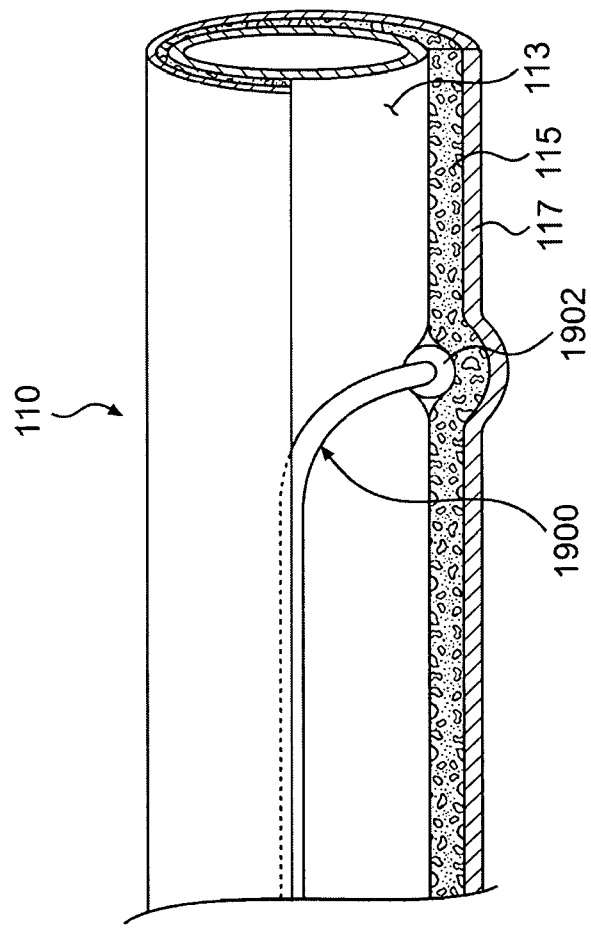

FIGS. 19A and 19B show subintimal device 1900 that is capable of aiming a re-entry device (not shown) toward the true lumen 116 distal of a total occlusion with the aid of standard fluoroscopy. Subintimal device 1900 with atraumatic tip 1902 may be positioned within the subintimal space 130 between the intima 113 and media 115 layers. The subintimal device 1900 may be advanced using similar techniques previously described with reference to FIGS. 14A-14E. Once the subintimal device 1900 is in the proper position within the subintimal space 130, a distal portion of the sub-intimal device 1900 is configured to achieve a geometry having a bend in the longitudinal direction as shown in FIG. 19A and a bend in the radial direction as shown in FIG. 19B. This three-dimensional geometry may be referred to as a compound bend. As will be described in more detail herein, the compound bend may be used to facilitate alignment of a re-entry device toward the true lumen 116 of the artery 110.

Figure 20A:
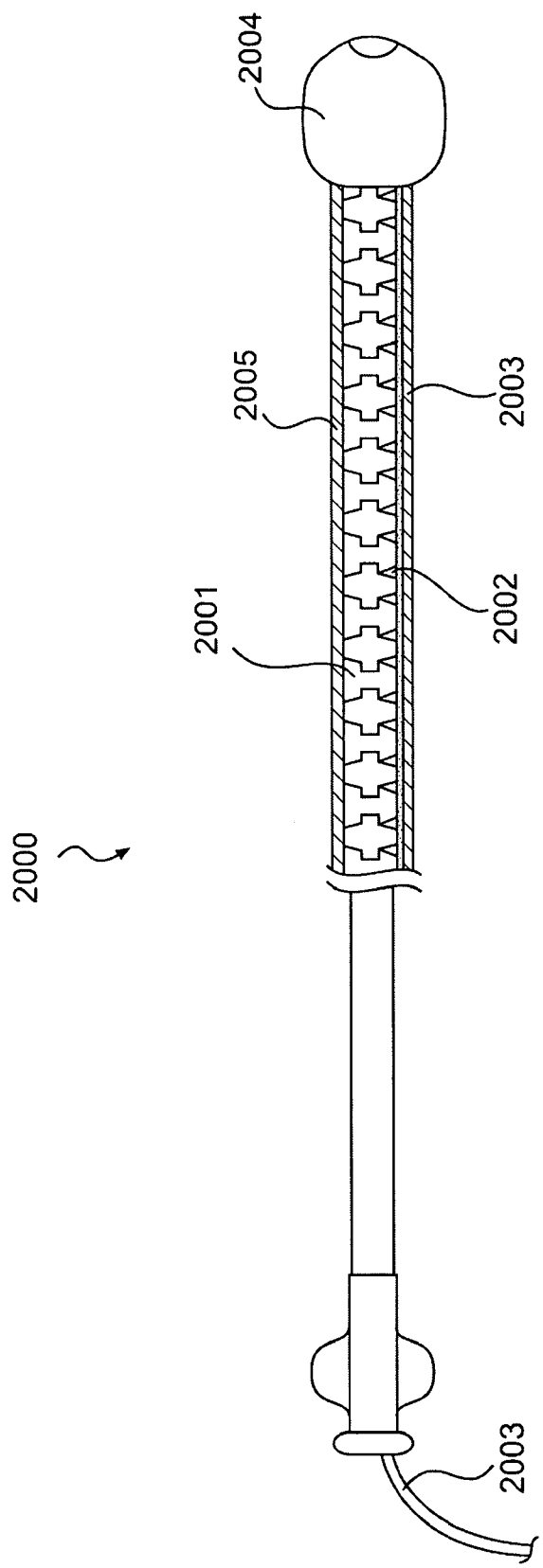
FIG. 20A illustrates an alternative subintimal device capable of achieving a compound bend.
Figure 20B:
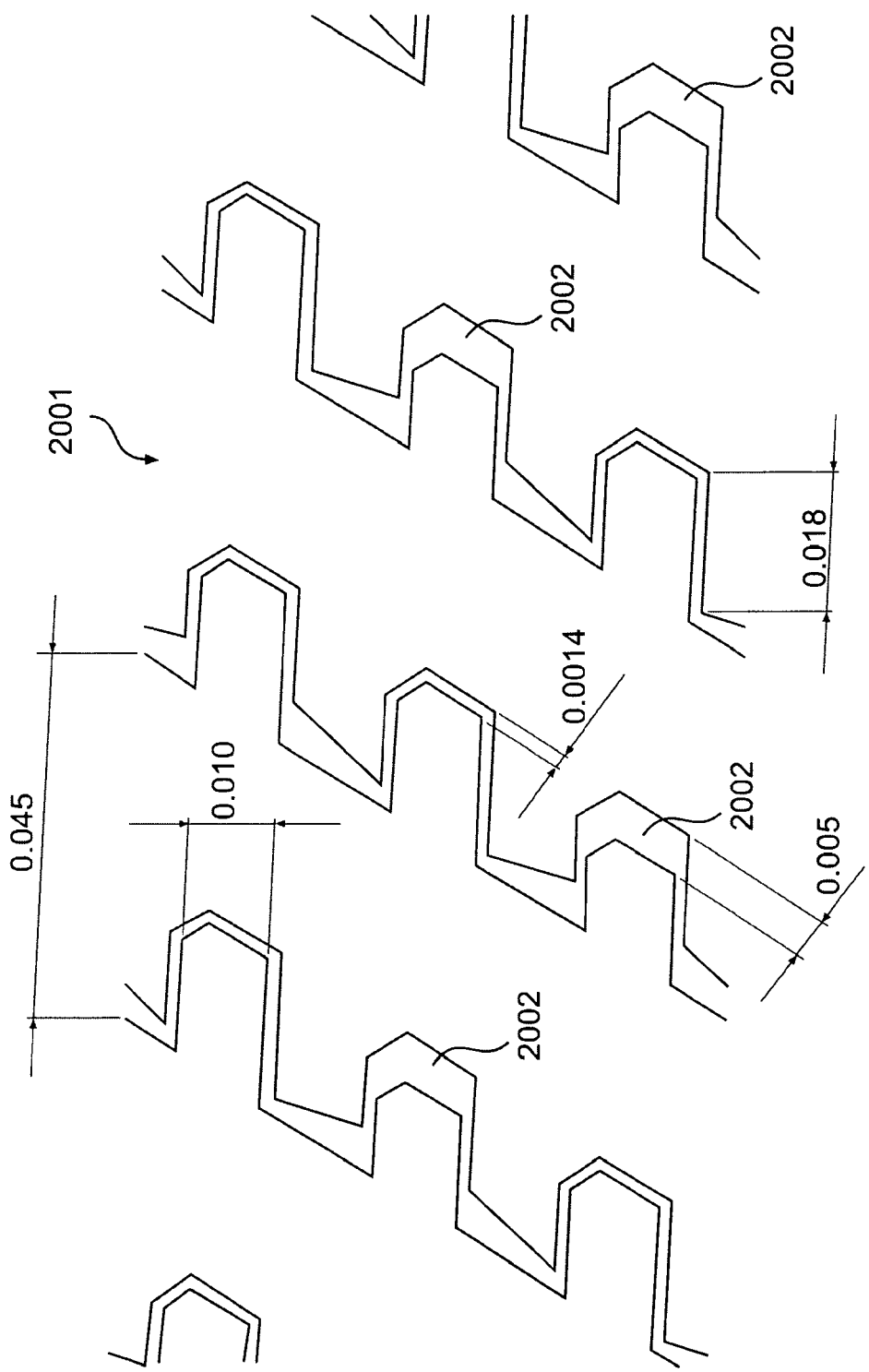
FIG. 20B illustrates a laser cut pattern for a Nitinol tube for use in the device shown in FIG. 20A.

FIG. 20A illustrates a subintimal device 2000, similar to the subintimal device 1800 described with reference to FIG. 18, that may be capable of achieving a compound bend. The subintimal device 2000 includes an elongate tubular shaft 2001 defining an internal lumen, an actuation (e.g., push or pull) member 2003 residing in the lumen of the shaft 2001 and having a distal end attached to the distal end of the shaft 2001, and an atraumatic tip 2004 attached to the distal end of the shaft 2001. The flexible yet torsionally rigid distal shaft 2001 has one or more open areas 2002 oriented along the actuation member 2003. An external sheath 2005 may be disposed about the length of the shaft 2001 and actuation member 2003, with its distal end attached to the atraumatic tip 2004. For purpose of illustration only, FIG. 20A shows a single actuation member 2003 in the proximity of a single row of open areas 2002 in the shaft 2001. The subintimal device may have one or more actuation members and may have one or more rows of open areas. For example, the shaft 2001 may have a laser cut geometry as shown in FIG. 20B with two rows of open areas 2002.

With continued reference to FIG. 20A, a bend may be achieved by pulling the longitudinal actuation member 2003. Pulling the actuation member 2003 partially or completely closes the open spaces 2002 thus shortening the length of the shaft 2001 in proximity of the open areas 2002 and creating a bend in the device 2000. A compound bend may be achieved through the use of multiple rows of open areas and/or multiple longitudinal members 2003. Alternatively, a compound bend may also be achieved using a single row of open areas and a single longitudinal member by relying on device interaction with the adventitial layer. In this alternative, pulling the actuation member 2003 creates the axial curvature (see FIG. 19A) and interaction with the adventitia may force the subintimal device to accommodate a radial curvature (see FIG. 19B).

Figure 21A:
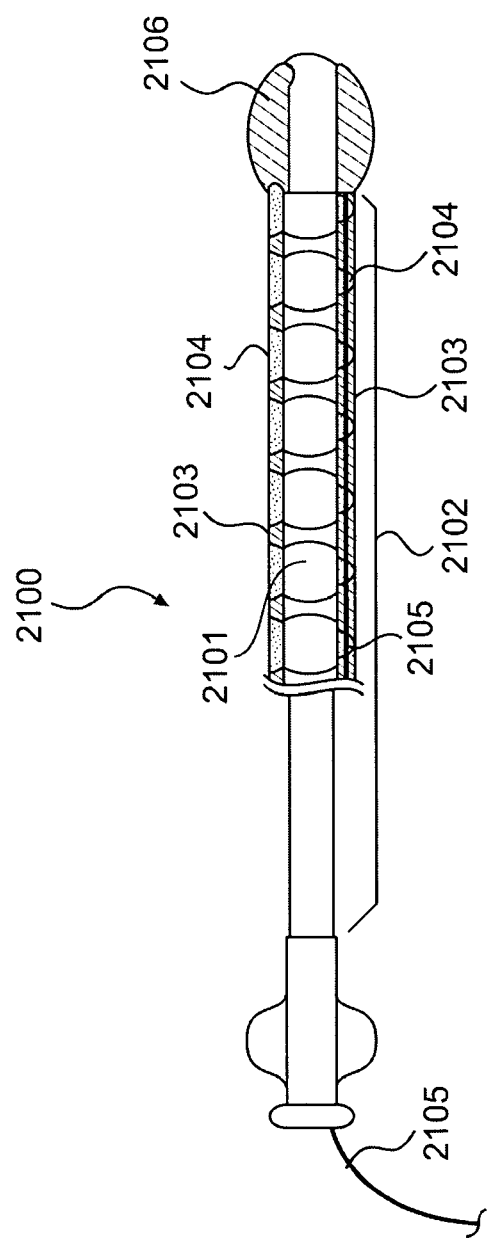
FIGS. 21A and 21B illustrate another alternative subintimal device capable of achieving a compound bend.

FIG. 21A shows an alternative embodiment of a subintimal device 2100 that may also achieve a compound bend. The subintimal device 2001 generally includes an elongate tubular shaft 2102 defining an internal lumen 2101, an actuation (e.g., push or pull) member 2105 having a distal end attached to the distal end of the shaft 2102, and an atraumatic tip 2106 attached to the distal end of the shaft 2102. The shaft 2102 may be constructed from a multitude of alternating wedge-shaped polymeric segments where segment 2103 may have a lower durometer and greater flexibility as compared to the adjacent segment 2104. For example, segment 2103 may be made of 4033 Pebax while segment 2104 may be 6333 Pebax. These multiple segments may be assembled together to make a continuous shaft. For example, the edges of adjacent segments may be fused together using a process that heats the segments above their melt temperature. The application of heat to segments that is held in proximity may allow said segments to fuse together. FIG. 21A shows a series of wedged-shaped segments wherein the relatively stiff segment 2104 defines a larger percentage of one side along a line of the shaft 2102 while the relatively flexible segment 2103 defines a larger percentage of the opposing side of the same shaft.

Figure 21B:
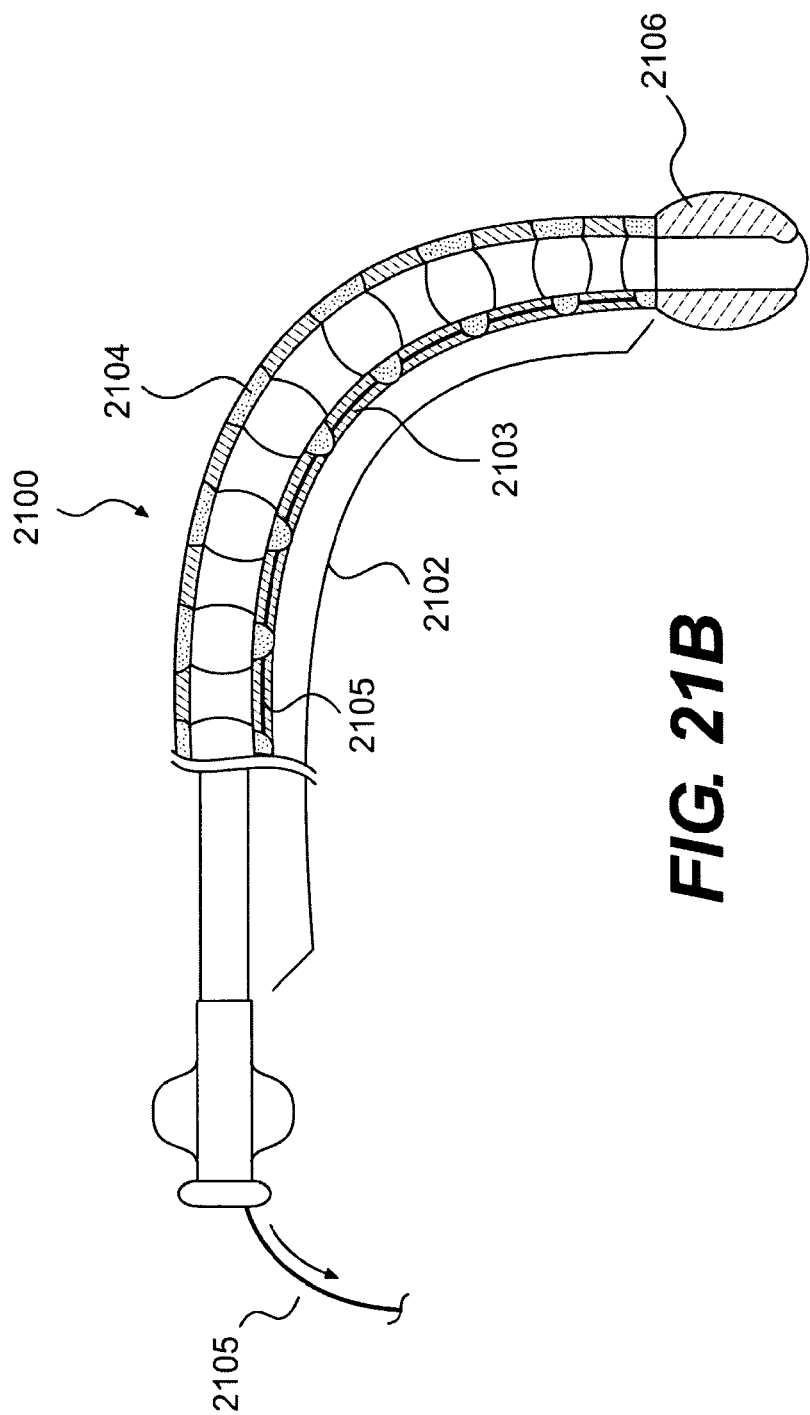

As shown in FIG. 21B, the side of the shaft 2102 with a greater percentage of relatively flexible segments 2103 allows more relative compression upon actuation of member 2105, such that the shaft 2105 may have a predisposition to flex to the side with more flexible segment material 2103 and may have greater resistance to flex to the side with more stiff segment material 2104. The longitudinal actuation member 2105 may be slideably disposed in a lumen within the wall of the shaft 2102 and may be attached to the atraumatic tip 2106, extending the length of the shaft 2105 and out the proximal end. For purpose of illustration, FIGS. 21A and 21B show a single longitudinal member 2105 in the proximity of a line of relatively flexible segments 2103. The subintimal device 2100 may have one or more longitudinal members and may have one or more lines of flexible segments 2103.

With reference to FIG. 21B a compound bend may be achieved by pulling the actuation member 2105 relative to shaft 2102. Pulling the actuation member 2105 may compress segments 2103 thus shortening the subintimal device length along the side of the of the shaft 2102 with mare flexible segment material 2103. A compound bend may be achieved by arranging the flexible segment material 2103 in the desired pattern and/or by using multiple longitudinal members 2105. Alternatively, a compound bend may also be achieved using a single side of flexible segment material 2103 and a single longitudinal member by relying on device interaction with the adventitial layer as described previously.

Figure 22A:
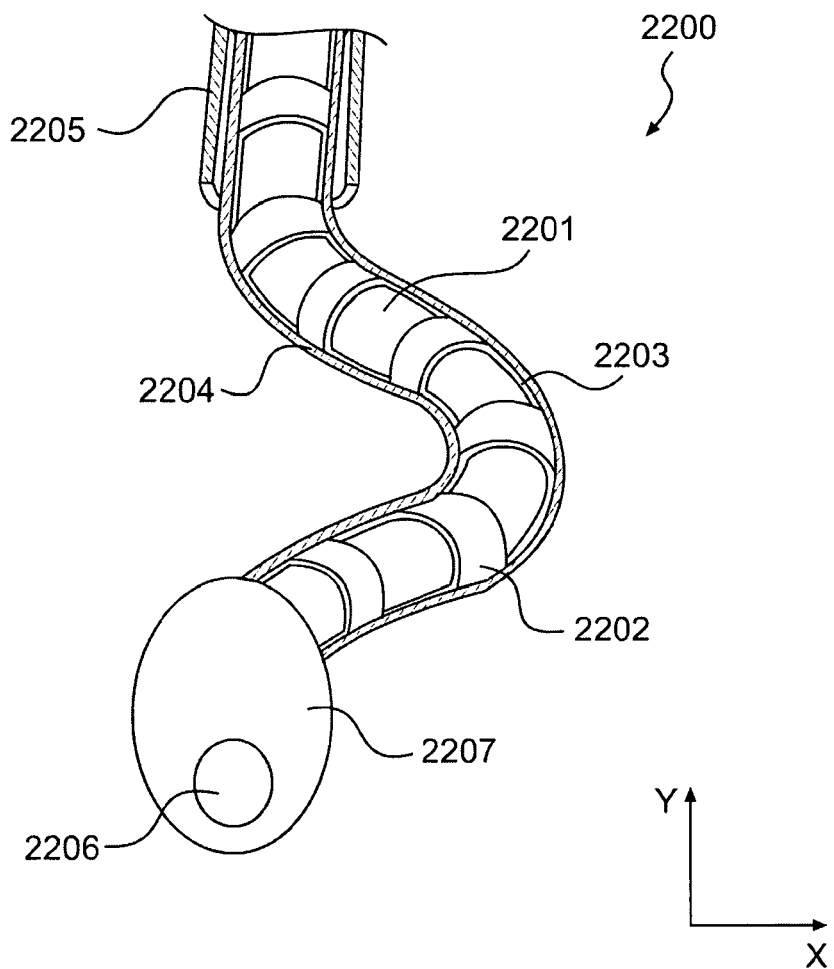
FIGS. 22A-22C illustrate yet another alternative subintimal device capable of achieving a compound bend.
Figure 22B:
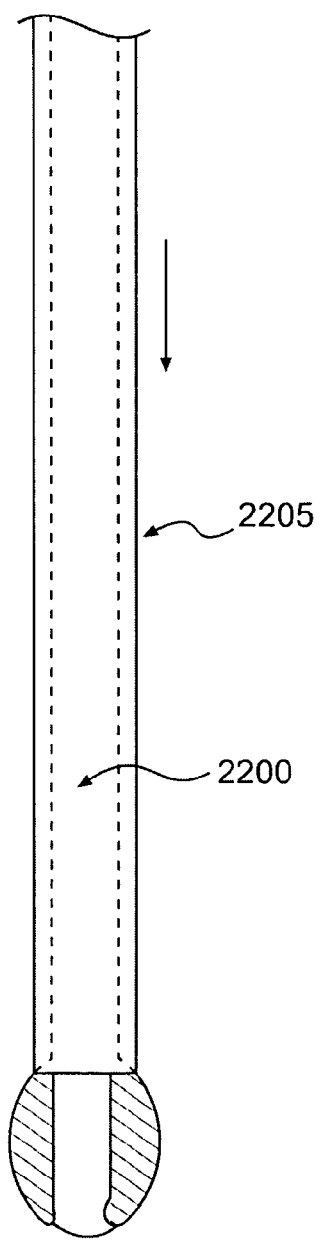
Figure 22C:
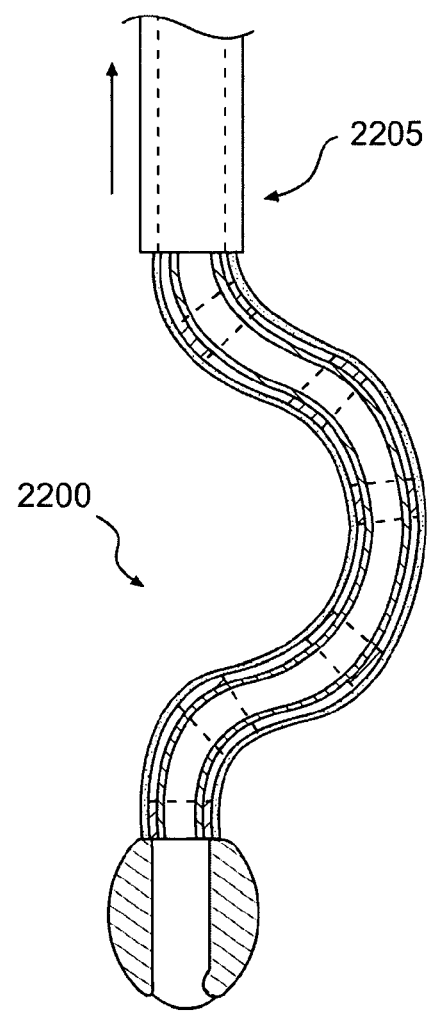

With reference to FIGS. 22A-22C, another embodiment of a subintimal device 2200 capable of achieving a compound bend is shown schematically. FIG. 22A only shows the distal portion of the subintimal device 2200 for purposes of illustration and clarity. In this embodiment, the tubular shaft of the subintimal device 2200 comprises an inner tube 2201 and an outer tube 2204 (shown cut away), between which is disposed a series of circumferential rings 2202 interconnected by longitudinal members 2203. An atraumatic tip 2207 is connected to the distal end of the shaft, and a central lumen 2206 runs through the device 2200 for the acceptance of a guide wire and/or a re-entry device. Suitable materials for the circumferential rings 2202 and longitudinal members 2203 include but are not limited to nickel titanium, stainless steel, or MP35N. The inner tube 2201 and the outer tube 2204 may be made of suitable polymeric materials such as polyethylene, polyether-block-amide (e.g., Pebax™), or nylon. The distal portion of the subintimal device may have a pre-formed curved shape (e.g., compound bend) in its relaxed state as shown in FIG. 22A.

The subintimal device 2200 may be slideably disposed within an external delivery sheath 2205 as shown in FIGS. 22B and 22C. The sheath 2205 may be slightly stiffer then the subintimal device 2200 such that the subintimal device 2200 assumes a straight shape when the sheath 2205 covers the distal portion of the device as shown in FIG. 22B, and assumes a curved shape when the sheath 2205 is retracted as shown in FIG. 22 A. Upon proximal retraction of the sheath 2205, the subintimal device 2200 may assume a compound bend by virtue of its preformed shape, or it may assume axial curvature by virtue of its preformed shape and radial curvature by virtue of interaction with the adventitia as described previously.

Detailed Examples of Re-entry Embodiments

As described above, the concave side of a subintimal device with a radial bend is consistently toward the true lumen. A re-entry device may thus be predictably directed toward the true lumen (without employing complex visualization techniques) by aligning itself with respect to the concave side of the radial curve of the subintimal device. Therefore, in the following embodiments, various re-entry devices are illustrated that align themselves relative to the concave side of a radial bend in a subintimal device to establish predictable re-entry into the true lumen (without employing complex visualization techniques).

Figure 23A:
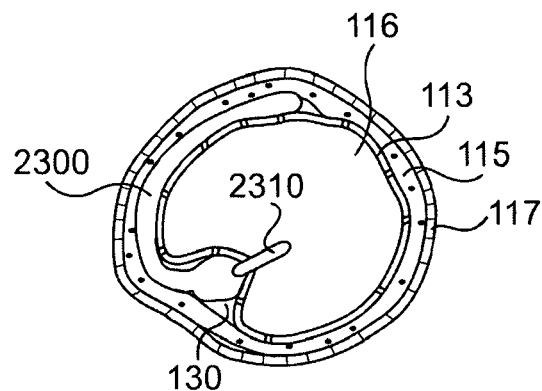
FIGS. 23A-23E illustrate various re-entry device embodiments.

FIGS. 23A-23E show embodiments of re-entry devices that may be advanced through a lumen within a subintimal device 2300. The subintimal device 2300 may be similar to the devices described previously to facilitate formation of a radial bend with a concave side oriented toward the true lumen 116 distal of a total occlusion. With reference to FIG. 23A, subintimal device 2300 may be positioned within the subintimal space 130 between the intimal 113 and medial 115 layers. A radial curve may be formed in the subintimal device 2300 using any of the methods described previously, and the radial curve may be less than the radial curvature of the artery. A radial curvature with a diameter less than the inside diameter of the artery causes the tip of the subintimal device 2300 to be pointed toward the true lumen 116. The re-entry device 2310 may comprise a guide wire, a sharpened stylet or the like to facilitate penetration through the intimal layer. Advancement of the re-entry device 2310 though the central lumen within the subintimal device 2300 and out the distal end results in penetration through the intimal layer 113 and into the true lumen 116.

Figure 23B:
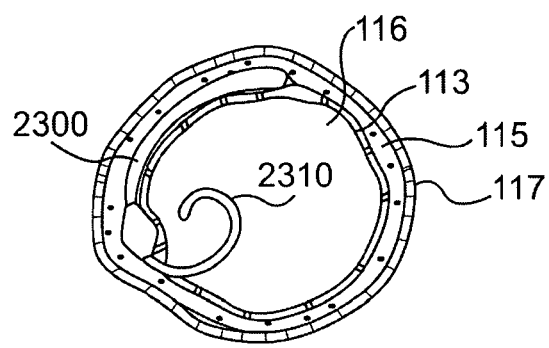

An alternative re-entry embodiment is shown in FIG. 23B wherein the subintimal device 2300 has a radial curvature approximating the inside curvature of the artery. The subintimal device may be placed within the arterial wall between intimal 113 and medial 115 layers as described previously. In this embodiment, the re-entry device 2310 may have a preformed bend that is less than the curvature of the subintimal device 2300 and less than the inside curvature of the artery. The re-entry device is longitudinally and rotationally movable with respect to the subintimal device 2300, thus allowing the curvature of the re-entry device 2310 to self-align with the curvature of the subintimal device 2300. Thus, with the concave side of the curved subintimal device oriented toward the true lumen, the concave side of the curved re-entry device 2310 will also be oriented toward the true lumen. Advancement of the re-entry device 2310 through the subintimal device 2300 and out the distal end thereof results in penetration through the intimal layer 113 and into the true lumen 116. Because the curvature of the re-entry device is less than the inside curvature of the artery, the tip of the re-entry device remains in the true lumen and does not engage the opposite wall of the artery.

Figure 23C:
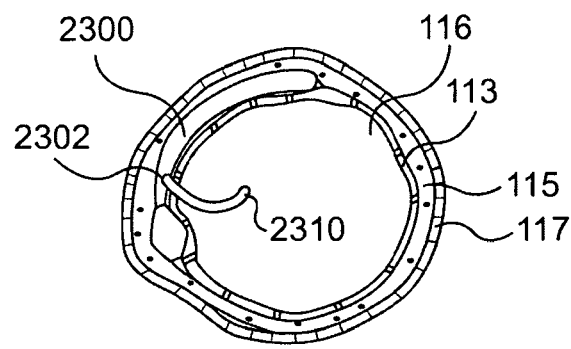

Another alternative re-entry device embodiment is shown in FIG. 23C wherein the re-entry device 2310 exits out a distal side port 2302 in the subintimal device 2300. The side port 2302 may be located on the concave side of the curvature of the subintimal device 2300 thus orienting the tip of the re-entry device 2310 toward the true lumen 116. In this embodiment, the re-entry device 2310 may have a slight bend at its distal end to bias the tip toward the port 2302 such that it exits the port upon advancement.

Figure 23D:
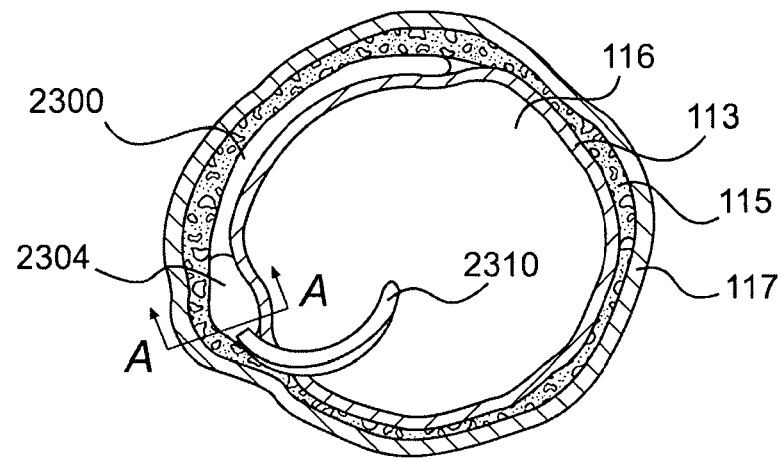
Figure 23E:
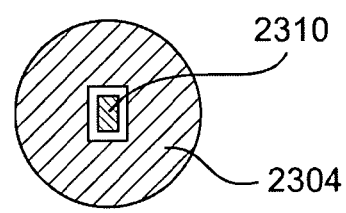

Another alternative re-entry device embodiment is shown in FIGS. 23D and 23E. FIG. 23E is a cross sectional view taken along line A-A in FIG. 23D. In this embodiment, the subintimal device 2300 and the re-entry device may be provided with radial curvature for orientation toward the true lumen 116 as described previously. In addition, a portion of the subintimal device 2300 such as the tip 2304 and a distal portion of the re-entry device 2310 may be provided with a mating or keying geometry to facilitate relative alignment. Various non-circular mating geometries may be used, including a rectangular cross section as shown in FIG. 23E.

Figure 24A:
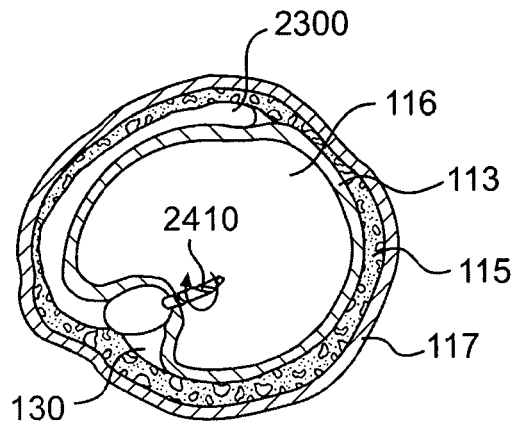
FIGS. 24A-24C illustrate various penetration mechanisms for a re-entry device.
Figure 24B:
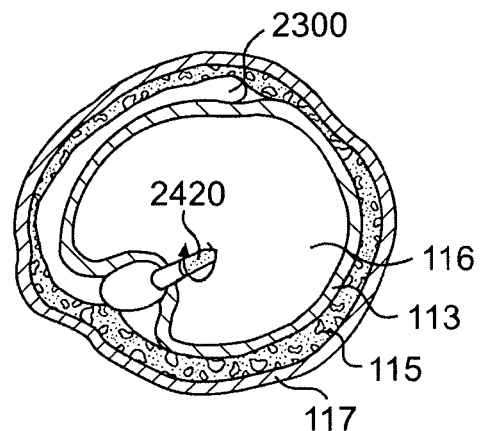
Figure 24C:
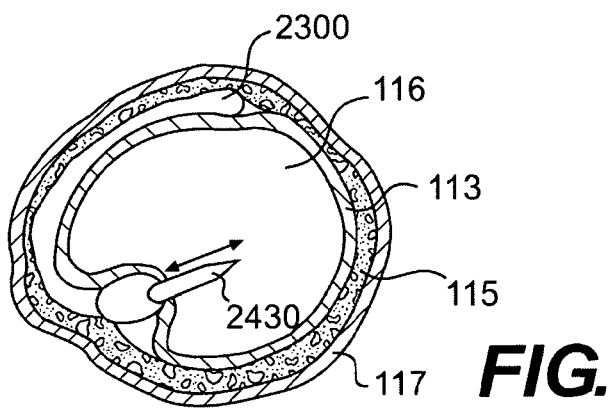

FIGS. 24A-24C show various embodiments of penetrating tips for use on a re-entry device. As mentioned previously, the re-entry device 2310 may comprise a guide wire or the like to facilitate penetration through the intimal layer 113 from the subintimal space 130 to the true lumen 116. Alternatively, the tip of the re-entry device 2310 may be designed to enhance penetration through the intimal layer 113, particularly in the case where the intimal layer is diseased. If the intimal layer 113 is diseased, it will likely be tougher than healthy tissue because it may contain soft plaque, fibrous plaque and/or hard calcified plaque. The presence or absence of disease at the intended re-entry site and the nature of the disease may require a re-entry device capable of penetrating the various plaques within a non-homogenous diseased arterial wall. In the event the re-entry site is free from disease or contains relatively soft plaque, a conventional guide wire may be used as a re-entry device. Alternatively, if disease is encountered, the tip configurations illustrated in FIGS. 24A-24C may be employed.

As shown in FIG. 24A, the re-entry device may have a rotational cutting or piercing element 2410 capable of penetrating the arterial wall. The rotational element 2410 may, for example, be similar to a fluted drill bit. Rotation of the re-entry device with rotational cutting element 2410 may be achieved through manual manipulation by the physician or through a powered mechanism such as an electric motor.

As shown in FIG. 24B, the re-entry device may have a rotational abrasive element 2420. The abrasive element 2420 may include an abrasive coating such as 220 grit diamond abrasive. The abrasive coating may be applied to the tip of the re-entry device through an electroplating process. Rotation of the re-entry device with rotational abrasive element 2420 may be achieved through manual manipulation by the physician or through a powered mechanism such as an electric motor.

As shown in FIG. 24C, the re-entry device may have a tapered or sharpened tip 2430. The sharpened tip 2430 may penetrate the intimal layer 113 through axial advancement or axial reciprocation. The end of the re-entry device, for example, may taper to a sharp point. Axial movement or reciprocation of the tapered or sharpened tip 2430 may be achieved through manual manipulation by the physician or through a powered mechanism such as an electric motor or a solenoid.

Confirmation of a re-entry device entering the true arterial lumen distal of the occlusion may be difficult through the sole use of two-dimensional images obtained via fluoroscopy. These two-dimensional images may allow a physician to determine if a re-entry device is in close proximity to the artery, but may not offer adequate resolution to determine precise position (i.e. within the artery wall vs. within the true arterial lumen). Confirmation of true lumen re-entry may be achieved by understanding when the re-entry and/or the sub-intimal device penetrate the intimal layer 113 and come in contact with the blood in the true lumen 116 distal to the total occlusion.

One method of determining if the true arterial lumen has been accessed is by drawing intra-arterial blood from the distal entry point proximally through a lumen within the re-entry device or a lumen within the subintimal device to the proximal end of the device where the presence of blood may be detected. This method takes advantage of the fact that there is typically blood in the true lumen distal of the occlusion but there is little to no blood in the subintimal space. Thus, the absence of blood indicates the device is subintimal and the presence of blood indicates the device is in the true lumen. This technique may also be used to indicate perforation of the device out of the artery and into the pericardial space by the presence of pericardial fluid.

Figure 25:
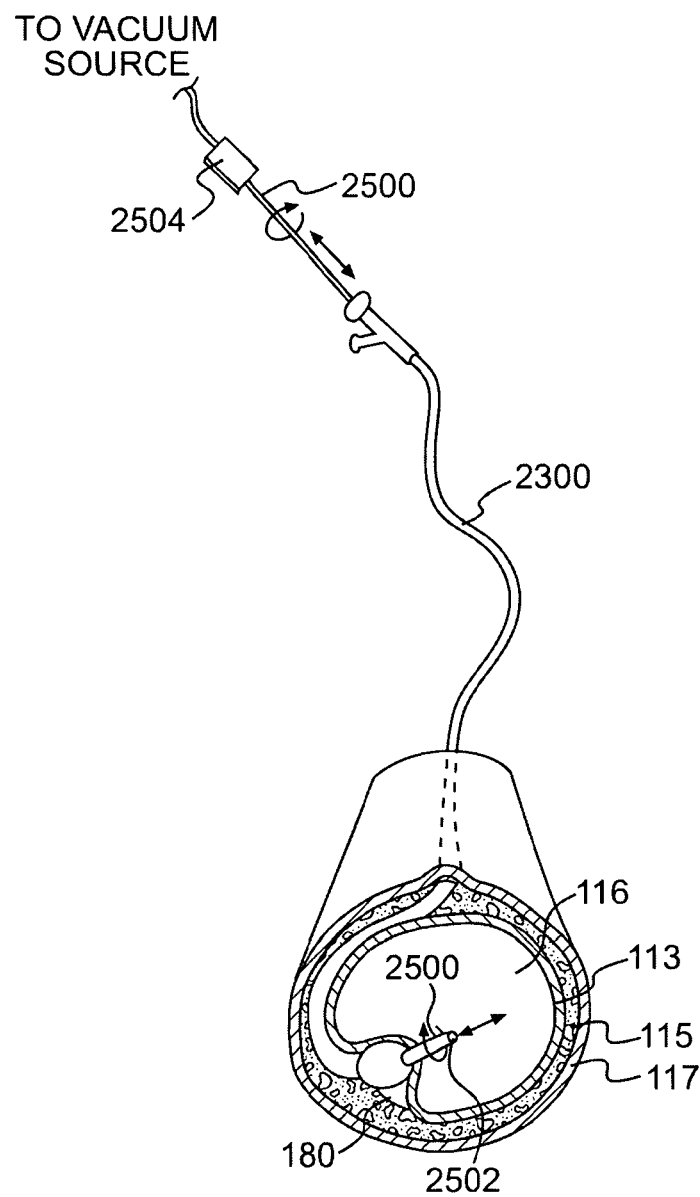
FIG. 25 schematically illustrates a system for confirming true lumen re-entry.

FIG. 25 illustrates a re-entry device 2500 that facilitates confirmation of true lumen re-entry. The re-entry device 2500 may be passed through a subintimal device 2300, oriented toward the true lumen 116, and penetrate the intimal layer 113 from the subintimal space 130 to the true lumen 116 as described previously. In this embodiment, the re-entry device 2500 is provided with an internal lumen extending from its proximal end to a distal opening 2502. The proximal end of the re-entry device 2500 is connected to an indicator 2504 which is in turn connected to a vacuum source. The indicator 2504 may be a flow indicator such as a collection vessel where the presence and type of fluid may be visually observed. With the vacuum source generating a negative pressure, entry of the re-entry device 2500 into the true lumen 116 allows blood to flow into the distal opening 2502 and through the internal lumen to the indicator 2504. Alternatively, the vacuum source and indicator may be fluidly attached to the subintimal device where entry of the device into the true lumen results in similar blood flow into the indicator. Alternative indicators 2504 may be employed such as impedance sensors, oxygen sensors, optical sensors etc.

Detailed Examples of Deployable Element Embodiments

Various devices have been previously described herein that are deployable in the subintimal space for a variety of purposes. The following embodiments are additional examples of such deployable devices that may be used in the same or similar manner. For example, the following embodiments provide a deployable element that when released within the subintimal space along the length and around the circumference of the total occlusion may serve as: (i) a visualization aid that may help define the arterial wall during fluoroscopy; (ii) a protective element that may guard the exterior vessel layer or layers from devices passing through the total occlusion within the true arterial lumen; and/or (iii) a protective element that may provide an indication of close proximity or contact between a device passed through the total occlusion within the true arterial lumen and the protective element. The deployable element may be readily released from and re-captured into an exterior containment sheath. The deployable element may also be released and remain deployed within a patient as a permanent implant. This permanent implant may serve as a stent and/or may also elute a drug.

Figure 26A:
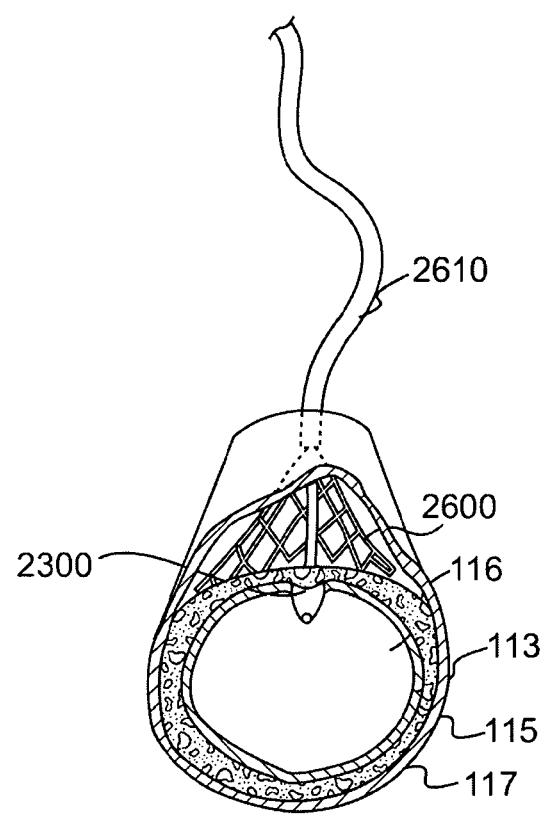
FIGS. 26A and 26B schematically illustrate a subintimal deployable element and delivery system therefor.
Figure 26B:
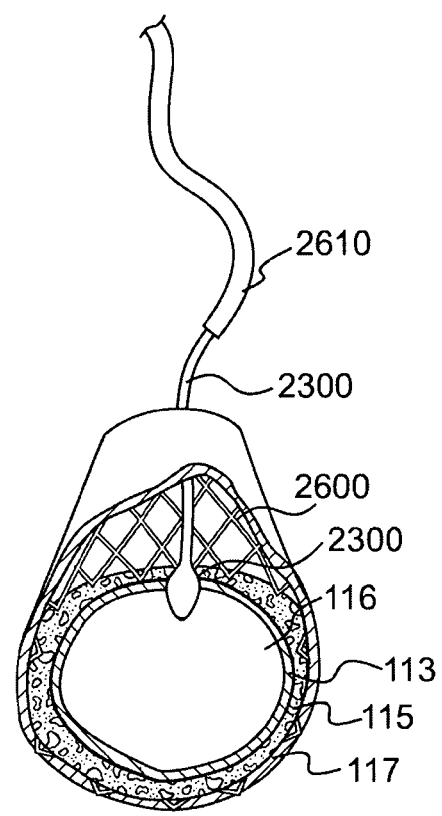

An example of a deployable element 2600 is schematically illustrated in FIG. 26A. The deployable element 2600 may be disposed about a subintimal device 2300 and contained thereon by a retractable containment sheath 2610. In FIG. 26A, the deployable element 2600 is shown in the process of release from its constrained position the proximal refraction of the containment sheath 2610. The deployable element 2600 may comprise, for example, a collapsible lattice structure that is capable of expanding from a first collapsed configuration within the containment sheath 2610 to a second deployed configuration upon refraction of the sheath 2610 that allows it to expand within the arterial wall. In this embodiment, the deployable element 2600 is shown in the submedial space between the media 115 and adventitia 117. FIG. 26B shows the deployable element 2600 completely released from the subintimal device 2300 by complete retraction of the exterior containment sheath 2610. The deployable element 2600 may expand around the circumference and along the length of a total occlusion (not shown) thus concentrically surrounding a diseased segment. The lattice structure of the deployable element 2600 may be made of a material capable of withstanding strain between the collapsed configuration and the deployed configuration without significant permanent deformation. Suitable materials for the deployable element 2600 include but are not limited to nickel titanium, stainless steel, elgiloy, or MP35N.

The deployable element may be used to aid in defining the arterial wall in the area of a total occlusion. As known to those skilled in the art, a totally occluded artery may not allow sufficient radiopaque contrast solution to penetrate the diseased segment thus preventing a physician from visualizing the artery in the occluded area. Placing a deployable element of sufficient radiopacity (as seen via fluoroscopy) within the arterial wall around a total occlusion may allow a physician to visualize the occluded segment. Visualization of the artery in the area of occlusion may allow subsequent interventional devices (i.e. guide wires, balloons, stents, etc.) to be successfully passed within the confines of the deployable element.

Figure 27:
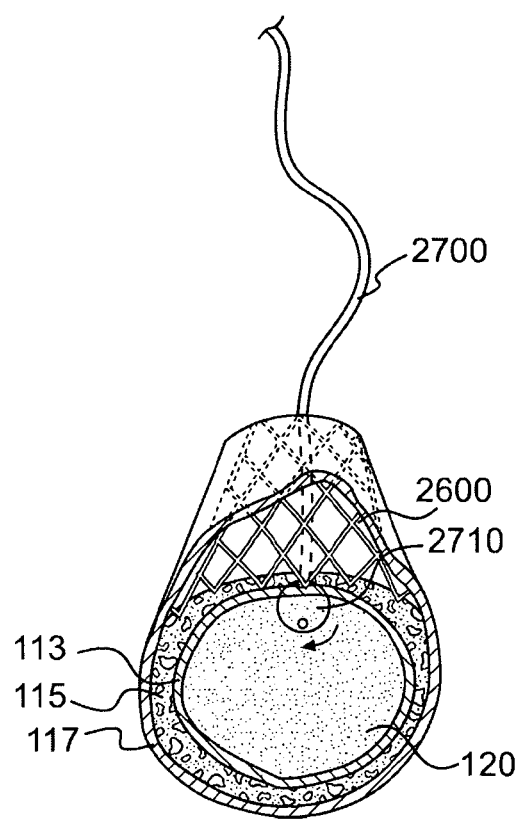
FIG. 27 illustrates the use of a subintimal deployable element for guarding against perforation.

The deployable element may alternatively provide mechanical protection for the arterial layers concentrically outward of the deployable element from crossing devices intended to penetrate the total occlusion such as guide wires, atherectomy devices, laser ablation devices, and radiofrequency ablation devices. For example, FIG. 27 shows a rotational abrasive device 2700 with an abrasive cutting tip 2710 passing through a total occlusion 120 with the deployable element 2600 protecting the arterial wall from perforation. While the abrasive tip 2710 is effective at passing through the total occlusion 120, the deployable element comprises a relatively harder material (e.g., metallic) with a lattice pattern having openings smaller than the tip 2710 to prevent perforation therethrough.

The deployable element may alternatively provide vessel wall protection by indicating when the occlusion crossing device (guide wire, atherectomy device, laser ablation device, and radiofrequency ablation device, etc.) is in close proximity to or in contact with the vessel wall. For example, either the distal end of the deployable element or the distal end of the crossing device may act as a transmitting antenna and the other of the two may act as a receiving antenna. The transmitting antenna may be electrically connected to a radiofrequency (RF) signal generator and the receiving antenna may be connected to an RF signal receiving or detection circuit via a lengthwise insulated and/or shielded lead disposed in each of the devices. As an alternative to RF proximity detection, impedance may be similarly used as an indicator of proximity.

With either an RF or impedance based approach, a relatively weak signal is indicative of the crossing device being further away from the deployable element, for example when the crossing device is in the center of the occluded artery. A relatively stronger signal is indicative of the crossing device being in close proximity to the deployable element, for example within the subintimal space. The physician may use this proximity information to safely and effectively direct the crossing device within the confines of the deployable element and across the total occlusion within the true arterial lumen.

Figure 28:
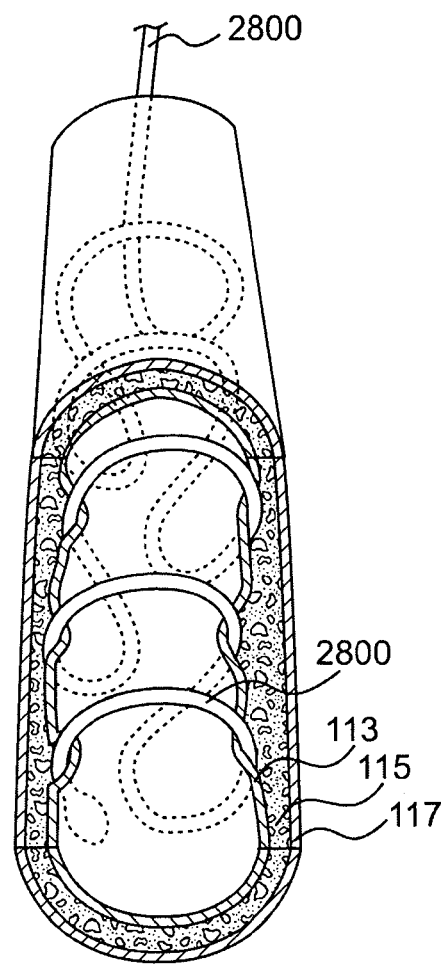
FIG. 28 schematically illustrates an alternative subintimal deployable element.

As an alternative to a lattice structure described previously, the deployable element 2800 may comprise one or more continuous elastic members as shown in FIG. 28. The deployable element 2800 may be released from an exterior containment sheath (not shown) as described previously to expand circumferentially within the subintimal space. As shown in FIG. 28, the deployable element 2800 may comprise a single continuous preformed elastic wire with an atraumatic tip located at the distal end of the wire form to reduce the potential for unintended vessel wall damage. The wire may be made of suitable elastic materials that include but are not limited to nickel titanium, stainless steel, elgiloy, or MP35N. This wire form may include multi-axis bends approximating a sinusoidal pattern bent around a cylinder. The diameter of the cylindrical shape may be selected to match the inside diameter of the artery. The wire form may be restrained in a relatively straight configuration when placed within an exterior containment sheath for advancement through the vasculature to the intended deployment site. Upon withdrawal of the containment sheath, the wire form may assume the aforementioned multi-axis shape.

The deployable element may also be used to orient a re-entry device toward the true lumen distal of the total occlusion. For example, a subintimal device 2900 may have an accessory deployable element 2910 as shown in FIGS. 29A-29D. FIGS. 29B and 29D are cross sectional end views of FIGS. 29A and 29C, respectively. With reference to FIGS. 29A and 29B, the subintimal device 2900 is shown positioned in the subintimal space with the accessory deployable element 2910 having an exposed portion disposed in a recess and a proximally extending portion in a lumen of the subintimal device 2900. With reference to FIGS. 29C and 29D, advancing the proximal portion of the deployable element causes the exposed portion to protrude from a side port 2904 and advance within the subintimal space. The geometry of the deployable element may be a preformed shape such as a U-shape to allow atraumatic expansion within the subintimal space as shown. With the accessory deployable element in the subintimal space as shown, it forms a radial curvature with a concave side that faces the true lumen 116. With the concave side facing the true lumen, a re-entry device may be directed to penetrate the intimal layer into the true lumen as previously described with reference to FIGS. 23A-23E, 24A-24C, and 25.

Occlusion Removal Embodiments

Some of the devices described herein may also be used to facilitate complete or partial removal of a total occlusion, potentially including an inner portion of the arterial wall. FIGS. 30A-30D illustrate an example of this application wherein a delivery device 400 is used to deliver a subintimal device 300 around a total occlusion 120, similar to what is shown and described with reference to FIGS. 4, 4A, 4B and 5. The occlusion is then removed as will be described in more detail.

Figure 30A:
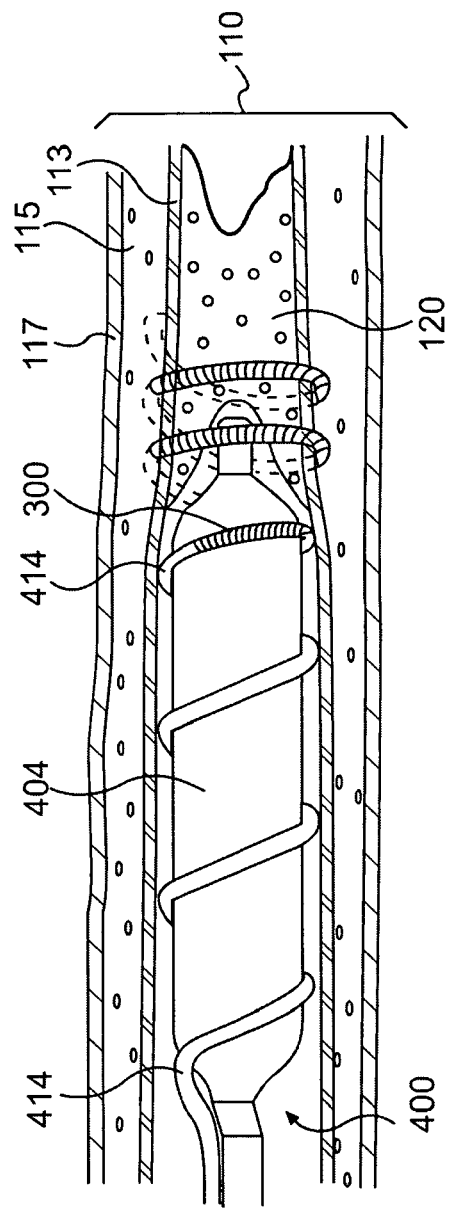
FIGS. 30A-30D and 31A-31B illustrate various devices that facilitate occlusion removal after subintimal delamination.

With reference to FIG. 30A, the delivery device 400 is positioned just proximal of a total occlusion 120. In this position, the balloon 404 may be inflated within the vessel lumen 116 to direct the delivery tube 414 toward the vessel wall 118 at an orientation for the subintimal device 300 to penetrate through the intima 113 at an entry point and into the subintimal space. By virtue of the helical delivery tube 414, the subintimal device 300 is sent on a helical trajectory as it is advanced through delivery tube 414 resulting in deployment of the subintimal device 300 in a helical pattern. As shown, the subintimal device 300 has been advanced through the delivery tube 414 and positioned concentrically outside the total occlusion 120, outside the intimal layer 113, and inside the medial layer 115 in the subintimal space.

Figure 30B:
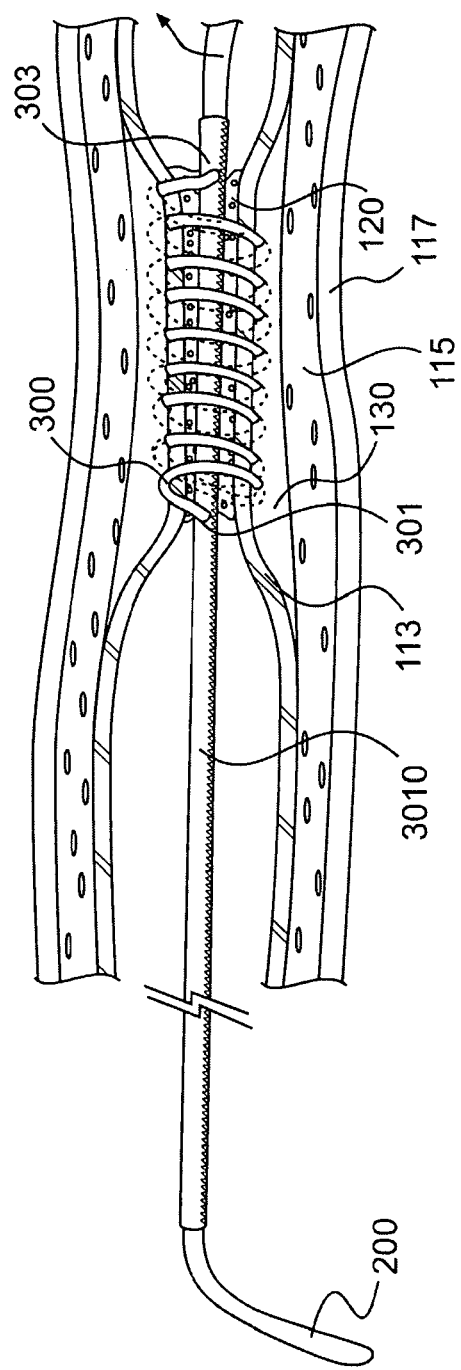

With reference to FIG. 30B, a subintimal device capture catheter 3010 is positioned across the chronic total occlusion 120 over a conventional guide wire 700 and within the subintimal device 300. The proximal 301 and distal 303 ends of the subintimal device 300 have been captured and rotated by capture device 3010 so as to reduce the outside diameter and contain the lesion 120 and intima 113 within the coils of the subintimal device 300.

Figure 30C:
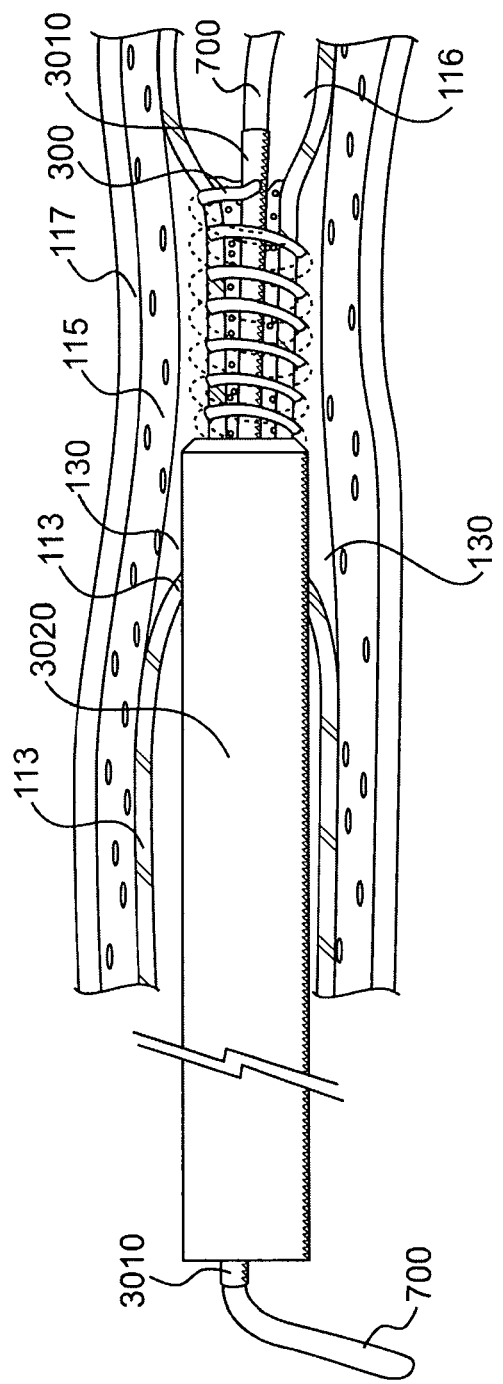
Figure 30D:
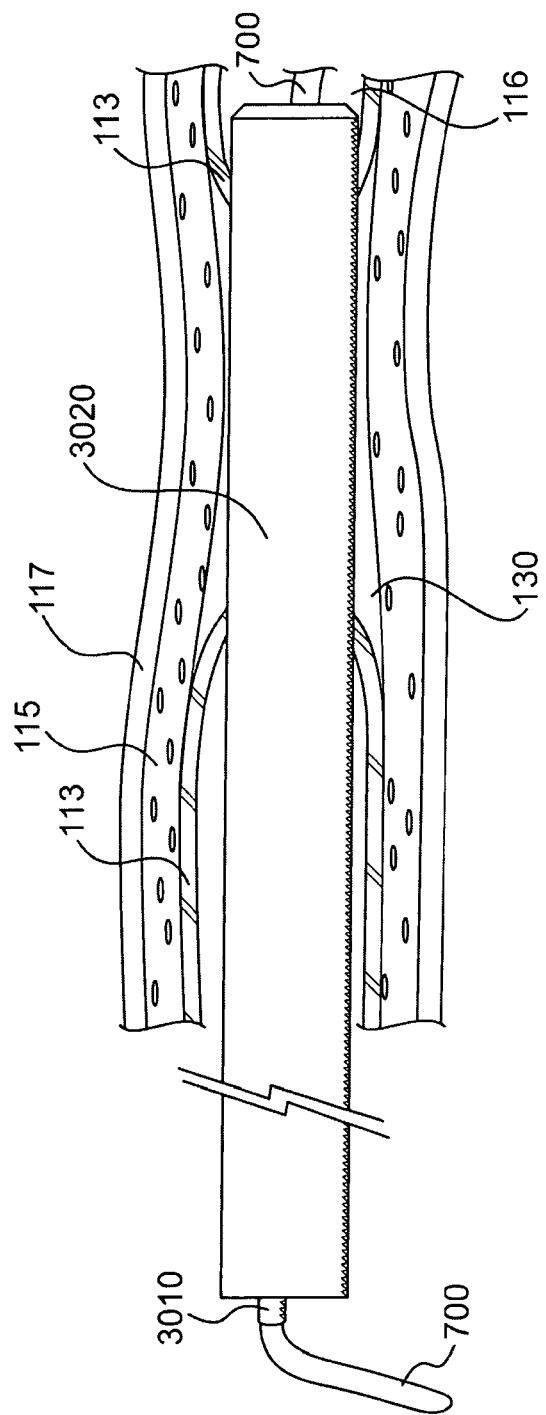

With reference to FIG. 30C, a tubular cutting device 3020 with a sharpened leading edge may be advanced over the subintimal device 300 and the capture device 3010 to engage and cut the intimal layer 113 with the total occlusion 120 therein. With reference to FIG. 30D, further advancement of the cutting device 3020 cuts and separates the diseased portion including the total occlusion and surrounding intima from the remainder of the artery. Proximal withdrawal of the device from the artery results in removal of the total occlusion and a patent true lumen 116. The occlusion 120 may be removed through the percutaneous intravascular access site or a surgical cut down may be performed to facilitate removal if the occlusion is too large for removal through the percutaneous access site. Alternatively, to reduce the size of the occlusion and thus facilitate removal through the percutaneous access site, a maceration mechanism may be employed to macerate the occlusion prior to removal.

Figure 31A:
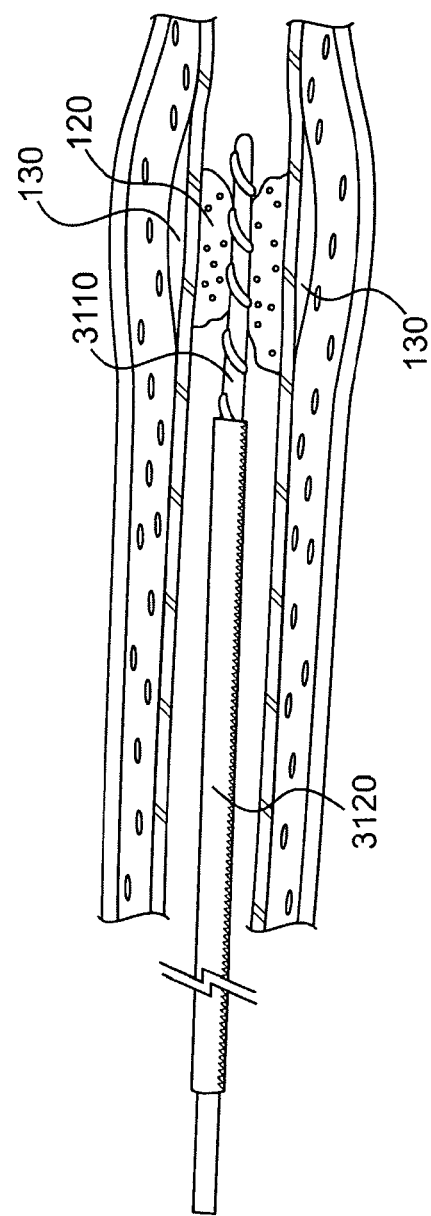
Figure 31B:
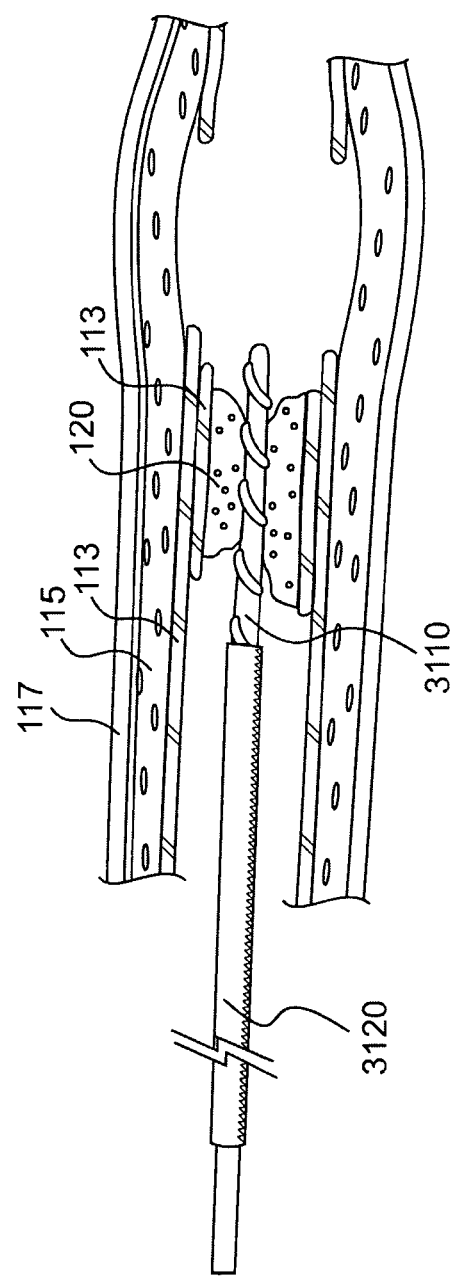

In addition or as an alternative, a corkscrew-type device 3110 may be used to grasp and pull the total occlusion 120 for removal as shown in FIGS. 31A and 31B. It is contemplated that corkscrew-type device 3110 may be used in combination with the devices described with reference to FIGS. 30A-30D which are not shown for sake of clarity. With reference to FIG. 31A, the corkscrew device 3110 is shown with an exterior sheath 3120. The corkscrew device 3110 is shown engaging occlusion 120 after delamination of the intimal layer 113 has been performed by the aforementioned methods and devices. FIG. 31B shows removal of the occlusion 120 and a portion of the intimal layer 113 through axial withdrawal of the corkscrew device 3110.

Alternative Bypass Embodiment

Figure 32C:
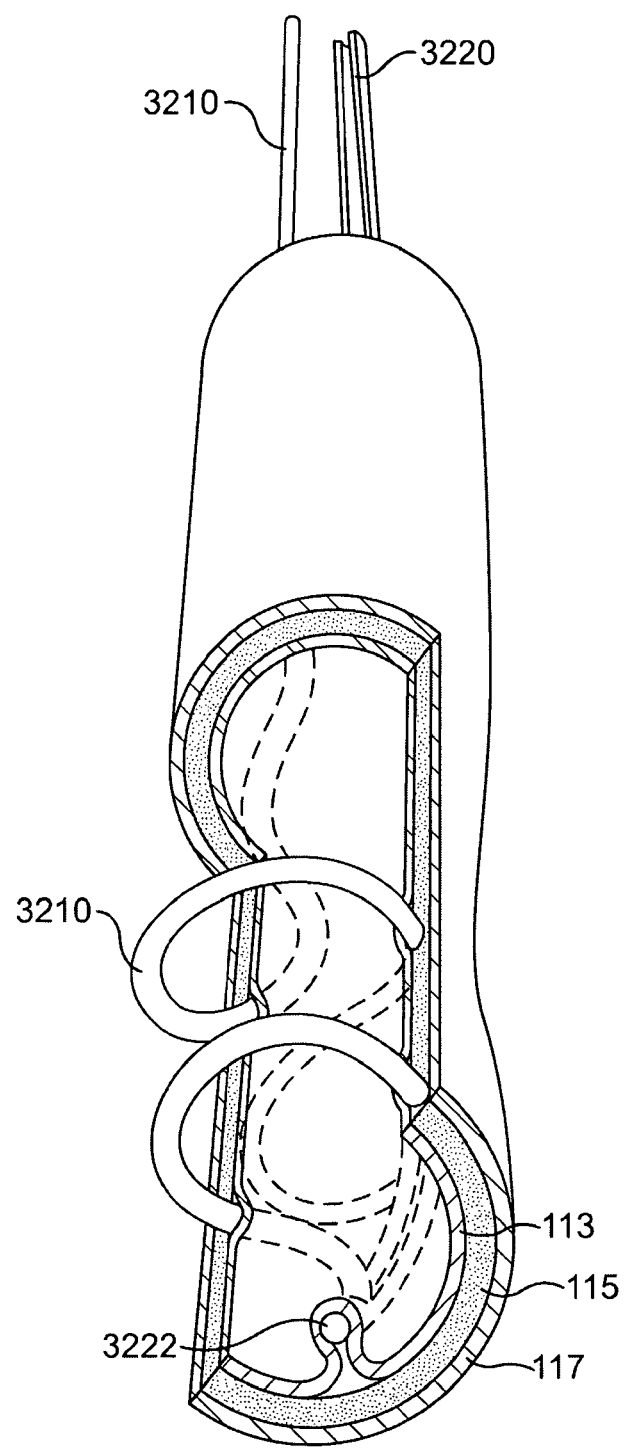

FIGS. 32A-32E illustrate an alternative system for bypassing a total occlusion. With reference to FIG. 32A, a subintimal device 3200 is shown in the deployed configuration. The subintimal device 3200 includes an elastic wire 3210 with a distal form similar to the elastic wire form 2800 described with reference to FIG. 28, except with fewer sinusoidal turns. The subintimal device also includes a crescent-shaped or semi-circular delivery shaft 3220 and a retractable constraining sheath 3230. As seen in FIG. 32B, which is a cross-sectional view taken along line A-A in FIG. 32A, the wire 3210 resides in the recess of the semi-circular delivery shaft 3220 over which the constraining sheath 3230 is disposed. As an alternative, the constraining sheath 3230 may be disposed about the wire 3210 only and may reside in the recess of the delivery shaft 3220, provided that the constraining sheath 3230 is sufficiently stiff to at least partially straighten the formed wire 3210. The distal end of the wire 3210 is connected to a blunt tip 3222 of the shaft 3220. The wire 3210 and the semi-circular shaft 3220 may be formed of a resilient metallic material such as nickel titanium, stainless steel, elgiloy, or MP35N, and the sheath 3230 may be formed of a flexible polymeric material such as a polyether-block-amide (e.g., Pebax) lined with PTFE (e.g., Teflon).

Pulling the wire 3210 proximally relative to the shaft 3220 and advancing the sheath 3230 over the wire form constrains the wire form in the recess and renders the device 3200 suitable for atraumatic passage through the subintimal space. Once the device 3200 is positioned across the total occlusion within the subintimal space, the sheath 3230 may be retracted relative to the shaft 3220 to release the formed portion of the wire 3210. Releasing the wire form causes it to extend circumferentially around the occlusion in the subintimal space as shown in FIG. 32C. Once the wire form is fully deployed in the subintimal space, the sheath may be completely removed.

Figures 32D, 32E:
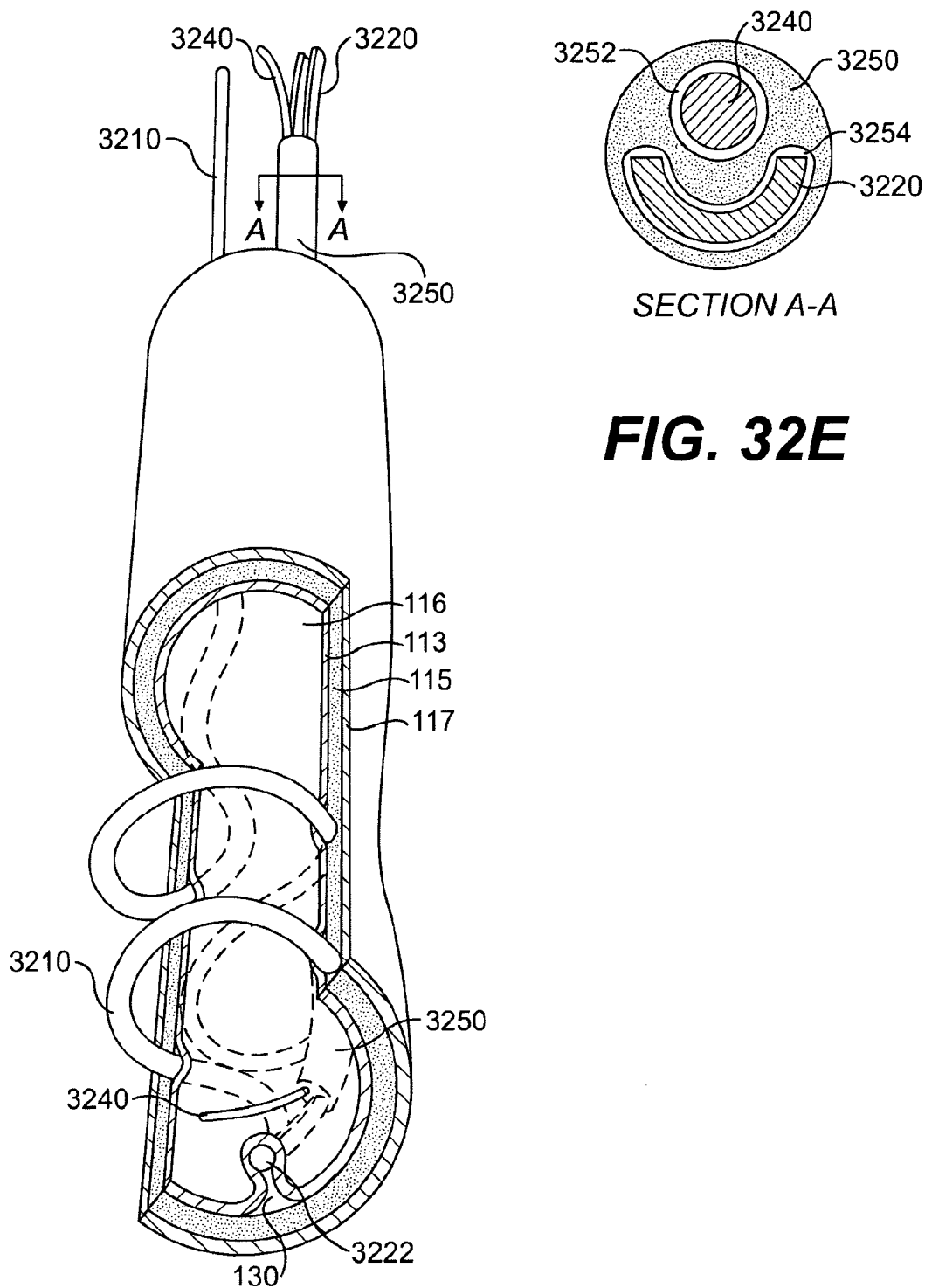

As shown in FIG. 32D, with the wire form 3210 deployed in the subintimal space and with the sheath 3230 removed from the shaft 3220, a dual lumen re-entry delivery catheter 3250 may be advance over the shaft 3220. As seen in FIG. 32E, which is a cross-sectional view taken along line A-A in FIG. 32D), the delivery catheter 3250 includes a crescent-shaped or semi-circular lumen 3254 that accommodates the shaft 3220 extending therethrough. The delivery catheter 3250 also includes a circular lumen 3252 that accommodates a re-entry device 3240 extending therethrough. The delivery catheter 3250 may comprise a dual lumen polymeric extrusion such as polyether-block-amid (e.g., Pebax) and the re-entry device 3240 may be the same or similar to the re-entry devices described previously herein.

Alternatively, the delivery catheter 3250 may comprise two coaxial tubes including an elongate inner tube disposed in an elongate outer tube. The inner tube is configured to accommodate a re-entry device. The annular lumen defined between the inner tube and the outer tube is configured to accommodate semicircular delivery shaft 3220. At the distal end of the delivery catheter 3250, the inner tube may be tacked to the inside of the outer tube using a heating forming process where a portion of the outside circumference of the inner tube is thermally fused to the inside circumference of the outer tube thus creating a cross section similar to that shown in FIG. 32E over the heat formed area Outside the heat formed area, the inner and outer tubes may remain coaxial and un-fused.

As described previously, the concave side of the wire form faces the true lumen, and with the fixed attachment of the wire 3210 to the tip 3222 of the shaft 3220, the concave side of the semi-circular shaft 3220 also faces the true lumen. This feature may be used to facilitate orientation of a re-entry device toward the true lumen. For example, because lumen 3252 of the delivery catheter 3250 has a mating or keyed geometry with the semi-circular shaft 3220, and because the concave side of the semi-circular shaft 3220 is oriented toward the true lumen, the re-entry device lumen 3252 may be oriented toward the true lumen as well. With this in mind, any of the re-entry device orientation methods described with reference to FIGS. 23A-23E may be employed. As shown in FIG. 32D, the distal end of the semi-circular shaft 3220 has a curvature with a concave side facing the true lumen which may be used in concert with a curved re-entry device 3240. Once orientation is established, the re-entry device 3240 may penetrate the intimal layer 113 and re-enter the true lumen as shown.

Orienting Device Introduced Through Subintimal Guide Catheter Embodiment

FIGS. 33A-33E schematically illustrate an embodiment using one or more subintimal guide catheters 3310/3320 to introduce an orienting device 3330. These Figures show a window cut-away in the outer layer of the vascular wall for purposes of illustration. In this embodiment, which is an alternative bypass embodiment in some aspects, a subintimal crossing device 300 with or without a guide wire lumen (shown) and having a bulbous tip 310 (e.g., 0.038 in. diameter olive shaped weld ball) is used to safely cross the subintimal space by blunt dissection as described elsewhere herein.

Figure 33A:
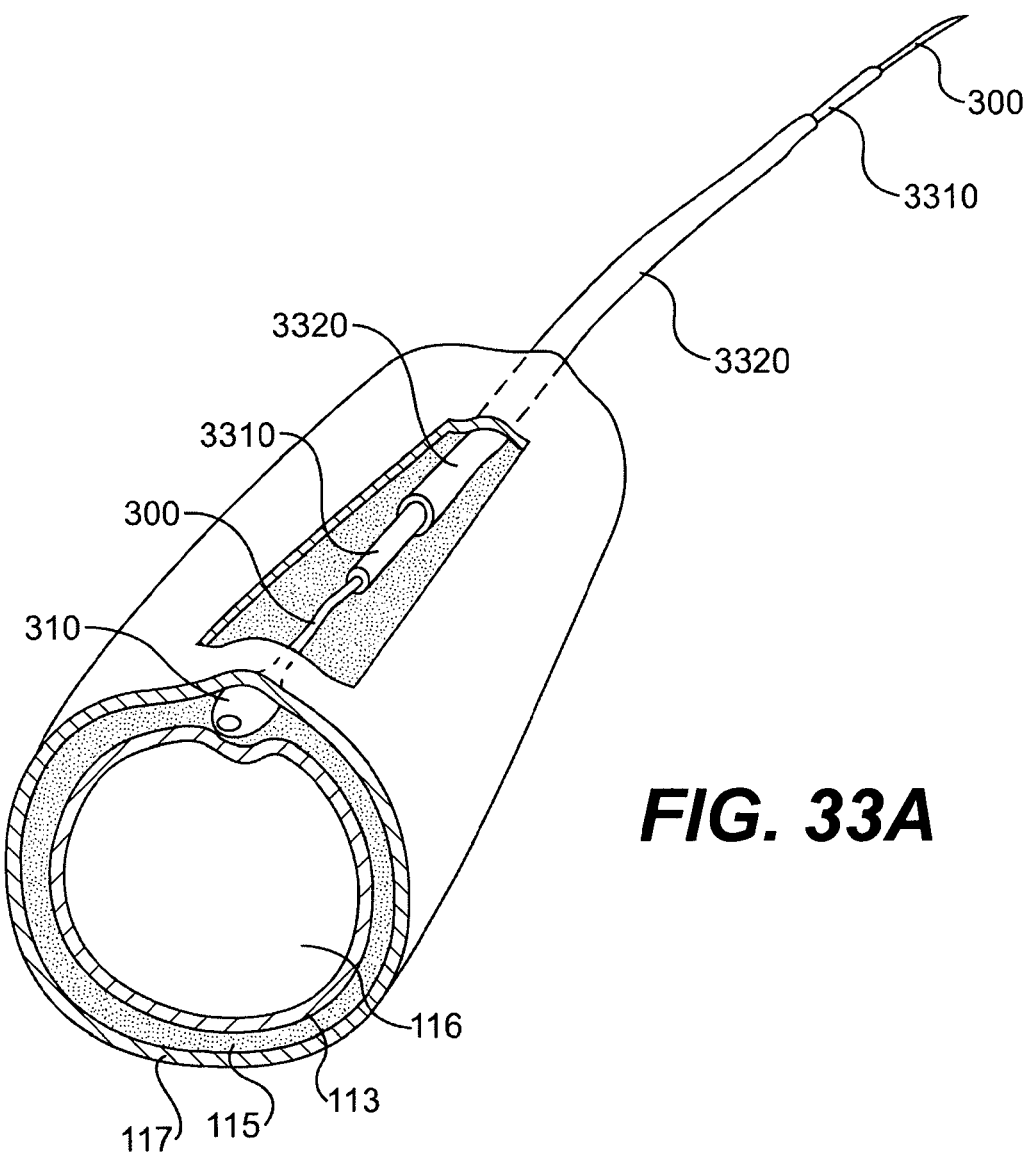
FIGS. 33A-33E schematically illustrate an embodiment using one or more subintimal guide catheters to introduce an orienting device.
Figure 33B:
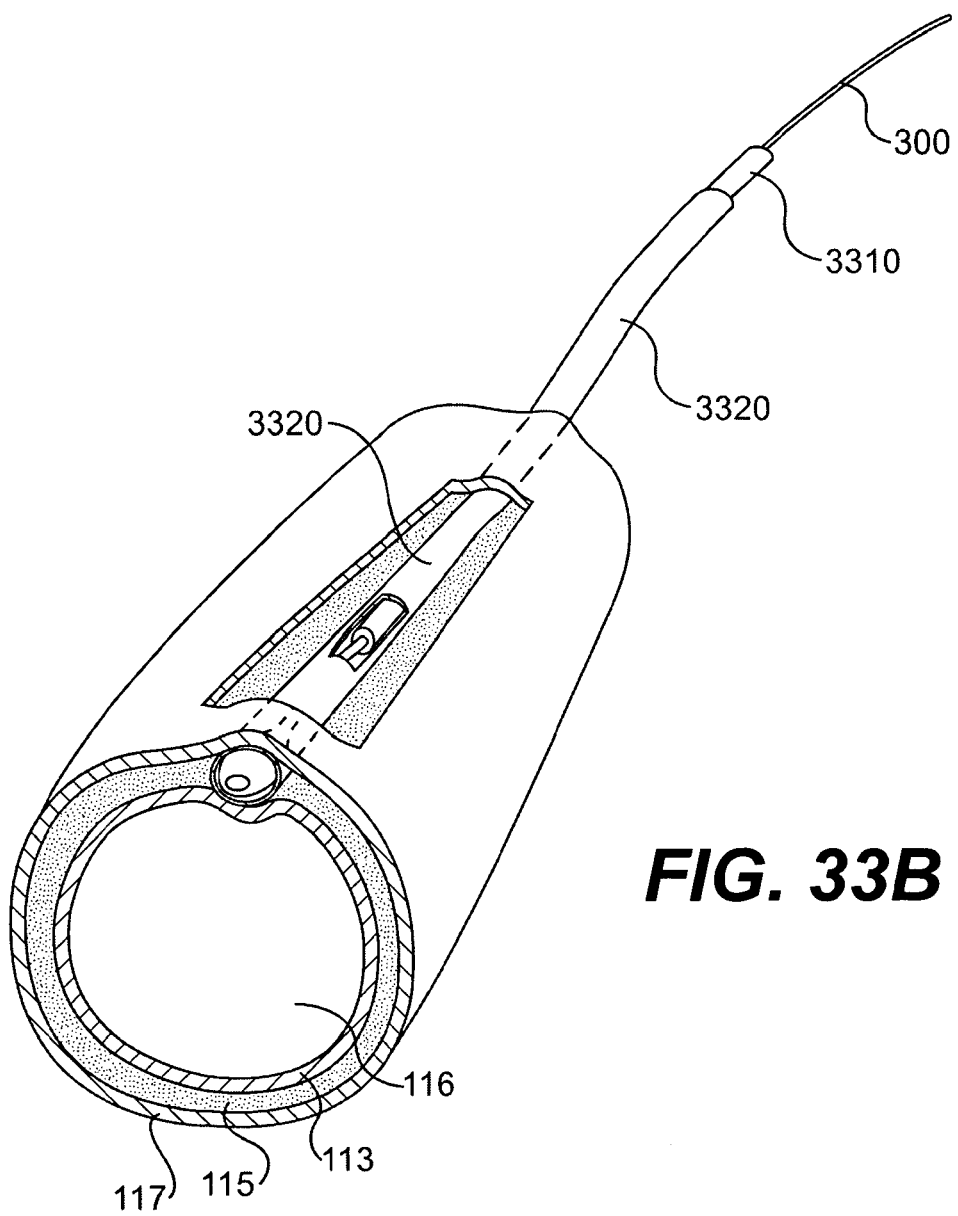

As shown in FIG. 33A, a first (inner) sheath 3310 having an inside diameter (e.g., 0.018 inches) slightly larger than the outside diameter (e.g., 0.014-0.016 inches) of the shaft of the crossing device 300 may be advanced by pushing and back-and-forth rotation over the crossing device 300 and through the subintimal space up to the bulbous tip 310 located adjacent the distal end of the occlusion (not shown). Once in place, a second (outer) sheath 3320 having an outside diameter of 0.050 inches, for example, and an inside diameter (e.g., 0.040 inches) slightly larger than the outside diameter (e.g., 0.037 inches) of the inner sheath 3310 and slightly larger than the outside diameter of the tip 310 may be advanced by pushing and back-and-forth rotation over the inner sheath 3310 up to the bulbous tip 310 as shown in FIG. 33B. In this Figure, a window cut-away is shown in the distal portion of the outer sheath 3320 for purposes of illustration. Once the outer sheath 3320 is in this position, the subintimal crossing device 300 and the inner sheath 3310 may be removed proximally through the outer sheath. Although the outer sheath 3320 may be advanced over the subintimal crossing device 300 without the need for inner sheath 3310, the inner sheath 3310 provides step-wise increase in dissection diameter making traversal easier. The inner sheath 3310 may be formed of a braid reinforced polymeric construction (e.g., 55 D polyether block amide) with an atraumatic tip (e.g., unreinforced 40 D polyether block amide). The outer sheath 3320 may be formed of a more rigid polymer (e.g. 72 D polyether block amide) and may optionally include a braid composite construction. Braid reinforced construction provides enhances push and torque, and it is believed that rotation of the sheaths 3310/3320 enhances the ability to cross and delaminate across the subintimal path.

Figure 33C:
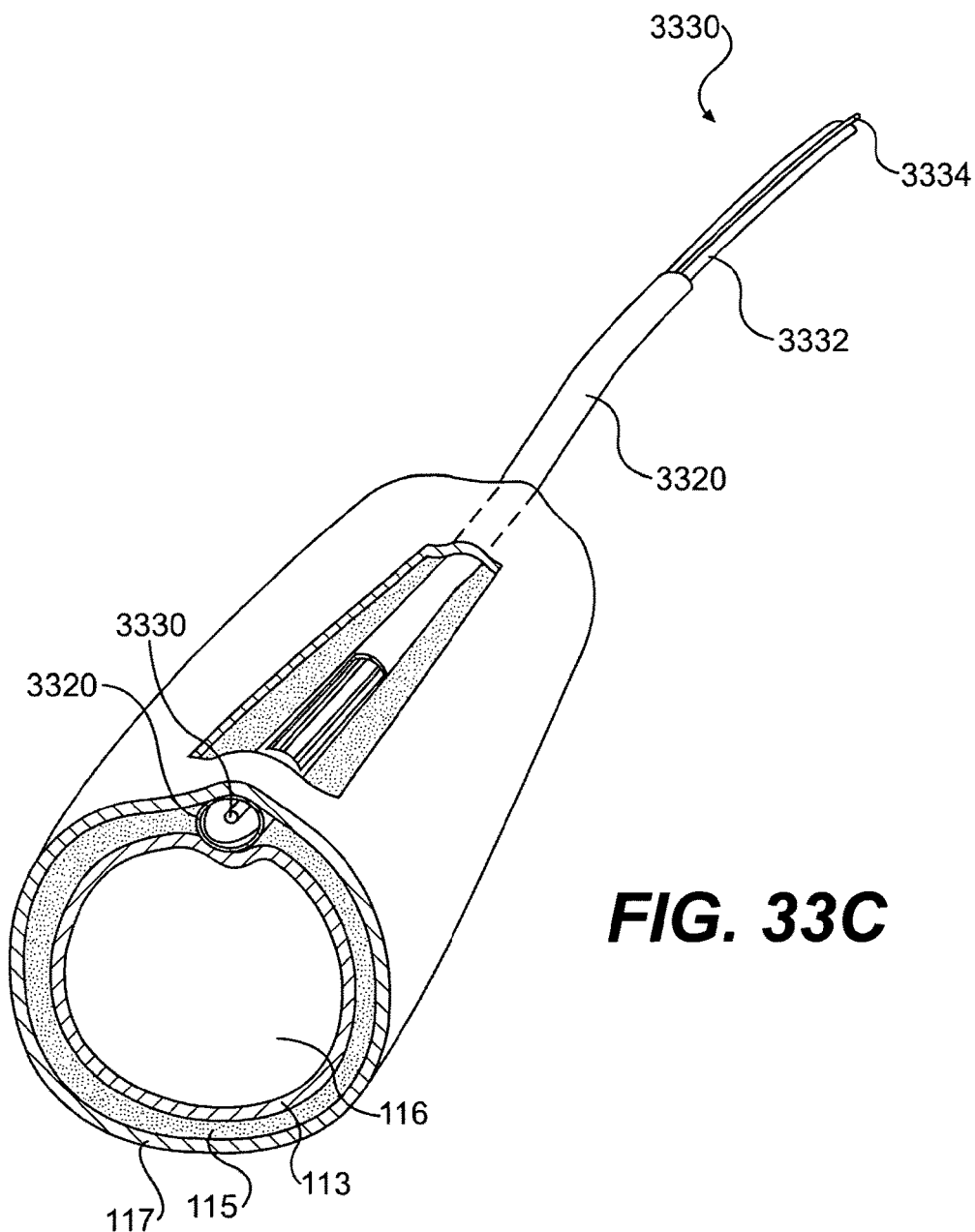

With the outer sheath 3320 in place and providing a protected path across the occlusion within the subintimal space, an orienting device 3330 may be inserted into the sheath 3320 to the distal end thereof as shown in FIG. 33C. In this Figure, a window cut-away is shown in the distal portion of the outer sheath 3320 for purposes of illustration. FIG. 33C shows the orienting device 3330 in the delivery configuration with the orienting element collapsed and FIG.

33D shows the orienting device 3330 in the deployed configuration with the orienting element expanded.

Figure 33D:
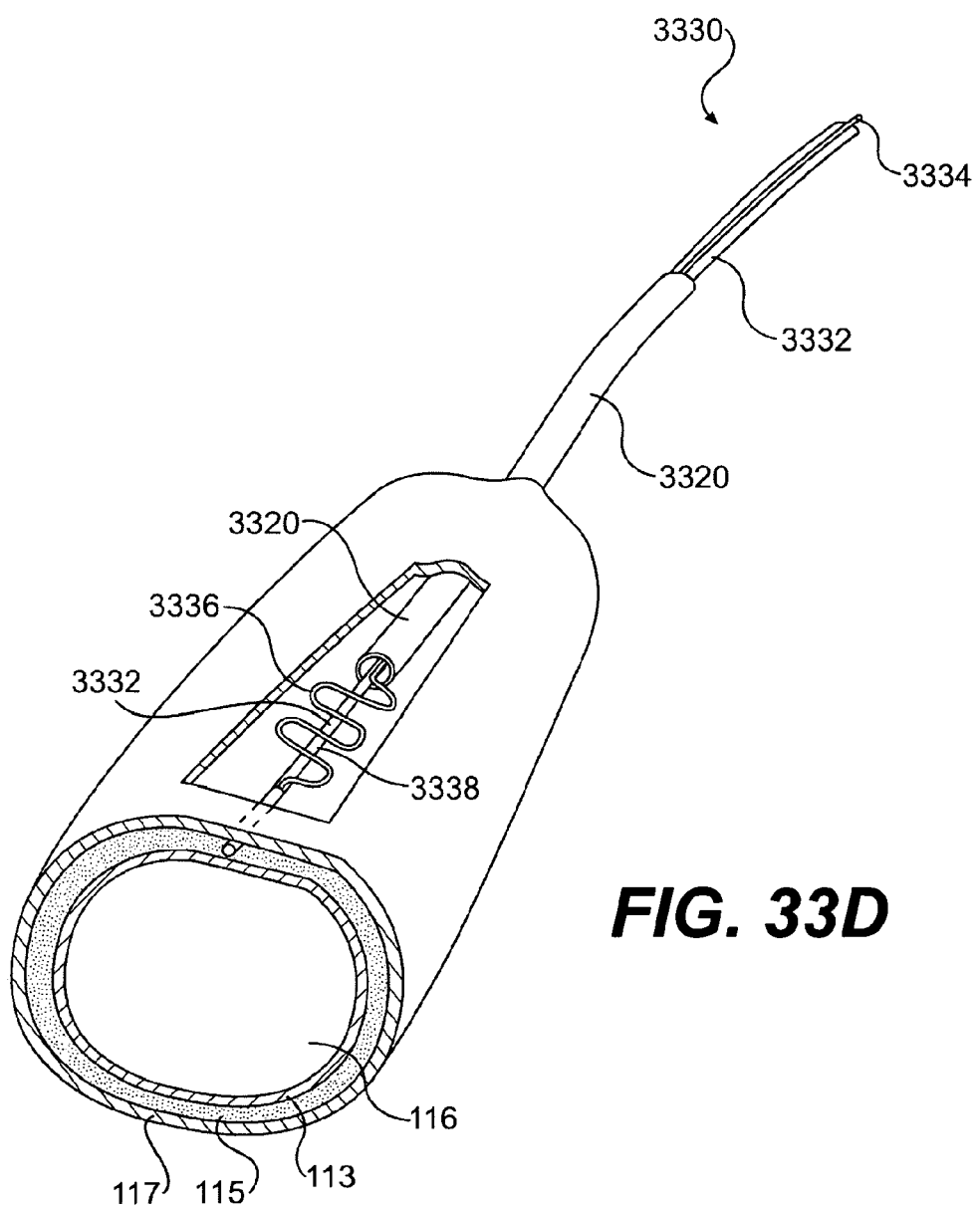

The orienting device 3330 shown in FIG. 33D is similar to the orienting device 3200 shown in FIG. 32A. The orienting device 3330 may include a tubular shaft 3332 with a wire 3334 disposed therein. The tubular shaft 3332 may comprise a polymeric tube with a wire ribbon (e.g., SST) embedded therein to add stiffness for pushability. The tubular shaft 3332 includes a lumen extending therethrough, and the distal end of the lumen is directed at an angle to a side facing exit port 3338 located proximate the orienting element 3336. The distal end of the wire 3334 may include an orienting element 3336 comprising, for example, a preformed planar sinusoid, referred to as a wire form. The wire 3334 and the wire form 3336 may comprise a superelastic metal alloy such as NiTi, for example, and the wire form 3336 may be formed by heat setting. To deploy the orienting element 3336, the outer sheath 3320 may be pulled proximally and the shaft 3332 may be pushed distally in an alternating fashion until the entire wire form 3336 is within the subintimal space.

The side port 3338 is oriented at a right angle to the plane of the orienting element 3336. With this arrangement, the side port 3338 is either directed toward the vascular true lumen 116 or 180 degrees away from the vascular true lumen 116. Radiographic visualization or other techniques as described elsewhere herein may be used to determine if the port 3338 is directed toward or away from the true lumen 116. If the port 3338 is directed away from the true lumen 116, the orienting device may be retracted, rotated 180 degrees, and re-deployed to point the port 3338 toward the true lumen 116. A re-entry device as described elsewhere herein may then be advanced through the lumen of the tubular shaft 3332, through the vascular wall and into the true lumen 116.

Figure 33E:
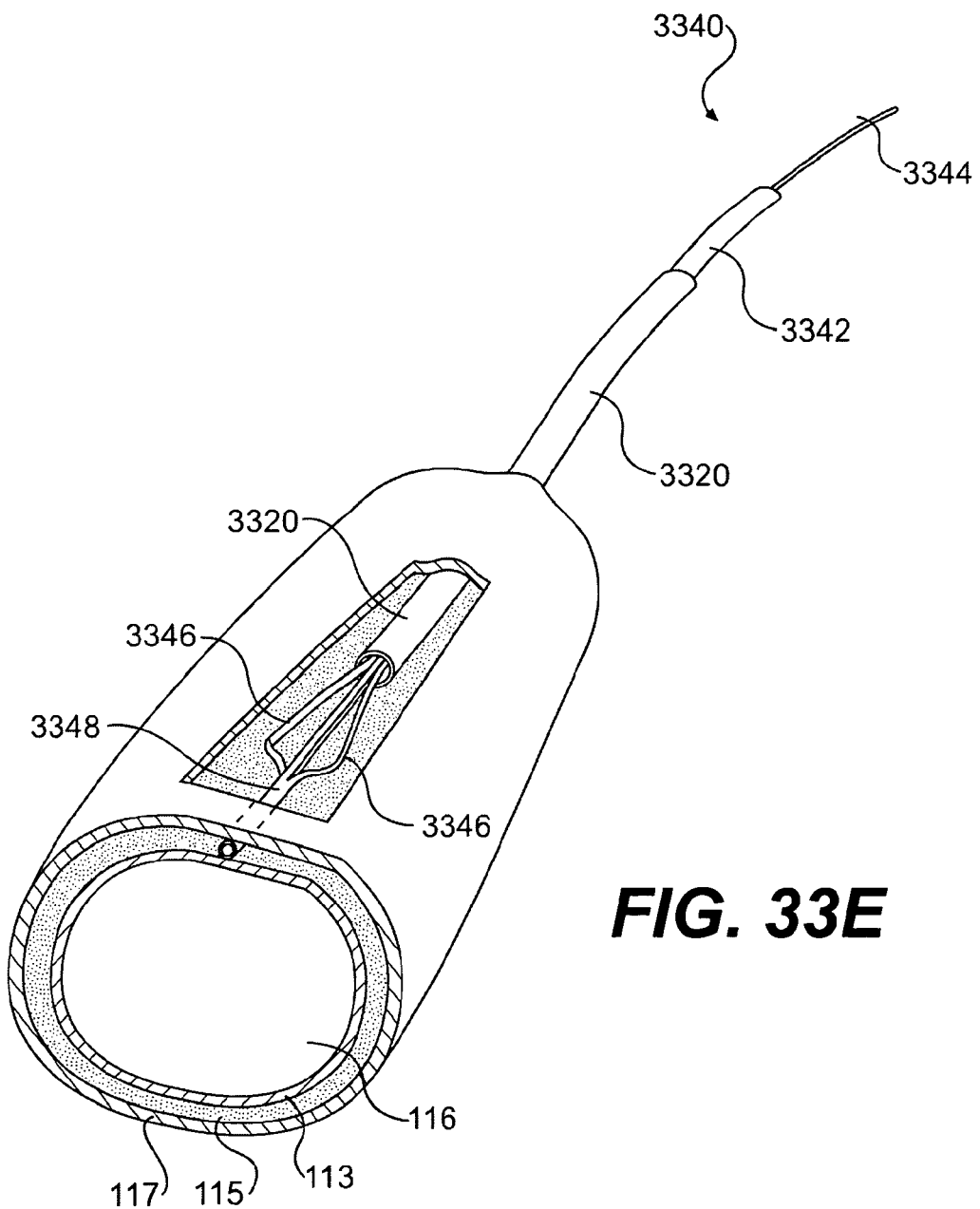

As an alternative to orienting device 3330 shown in FIG. 33D, orienting device 3340 shown in FIG. 33E may be employed in substantially the same manner. Orienting device 3340 includes an outer tube 3342 and an inner tube 3344. The outer tube 3342 may be formed of a superelastic metal alloy (e.g., NiTi), and a distal portion of the outer tube 3342 may be cut (e.g., using laser cutting techniques) to form slots to define two wings 3346 that hinge outward in a planar fashion as shown. The inner tube 3344 extends through the lumen of the outer tube 3342 and is attached distally to the distal end of the outer tube 3342. Inner tube 3344 is similar in design and function as tubular shaft 3332, and includes a distal side port 3348 to accommodate a re-entry device as described with reference thereto. Alternatively, a flap port may be used as will be described in more detail hereinafter.

Figure 34E:
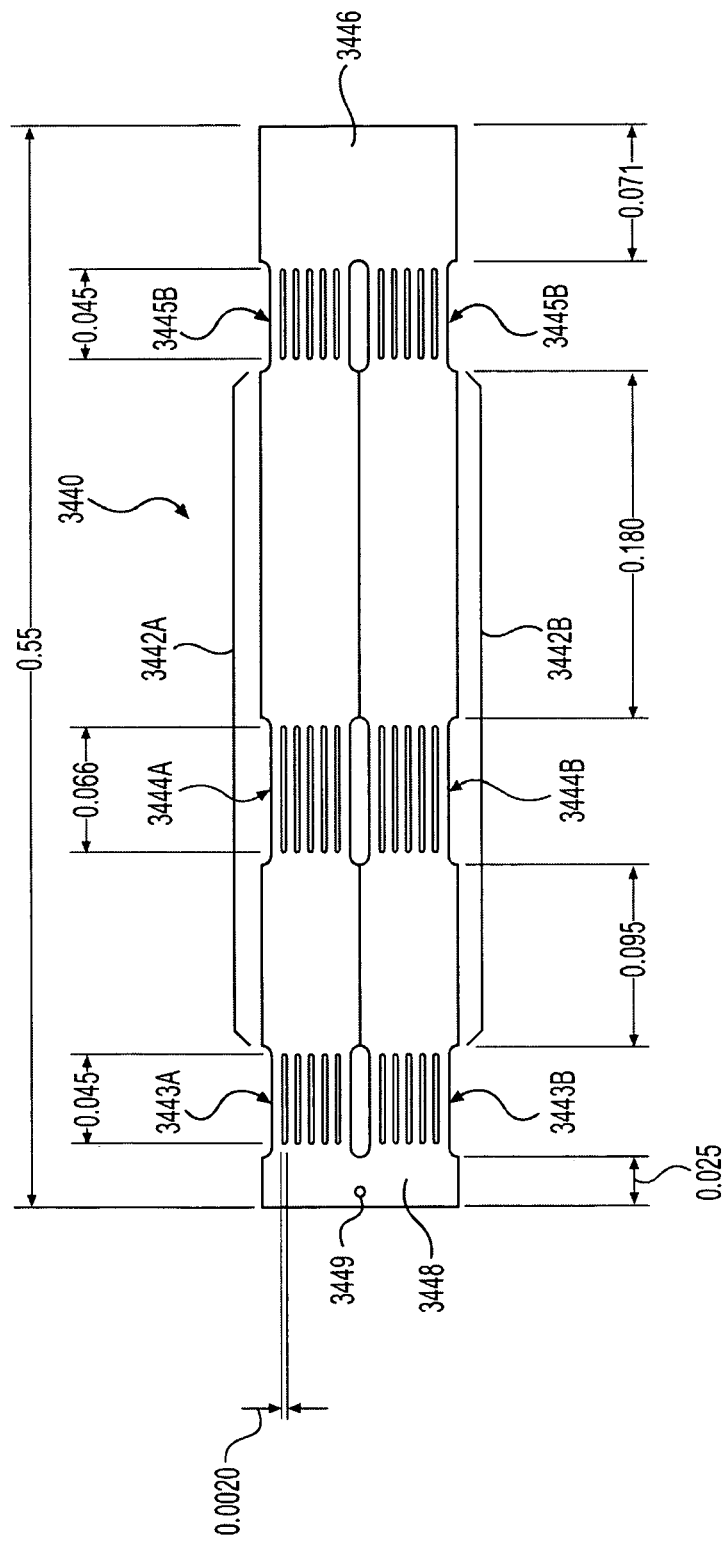

Orienting Device Introduced Over Subintimal Crossing Device or Guide Wire Embodiment FIGS. 34A-34H schematically illustrate an embodiment using a subintimal crossing device or guide wire to introduce an orienting device 3400. In this embodiment, the orienting device 3400 is designed to accommodate a subintimal crossing device or guide wire therein, thus negating the need for the subintimal guide catheters described previously. With specific reference to FIG. 34A, a detailed view of a distal portion of the orienting device 3400 is shown. FIG. 34B(1) is a cross-sectional view taken along line A-A in FIG. 34A, and FIG. 34B(2) is a cross-sectional view taken along line B-B in FIG. 34A. The orienting device 3400 includes an elongate outer tubular shaft 3410 with a distal end connected to an orienting element 3440. An elongate inner tubular shaft 3420 extends through the outer shaft 3410 and orienting element 3440. The distal end of the inner shaft 3420 is connected to the distal end of the orienting element 3440, as is a distal atraumatic tubular tip 3450. A low friction liner 3430 may extend through the lumen of the inner shaft 3420 to facilitate smooth passage of devices therein.

The outer shaft 3410 may comprise, for example, a polymeric tube 3412 that may be reinforced with an embedded braid or wire ribbon. The inner shaft 3420 may comprise a metallic tube 3422 (e.g., NiTi) with a solid tubular proximal segment and a spiral cut 3424 distal segment for added flexibility and torqueability. The distal portion of the inner shaft 3420 may include an inwardly inclined flap 3426. As seen in FIG. 34B(1), the flap 3426 extends into the lumen of the inner shaft 3420 and operates to (1) direct front loaded devices (e.g., re-entry device) out the side port 3425 of the inner shaft 3420 adjacent the orienting element 3440; and (2) direct back loaded devices (e.g., subintimal crossing device or guide wire) down the lumen of the proximal segment 3422 of the inner shaft 3420 while preventing back loaded devices from exiting the side port 3425. A semi-circular slot 3428 may be formed to accommodate the end of the flap 3426 to prevent the edge of the flap 3426 from snagging on devices passing by. The cuts may be formed by laser cutting or the like and the flap may be biased inwardly by heat setting.

With reference to FIG. 34C, the inner shaft 3420 may have an overall length of approximately 135 cm for coronary applications, with a spiral cut 3424 distal segment length of approximately 35 cm, for example. With reference to FIG. 34D, which is a detailed view of a distal portion of the inner shaft 3420, the cut pattern is illustrated as if the tube were laid flat with dimensions given in inches unless otherwise noted. The spiral cut 3424 may terminate proximal of the side port 3425 and flap 3426. A hinge slot 3427 may be provided to allow the flap 3426 to hinge when devices are back loaded as described previously. A semi-circular slot 3428 may be provided to accommodate the end of the flap as described previously. A hole 3429 may be used to provide connection to the distal end of the orienting element (not shown) by pinning or welding, for example.

With reference to FIGS. 34A and 34E, the orienting element 3440 may comprise a metallic tube (e.g., NiTi) with cuts made to define two wings 3442A and 3442B. In FIG. 34E, the cut pattern of the orienting element 3440 is shown as if the tube were laid flat with dimensions given in inches unless otherwise noted. The cuts are made to define two separate wings 3442A and 3442B, with three hinge points 3443, 3444 and 3445 per wing 3442. The proximal end 3446 of the orienting element 3440 is connected to a flared end of the outer shaft 3410, and the distal end 3448 is connected to the distal end of the inner shaft 3420 and the proximal end of the tubular tip 3450. By contracting the proximal end 3446 toward the distal end 3448, the proximal lunge 3445 and the distal hinge 3443 flex outwardly to extend each wing 3442 outwardly, with the center hinge 3444 at the apex of each wing 3442.

The distal tip 3450 may comprise a relatively soft polymeric tube segment, optionally loaded with radiopaque material. The inner liner 3430 may comprise a tubular extrusion 3432 or internal coating made of a low friction material such as high density polyethylene (HDPE) or polytetrafluoroethylene (PTFE).

Figure 34F:
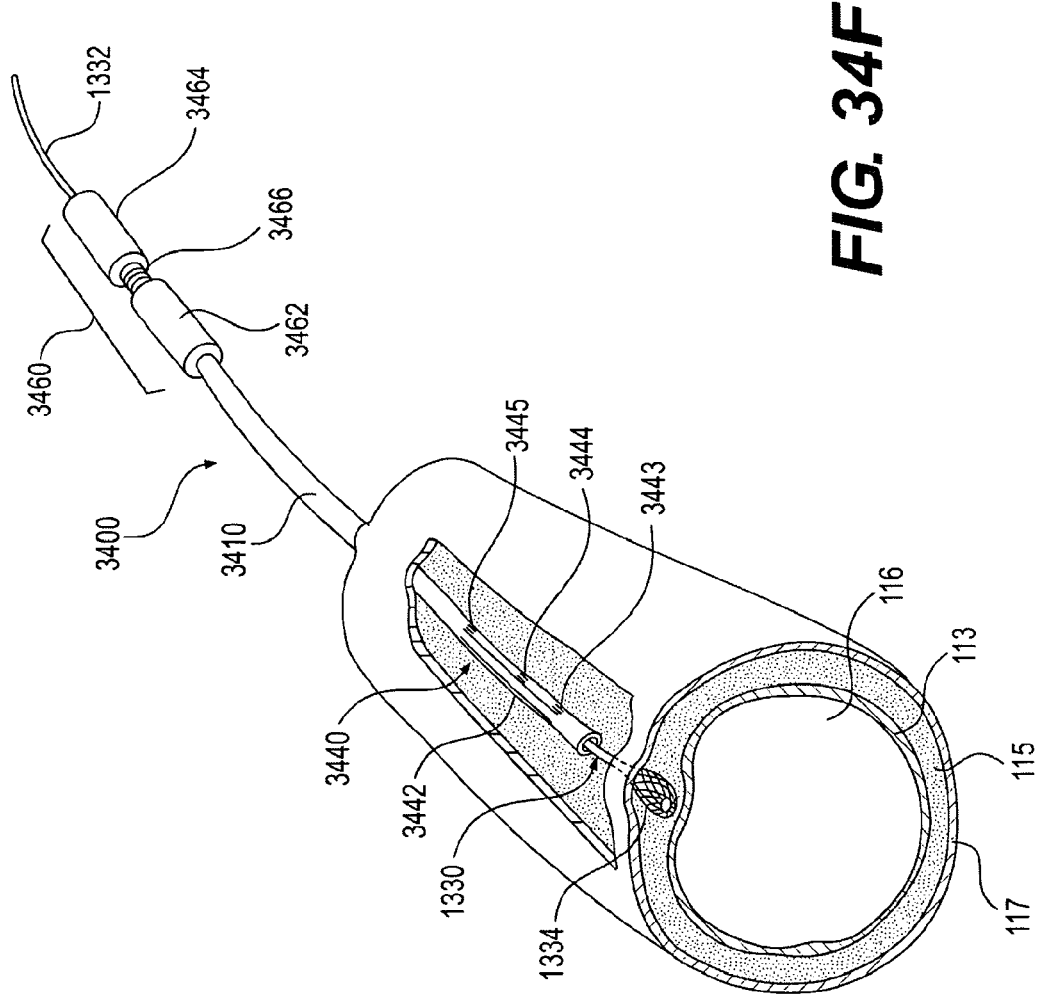
Figure 34G:
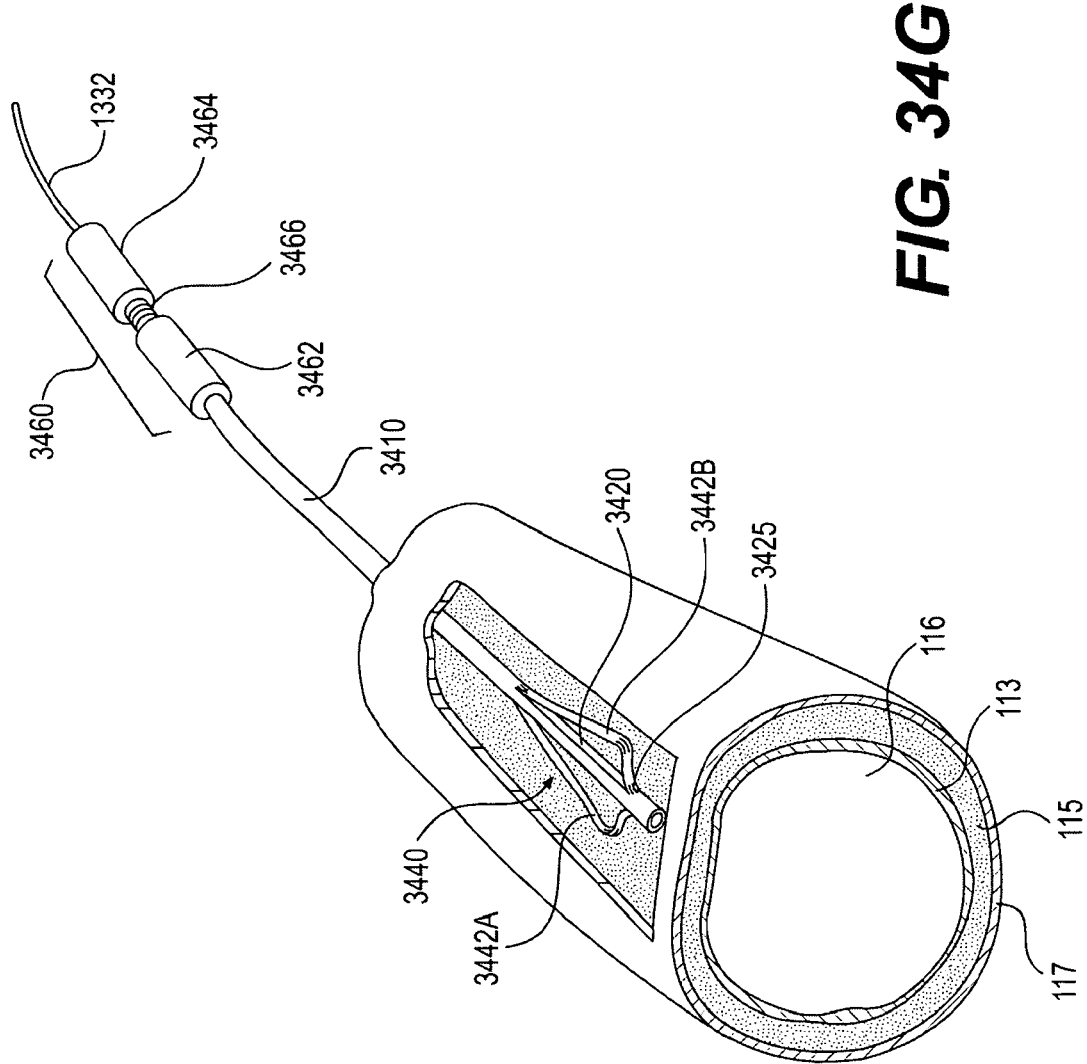
Figure 34H:
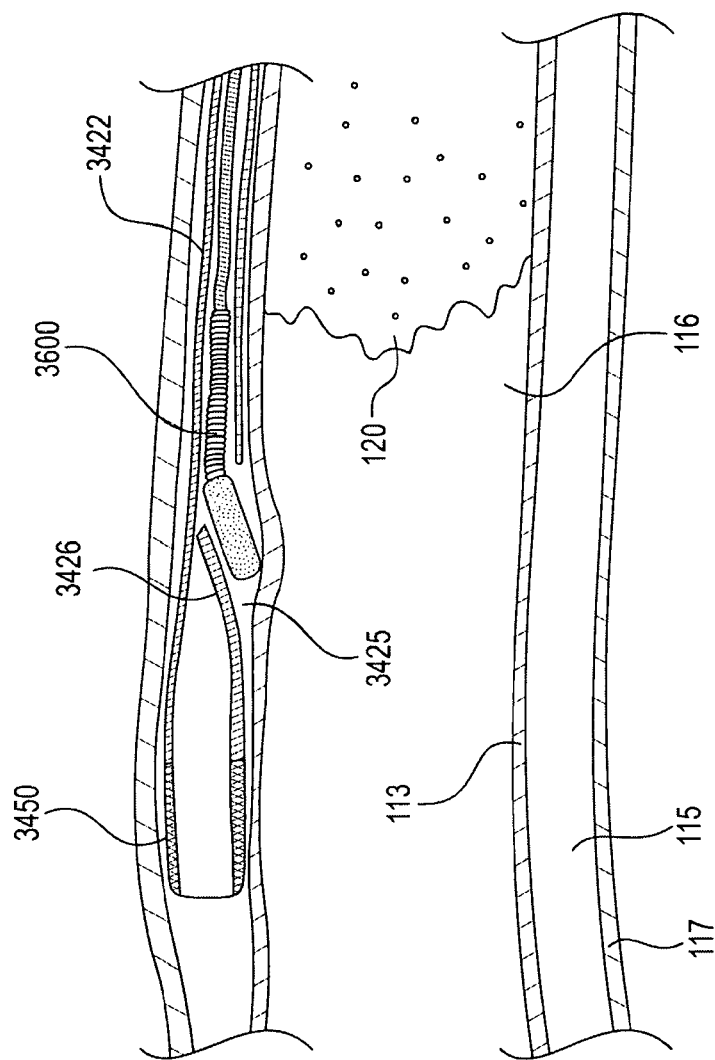

FIGS. 34F-34H schematically illustrate a method of using the orienting device 3400 described above. As mentioned previously, orienting device 3400 is designed to be advanced over a subintimal crossing device or guide wire, but subintimal guiding catheters may be used in addition to or in place of a crossing device or guide wire. For sake of illustration, the orienting device 3400 is shown over subintimal crossing device 1330 having an expandable and collapsible tip 1334 at the distal end of an elongate shaft 1332, but the orienting device 3400 may also be advanced over a conventional guide wire (not shown), another subintimal device, or another similarly sized device advanced across the occlusion within the subintimal space. Using a device with a collapsible tip (e.g., subintimal crossing device 1330) or a device without an enlarged tip allows it to be removed through the center lumen of the orienting device 3400 such that a re-entry device may be subsequently advanced through the same lumen, thus using a single lumen for dual purposes and conserving device profile.

With reference to FIG. 34F, once the subintimal crossing device 1330 extends across the occlusion within the subintimal space such that the tip 1334 is adjacent the distal end of the occlusion, the orienting device 3400 may be back-loaded (direction shown in FIG. 34B(1)) over the subintimal crossing device 1330 such that the shaft 1332 of the crossing device 1330 deflects the flap 3426 outwardly and extends through the center lumen of the orienting device 3400. The orienting device 3400 may then be advanced over the subintimal crossing device 1330 until the distal end of the orienting device is adjacent the distal end of the occlusion. The tip 1334 of the subintimal crossing device 1330 may then be collapsed and withdrawn proximally.

With reference to FIG. 34G, the orienting element 3440 may be expanded to extend the wings 3442A and 3442B in a substantially planar manner as shown. To facilitate expansion and contraction of the orienting element 3440, an actuation mechanism 3460 may be used to push the outer shaft 3410 and pull the inner shaft 3420 relative to each other to cause expansion, or pull the outer shaft 3410 and push the inner shaft 3420 relative to each other to cause retraction. The actuation mechanism may comprise, for example, a fixed handle 3462 fixedly connected to the proximal end of the outer shaft 3410, a rotatable handle 3464 rotatably connected to the proximal end of inner shaft 3420, and a threaded shaft fixedly connected to rotatable handle 3464 that engages internal threads (not visible) in the fixed handle 3462. The rotatable handle 3464 may engage a collar (not visible) on the proximal end of the inner shaft 3420 that permits relative rotation but prevents relative axial motion and therefore causes axial displacement of the inner shaft 3420 upon rotation of the rotatable handle 3464.

With continued reference to FIG. 34G and additional reference to FIG. 34H, the side port 3425 is either directed toward the vascular true lumen 116 or 180 degrees away from the vascular true lumen 116. Radiographic visualization or other techniques as described elsewhere herein may be used to determine if the port 3425 is directed toward or away from the true lumen 116. If the port 3425 is directed away from the true lumen 116, the orienting device 3400 may be retracted, rotated 180 degrees, and re-deployed to direct the port 3425 toward the true lumen 116. A re-entry device 3600 may then be front-loaded (direction shown in FIG. 34B(1)) through the center lumen of the orienting device 3400. Although re-entry device 3600 is shown for purposes of illustration, other re-entry devices may be used as described elsewhere herein. As the re-entry device 3600 is advanced into the center lumen of the orienting device 3400, the flap 3426 causes the distal end of the re-entry device 3600 to be directed out the side port 3425. Further advancement of the re-entry device 3600 causes it to engage the vascular wall, and by action of the tip of re-entry device 3600 (e.g., rotational abrasion), it may penetrate the vascular wall and enter into the vascular true lumen 116 distal of the occlusion 120.

Orienting Methods Using Planar Orienting Elements

Some of the orienting devices (e.g., 3330, 3340, 3400) described hereinbefore have substantially planar orientation elements with an associated side port for delivery of a re-entry device. The side port is generally oriented at a right angle to the plane of the orienting element. With this arrangement, the side port is either directed toward the vascular true lumen or 180 degrees away from the vascular true lumen. In essence, the orienting device reduces the number of directions the side port may be facing from 360 degrees of freedom to two degrees of freedom, 180 degrees apart. The following is a description of methods to determine if the port is directed toward or away from the true lumen, thus reducing two degrees of freedom to one degree of freedom. Generally, if the side port is directed away from the true lumen, the orienting device may be retracted, rotated 180 degrees, and re-deployed to direct the side port toward the true lumen. A re-entry device as described elsewhere herein may then be advanced through the side port, through the vascular wall and into the true lumen.

Figure 35A:
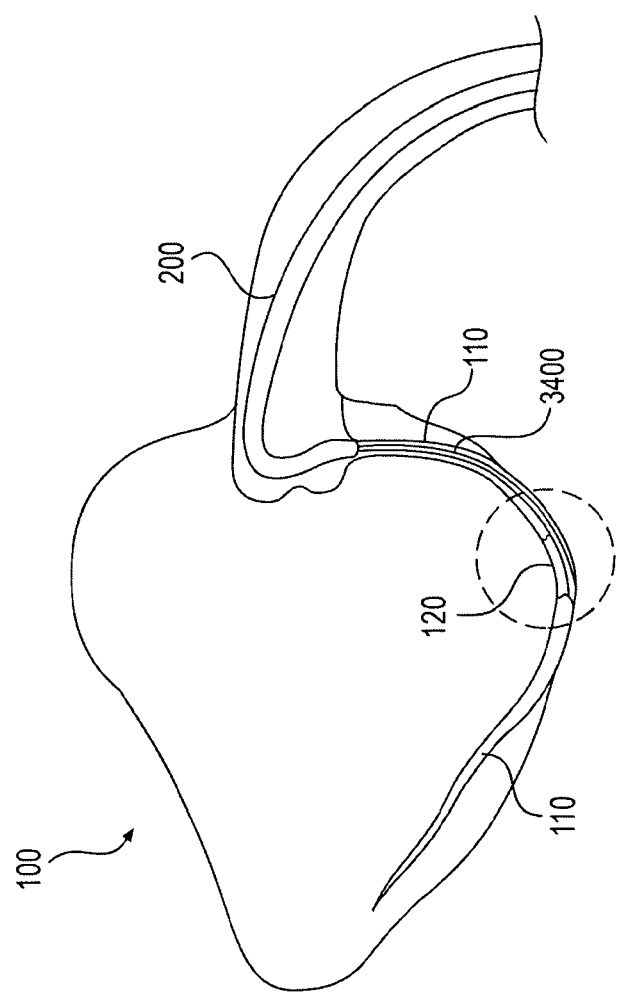
FIGS. 35A-35C schematically illustrate alternative methods for orienting toward the true lumen of the artery.
Figure 35B:
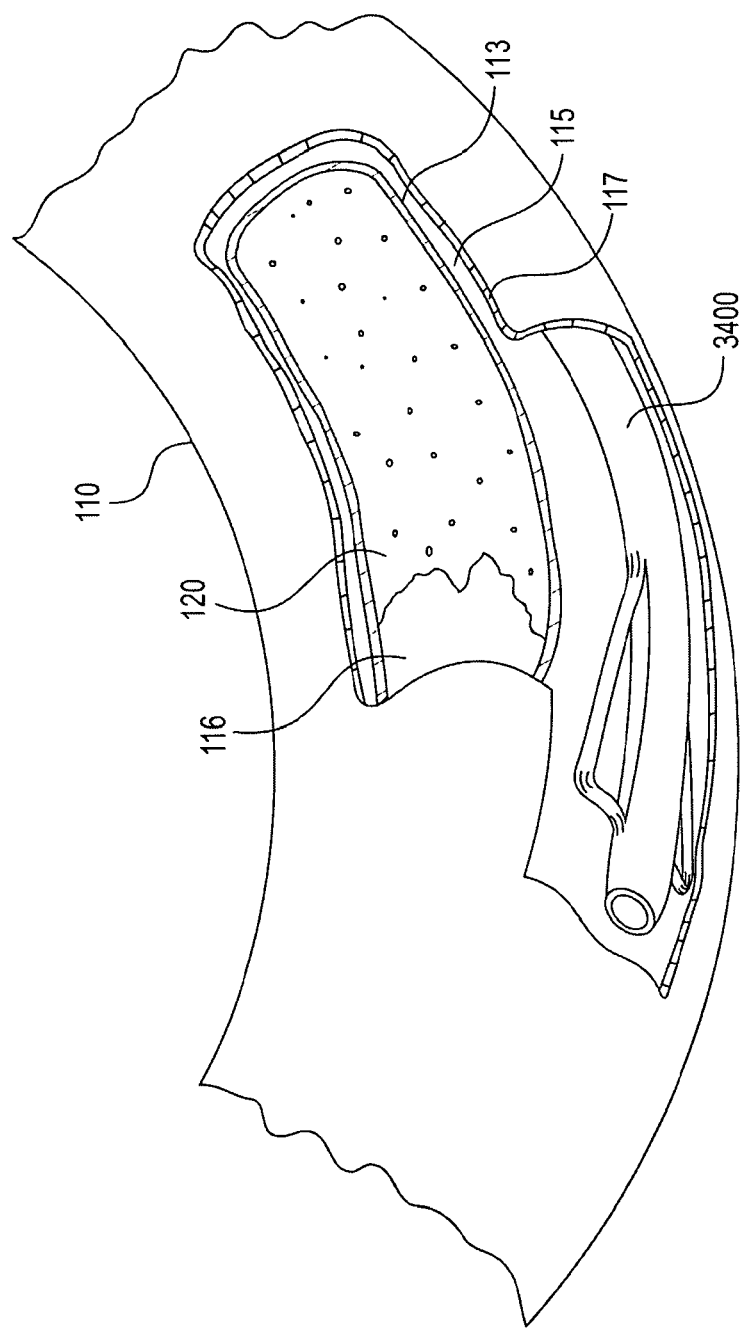
Figure 35C:
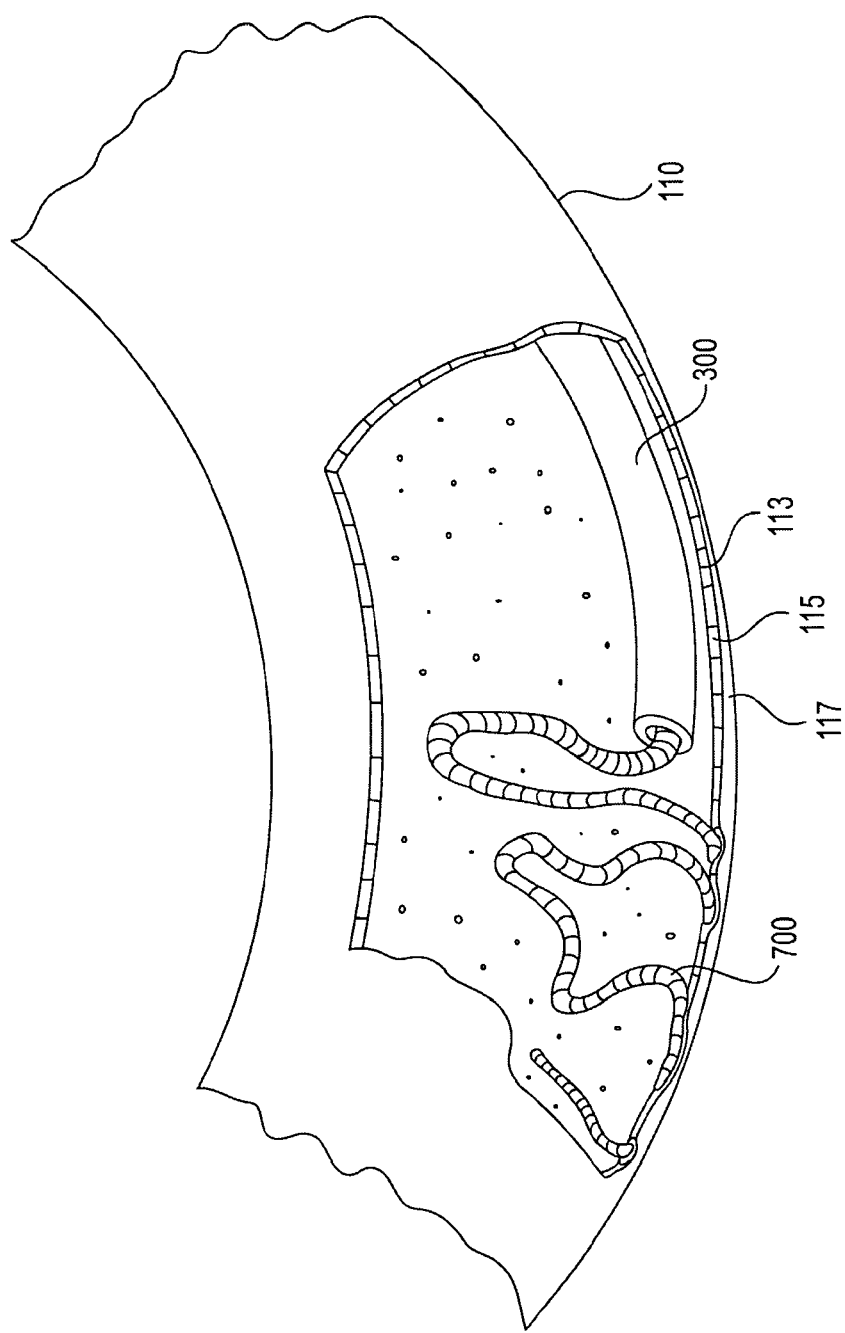

One method of directing the side port toward the true lumen involves taking advantage of the curvature of the heart 100. Generally speaking, the coronary arteries including the left anterior descending artery 110 as shown in FIG. 35A will follow the outside curvature of the bean 100. An orienting device (e.g., 3330, 3340, 3400) inserted into the coronary artery 110 via a guide catheter 200 seated in the ostium of the artery 110 will generally follow the outside curvature of the artery 110 within the subintimal space and across the occlusion 120. In this scenario, as seen in FIG. 35B, the true lumen 116 will lie toward the inside of the curvature of the artery 110 and thus the inside curvature (i.e., concave side) of the orienting device 3400. Thus, the side port of the orienting device 3400 may be directed toward the concave side of the curvature which will predictably direct the side port toward the true lumen 116. Directing the side port in this fashion may be facilitated by using radiographic visualization to view one or more radiopaque markers on the orienting device associated with the side port or a radiopaque device (e.g., guide wire) inserted into the orienting device just as it exits the side port. In addition or as an alternative, the orienting device may be pre-curved such that it naturally orients or "keys" with the curvature of the artery with the side port arranged on the concave side of the pre-curve. In addition or as an alternative, a radiopaque device (e.g., guide wire 700) may be substantially advanced and bunched within the subintimal space via a subintimal device (e.g., crossing device 300 or orienting device 3400) as shown in FIG. 35C such that the radiopaque device extends at least partially circumferentially to assume the curvature of the artery with the true lumen oriented toward the concave side thereof.

Alternative Re-entry Devices

With reference to FIGS. 36A-36G, alternative re-entry devices are schematically illustrated. These embodiments may be used with any of the orienting devices described previously, but are particularly suited for use with orienting devices 3330, 3340, and 3400 described herein before.

Generally, each of the foregoing re-entry devices may be sized like a conventional guide wire, having a 0.014 inch diameter profile for coronary applications, for example. Also generally, each of the foregoing re-entry devices utilizes rotary abrasion as a mechanism to penetrate the intimal layer and enter into the true vascular lumen.

With specific reference to FIG. 36A, and to FIG. 36B which is a detailed cross-sectional view of the distal end, re-entry device 3610 includes a distally tapered drive shaft 3612 which may comprise a metallic alloy such as stainless steel or NiTi, for example. The re-entry device 3610 may have a nominal profile of 0.014 inches and a length of 150 cm for coronary applications. The shaft 3612 may have a proximal diameter of 0.014 inches and a distal taper from 0.014 inches to 0.006 to 0.008 inches over approximately 4.0 inches. An abrasive tip 3620 may be connected to the distal end of the shaft 3612 by brazing or welding techniques. The shaft 3612 just proximal of the tip 3620 is configured with sufficient flexibility to allow flexure of the tip 3620 after it penetrates the vascular wall into the true vascular lumen, thus preventing penetration of the opposite vascular wall. The abrasive tip 3620 may comprise metallic alloy tube 3622 such as stainless steel, platinum or platinum-iridium with a weld ball cap 3624. The tube 3622 may have an inside diameter of approximately 0.007 inches and an outside diameter of approximately 0.0105 inches. An abrasive coating such as a 600 grit diamond coating 3626 may be applied to the outer surface of the tube 3622 with a thickness of approximately 0.0015 inches using conventional techniques available from Continental Diamond Tool (New Haven, Ind.).

With reference to FIG. 36C, and to FIG. 36D which is a detailed cross-sectional view of the distal end, re-entry device 3610 further includes a distal coil 3630 disposed over the distal tapered portion of the shaft 3612. The helical coil 3630 may comprise a stainless steel, platinum or platinum-iridium wire having a diameter of approximately 0.003 to 0.004 inches. The helical coil 3630 generally imparts enhanced torqueability without compromising flexibility of the tapered portion of the shaft 3612.

With reference to FIG. 36E, and to FIG. 36F which is a detailed cross-sectional view of the distal end, re-entry device 3610 alternatively includes a cable shaft 3614 comprising a 1 by 7 or 1 by 19 construction having an outside profile diameter of 0.014 inches, for example. The cable shaft 3614 construction generally imparts enhanced torqueability in at least one direction while increasing flexibility.

With reference to FIG. 37, a rotary drive unit 3700 is shown in perspective view. Rotary drive unit 3700 is particularly suited for use with re-entry device 3610 shown in FIGS. 36A-36G, but may be used with other re-entry devices described elsewhere herein, Generally, the rotary drive unit 3700 provides for independent rotation and advancement of a re-entry device, wherein the rotation is provided by a motor and advancement is provided by shortening or lengthening a partial loop of an advancement sleeve that is attached at only one end and may be advanced/retract without moving the motor drive.

rotary drive unit 3700 includes a base 3710 with two vertical mounting plates 3712 and 3714 attached thereto. A motor 3720 is mounted to plate 3714 and is linked by offset gears 3722 to a hollow drive shaft 3724. A lock mechanism 3726 such as a hollow pin vise or collet is secured to the hollow drive shaft 3724. The proximal shaft 3612 of the re-entry device 3610 may be secured to the locking mechanism 3726 such that activation of the motor 3720 by a suitable power supply causes rotation of the re-entry device 3610. An advancement sleeve 3730 may be fixedly attached to the back side of vertical plate 3714 and coaxially aligned with the hollow drive shaft 3724 to receive the re-entry device shaft 3612 therethrough. The advancement sleeve 3720 extends in a semi-loop around limiting block 3716 and slidably through holes in vertical plates 3714 and 3712. The advancement sleeve 3730 does not rotate but rather supports the rotating shaft 3612 of the re-entry device 3610 and thus may be manually held by the treating physician. The advancement sleeve 3730 may be advanced or retracted thus shortening or lengthening, respectively, the semi-loop thereof and thus advancing or retracting the re-entry device 3610 as it rotates. The advancement sleeve 3730 thereby provides tactile feel of the distal tip 3620 of the re-entry device 3610 as it engages tissue without being hampered by the rotary drive thereof.

From the foregoing, it will be apparent to those skilled in the art that the present invention provides, in exemplary non-limiting embodiments, devices and methods for the treatment of chronic total occlusions. Further, those skilled in the art will recognize that the present invention may be manifested in a variety of forms other than the specific embodiments described and contemplated herein. Accordingly, departures from form and detail may be made without departing from the scope and spirit of the present invention as described in the appended claims.

What is claimed is:

1. A system for facilitating treatment via a vascular wall defining a vascular lumen containing an occlusion therein, the system comprising:
   an intramural orienting device defining a longitudinal axis and having an elongate shaft with a lumen extending therethrough to a distally facing opening transverse and intersecting the longitudinal axis, the elongate shaft being configured to be advanced over a guidewire positionable therein;
   wherein the elongate shaft includes a distal orienting element comprising a plurality of extensions configured to extend laterally from the longitudinal axis in a planar fashion, the plurality of extensions formed as a part of the elongate shaft;
   wherein the elongate shaft further includes a distal side opening in communication with the lumen, the distal side opening facing orthogonally relative to the plurality of extensions;
   wherein the plurality of extensions each includes a collapsed delivery configuration and an expanded deployed configuration, and wherein a most proximal portion of each extension that is external the lumen of the elongate shaft in the deployed configuration is also external the lumen of the elongate shaft in the delivery configuration; and
   a re-entry device configured to penetrate vascular tissue, the reentry device sized and configured to be inserted into the lumen of the elongate shaft;
   wherein the re-entry device comprises:
      an elongate drive shaft having a distal tapered section;
      an abrasive tip connected to the distal tapered section of the drive shaft, the abrasive tip having an abrasive coating along an exterior surface of the tip; and
      wherein the distal tapered section is configured to allow flexure of the tip such that after penetration of the re-entry device into the vascular lumen penetration of an opposite vascular wall is prevented.

2. A system of claim 1, wherein the orienting device further comprises a flap disposed in the lumen of the elongate shaft to direct a front-loaded device toward the distal side opening and permitting a back-loaded device to pass proximally through the lumen of the elongate shaft.

3. The system of claim 2, wherein the flap prevents the back-loaded device from exiting the distal side opening.

4. The system of claim 2, wherein the flap is biased to form a ramp in the lumen of the elongate shaft that directs a front-loaded device toward the distal side opening.

5. The system of claim 2, wherein the elongate shaft includes a slot to accommodate the flap.

6. The system of claim 1, wherein the intramural orienting device is configured to direct the distal side opening toward the vascular lumen when the plurality of extensions are in the expanded deployed configuration.

7. The system of claim 1, wherein the plurality of extensions includes two extensions extending in equal and opposite directions in the deployed configuration.

8. The system of claim 7, wherein the extensions each have a distal end and a proximal end, a distal end of the elongate shaft is connected to the distal end of the extensions, and an outer tube slidably receives a proximal portion of the elongate shaft and has a distal end connected to the proximal end of the extensions, such that relative movement between the elongate shaft and the outer tube controls deployment of the extensions.

9. The system of claim 1, wherein the plurality of extensions are integrally formed with a portion of the elongate shaft extending distally from the extensions to the distal facing opening.

10. The system of claim 1, wherein the re-entry device comprises:
an elongate shaft having a distal portion defined by a spiral cut section having a sharpened tip configured to penetrate vascular tissue;
wherein spacing between respective turns of the spiral cut section increases in a distal direction such that a distal portion of the re-entry device is more flexible than a proximal portion; and
wherein the spiral cut section has sufficient flexibility such that after penetration of the re-entry device into the vascular lumen, penetration of an opposite vascular wall is prevented.

11. The system of claim 1, wherein the re-entry device is configured for rotation by a rotary drive.

12. A system for facilitating treatment via a vascular wall defining a vascular lumen containing an occlusion therein, the system comprising:
an intramural orienting device including:
an elongate shaft with a lumen extending therethrough to a distal facing opening along a longitudinal axis of the elongate shaft;
a distal orienting element comprising first and second lateral extensions extending laterally from the elongate shaft; and
a side opening extending through a sidewall of the elongate shaft and in communication with the lumen, wherein the side opening exits the elongate shaft transverse to the longitudinal axis of the elongate shaft and faces orthogonally relative to the first and second lateral extensions;
wherein the first and second lateral extensions are integrally formed with a portion of the elongate shaft extending distally from the first and second lateral extensions to the distal facing opening;
wherein the elongate shaft includes a spiral cut portion proximal to the side opening; and
a re-entry device having a distal tip configured to penetrate vascular tissue, the re-entry device sized and configured to be inserted into the lumen of the orienting device.

13. The system of claim 12, wherein the first and second lateral extensions are formed from a single tubular member.

14. The system of claim 12, wherein the first and second lateral extensions are formed from a single tubular member and as unitary portions of the elongate shaft.

15. A system for facilitating treatment via a vascular wall defining a vascular lumen containing an occlusion therein, the system comprising:
an intramural orienting device including:
an elongate shaft with a lumen extending therethrough to a distal facing opening along a longitudinal axis of the elongate shaft;
a distal orienting element comprising first and second lateral extensions extending laterally from the elongate shaft; and
a side opening extending through a sidewall of the elongate shaft and in communication with the lumen, wherein the side opening exits the elongate shaft transverse to the longitudinal axis of the elongate shaft and faces orthogonally relative to the first and second lateral extensions; and
a re-entry device having a distal tip configured to penetrate vascular tissue, the re-entry device sized and configured to be inserted into the lumen of the orienting device;
wherein the first and second lateral extensions are formed from a single tubular member and as unitary portions of the elongate shaft;
wherein the single tubular member is a metal hypotube.

16. The system of claim 15, wherein the intramural orienting device further comprises a flap disposed in the lumen to direct a front-loaded device outwardly through the side opening and permit a back-loaded device to pass proximally through the lumen past the side opening.

17. The system of claim 15, wherein the first and second lateral extensions comprise first and second hinged wings configured for movement between a collapsed delivery configuration and an expanded substantially planar deployed configuration.

18. The system of claim 15, wherein the first and second lateral extensions are movable from a collapsed delivery configuration to an expanded deployed configuration, and wherein a most proximal portion of each of the first and second extensions that is external the lumen of the elongate shaft in the deployed configuration is also external the lumen of the elongate shaft in the delivery configuration.

19. The system of claim 15, wherein the side opening is located at a longitudinal position along the elongate shaft intermediate a proximal end and a distal end of the first and second lateral extensions.

* * * * *